(12) United States Patent
Lee et al.

(10) Patent No.: US 11,616,202 B2
(45) Date of Patent: Mar. 28, 2023

(54) COMPOUND, COMPOSITION AND ORGANIC OPTOELECTRONIC DEVICE AND DISPLAY DEVICE

(71) Applicants: SAMSUNG SDI CO., LTD., Yongin-si (KR); Samsung Electronics Co., Ltd., Suwon-si (KR)

(72) Inventors: Seungjae Lee, Suwon-si (KR); Changwoo Kim, Suwon-si (KR); Byungku Kim, Suwon-si (KR); Hyung Sun Kim, Suwon-si (KR); Dong Wan Ryu, Suwon-si (KR); Chang Ju Shin, Suwon-si (KR); Kipo Jang, Suwon-si (KR); Min Seok Seo, Suwon-si (KR); Sung-Hyun Jung, Suwon-si (KR)

(73) Assignees: Samsung SDI Co., Ltd., Yongin-si (KR); Samsung Electronics Co., Ltd., Suwon-si (KR)

( * ) Notice: Subject to any disclaimer, the term of this patent is extended or adjusted under 35 U.S.C. 154(b) by 625 days.

(21) Appl. No.: 16/419,723

(22) Filed: May 22, 2019

(65) Prior Publication Data

US 2019/0363261 A1    Nov. 28, 2019

(30) Foreign Application Priority Data

May 28, 2018  (KR) .................. 10-2018-0060520

(51) Int. Cl.
  *C07D 405/14*    (2006.01)
  *H01L 51/00*     (2006.01)
  (Continued)

(52) U.S. Cl.
  CPC ........ *H01L 51/0072* (2013.01); *C07D 405/14* (2013.01); *C09K 11/02* (2013.01);
  (Continued)

(58) Field of Classification Search
  None
  See application file for complete search history.

(56) References Cited

U.S. PATENT DOCUMENTS 5,061,569 A    10/1991   Vanslyke et al.
2015/0171340 A1  6/2015   Lee et al.
(Continued)

FOREIGN PATENT DOCUMENTS

CN    106459018 A    2/2017
JP    H059471 A      1/1993
(Continued)

OTHER PUBLICATIONS

Extended European Search Report dated Sep. 18, 2019, of corresponding European Patent Application No. 19176896.9.
(Continued)

*Primary Examiner* — Clinton A Brooks
(74) *Attorney, Agent, or Firm* — Lee IP Law, P.C.

(57) ABSTRACT

A compound represented by a combination of Chemical Formula 1 and Chemical Formula 2 bonded together, a composition including the compound, an organic optoelectronic device, and a display device are disclosed.

[Chemical Formula 1]

(Continued)

-continued

[Chemical Formula 2]

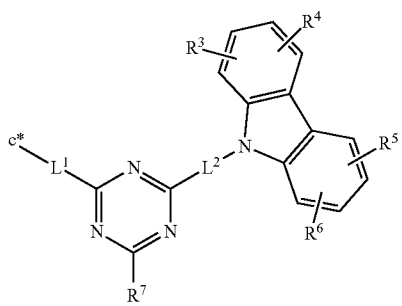

In Chemical Formula 1 and Chemical Formula 2, each substituent is the same as described in the specification.

16 Claims, 1 Drawing Sheet

(51) Int. Cl.
  *C09K 11/02* (2006.01)
  *C09K 11/06* (2006.01)
  *H01L 51/50* (2006.01)

(52) U.S. Cl.
  CPC .......... *C09K 11/06* (2013.01); *H01L 51/0067* (2013.01); *H01L 51/0073* (2013.01); *C09K 2211/1007* (2013.01); *C09K 2211/1029* (2013.01); *C09K 2211/185* (2013.01); *H01L 51/5012* (2013.01); *H01L 51/5016* (2013.01)

(56) References Cited

U.S. PATENT DOCUMENTS

| | | |
|---|---|---|
| 2015/0318487 A1 | 11/2015 | Ito |
| 2016/0197285 A1 | 7/2016 | Zeng et al. |

FOREIGN PATENT DOCUMENTS

| | | |
|---|---|---|
| JP | H07126615 A | 5/1995 |
| JP | H1095972 A | 4/1998 |
| JP | 2010-040830 A | 2/2010 |
| JP | 2017-107992 A | 6/2017 |
| KR | 10-2013-0094903 A | 8/2013 |
| KR | 10-2014-0046541 A | 4/2014 |
| KR | 10-2014-0144550 A | 12/2014 |
| KR | 10-2015-0064878 A | 6/2015 |
| KR | 10-2015-0070860 A | 6/2015 |
| KR | 10-2017-0101021 | 9/2017 |
| KR | 10-2017-0113398 A | 10/2017 |
| KR | 10-2018-0002351 A | 1/2018 |
| KR | 10-2018-0002353 A | 1/2018 |
| KR | 10-2018-0007243 A | 1/2018 |
| KR | 10-2018-0010808 A | 1/2018 |
| KR | 10-1833669 B1 | 2/2018 |
| KR | 10-2018-0022189 A | 3/2018 |
| KR | 10-2018-0055484 | 5/2018 |
| KR | 10-2019-0000185 | 1/2019 |
| KR | 10-2019-0001357 | 1/2019 |
| KR | 10-2019-0013139 | 2/2019 |
| TW | 201327959 | 7/2013 |
| TW | 201623292 A | 7/2016 |
| TW | 201731839 A | 9/2017 |
| TW | 201803855 A | 2/2018 |
| WO | WO 9509147 A1 | 4/1995 |
| WO | WO 2013/035275 A1 | 3/2013 |
| WO | WO 2013/077362 A1 | 5/2013 |
| WO | WO 2014/054912 A1 | 4/2014 |
| WO | WO 2019/017734 A1 | 1/2019 |

OTHER PUBLICATIONS

Taiwanese Office Action dated Dec. 26, 2019 and Search Report dated Dec. 2, 2019.

[FIG. 1]
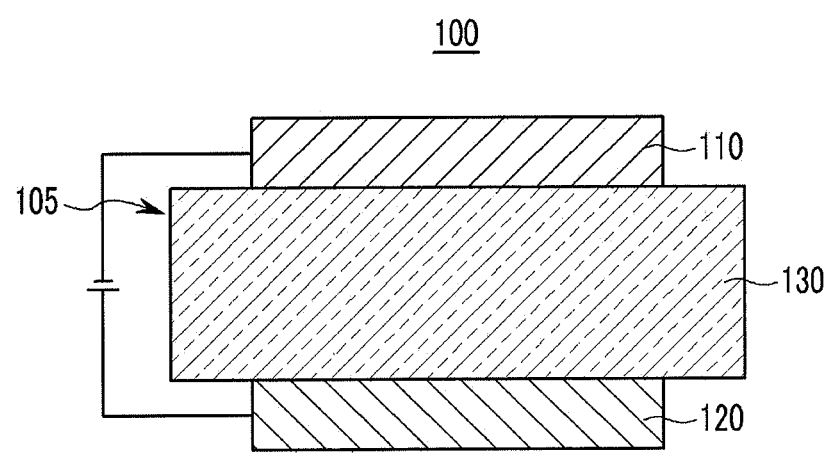
[FIG. 2]
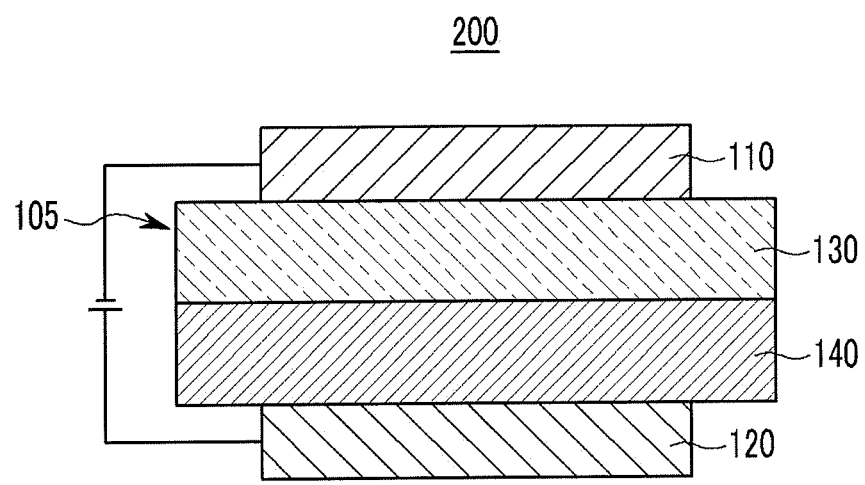

COMPOUND, COMPOSITION AND ORGANIC OPTOELECTRONIC DEVICE AND DISPLAY DEVICE

CROSS-REFERENCE TO RELATED APPLICATION

Korean Patent Application No. 10-2018-0060520, filed on May 28, 2018, in the Korean Intellectual Property Office, and entitled: "Compound, Composition and Organic Optoelectronic Device and Display Device," is incorporated by reference herein in its entirety.

BACKGROUND

1. Field

Embodiments relate to a compound, a composition, organic optoelectronic device, and a display device.

2. Description of the Related Art

An organic optoelectronic device may be used to convert electrical energy into photo energy or vice versa.

An organic optoelectronic device may be classified as follows in accordance with its driving principles. One is a photoelectric device where excitons are generated by photo energy, separated into electrons and holes, and are transferred to different electrodes to generate electrical energy. Another is a light emitting device where a voltage or a current is supplied to an electrode to generate photo energy from electrical energy.

Examples of the organic optoelectronic diode may be an organic photoelectric device, an organic light emitting diode, an organic solar cell, and an organic photo conductor drum.

SUMMARY

Embodiments are directed to a compound represented by a combination of Chemical Formula 1 and Chemical Formula 2 bonded together:

[Chemical Formula 1]

[Chemical Formula 2]

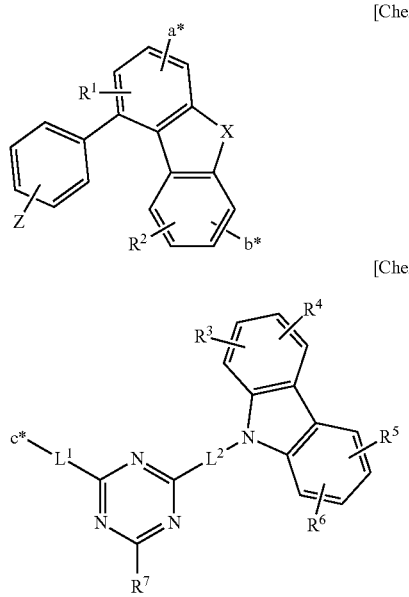

In Chemical Formula 1 and Chemical Formula 2,

X may be O or S,

Z may be hydrogen, deuterium, a substituted or unsubstituted C1 to C10 alkyl group, or a substituted or unsubstituted phenyl group, $L^1$ and $L^2$ may each independently be a single bond, or a substituted or unsubstituted C6 to C20 arylene group, one of a* and b* of Chemical Formula 1 is a bond with c* of Chemical Formula 2, and the other of a* and b* of Chemical Formula 1 may be hydrogen, deuterium, a substituted or unsubstituted C1 to C10 alkyl group, or a substituted or unsubstituted C6 to C20 aryl group, and $R^1$ to $R^7$ may each independently be hydrogen, deuterium, a substituted or unsubstituted C1 to C10 alkyl group, or a substituted or unsubstituted C6 to C20 aryl group.

According to another embodiment, a composition includes a first compound that is represented by a combination of Chemical Formula 1 and Chemical Formula 2, and a second compound represented by Chemical Formula 3.

[Chemical Formula 3]

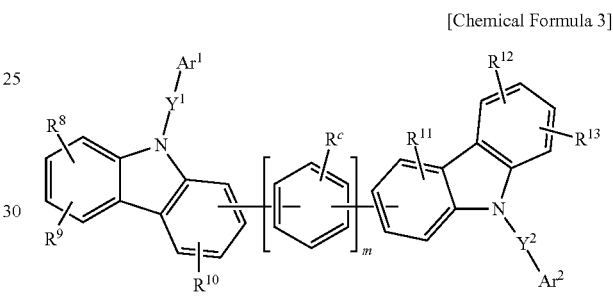

In Chemical Formula 3, $Y^1$ and $Y^2$ may each independently be a single bond or a substituted or unsubstituted C6 to C20 arylene group, $Ar^1$ and $Ar^2$ may each independently be a substituted or unsubstituted C6 to C20 aryl group or a substituted or unsubstituted C2 to C30 heterocyclic group, $R^c$ and $R^8$ to $R^{13}$ may each independently be hydrogen, deuterium, a substituted or unsubstituted C1 to C10 alkyl group, a substituted or unsubstituted C6 to C20 aryl group, a substituted or unsubstituted C2 to C30 heterocyclic group, a cyano group, or a combination thereof, and m may be 0, 1, or 2.

According to another embodiment, an organic optoelectronic device includes an anode and a cathode facing each other, and at least one organic layer disposed between the anode and the cathode, wherein the organic layer includes the compound or the composition.

According to yet another embodiment, a display device includes the organic optoelectronic device.

BRIEF DESCRIPTION OF THE DRAWINGS

Features will become apparent to those of skill in the art by describing in detail example embodiments with reference to the attached drawings in which:

FIGS. 1 and 2 illustrate cross-sectional views of organic light emitting diodes according to example embodiments.

DETAILED DESCRIPTION

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey example implementations to those skilled in the art. Like reference numerals refer to like elements throughout.

As used herein, when a definition is not otherwise provided, the "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, C1 to C20 alkoxy group, a C1 to C10 trifluoroalkyl group, a cyano group, or a combination thereof.

In one example of the present disclosure, the "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, or a cyano group. In addition, in specific examples of the present disclosure, the "substituted" refers to replacement of at least one hydrogen of a substituent or a compound by deuterium, a C1 to C20 alkyl group, a C6 to C30 aryl group, or a cyano group. In addition, in specific examples of the present disclosure, the "substituted" refers to replacement of at least one hydrogen of a substituent or a compound by deuterium, a C1 to C5 alkyl group, a C6 to C18 aryl group, or a cyano group. In addition, in specific examples of the present disclosure, the "substituted" refers to replacement of at least one hydrogen of a substituent or a compound by deuterium, a cyano group, a methyl group, an ethyl group, a propyl group, a butyl group, a phenyl group, a biphenyl group, a terphenyl group, or a naphthyl group.

As used herein, when a definition is not otherwise provided, "hetero" refers to one including one to three heteroatoms selected from N, O, S, P, and Si, and remaining carbons in one functional group.

As used herein, the "aryl group" refers to a group including at least one hydrocarbon aromatic moiety, and all the elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, and two or more hydrocarbon aromatic moieties are fused directly or indirectly to provide a non-aromatic fused ring, for example a fluorenyl group.

The aryl group may include a monocyclic, polycyclic or fused ring polycyclic (i.e., rings sharing adjacent pairs of carbon atoms) functional group.

As used herein, the "heterocyclic group" is a generic concept of a heteroaryl group, and may include at least one hetero atom selected from N, O, S, P, and Si instead of carbon (C) in a cyclic compound such as aryl group, a cycloalkyl group, a fused ring thereof, or a combination thereof. When the heterocyclic group is a fused ring, the entire ring or each ring of the heterocyclic group may include one or more heteroatoms.

In an example embodiment, the "heteroaryl group" may refer to an aryl group including at least one hetero atom selected from N, O, S, P, and Si instead of carbon (C). Two or more heteroaryl groups are linked by a sigma bond directly, or when the C2 to C60 heteroaryl group includes two or more rings, the two or more rings may be fused. When the heteroaryl group is a fused ring, each ring may include 1 to 3 hetero atoms.

Specific examples of the heterocyclic group may be a pyridinyl group, a pyrimidinyl group, a pyrazinyl group, a pyridazinyl group, a triazinyl group, a quinolinyl group, an isoquinolinyl group, and the like.

For example, the substituted or unsubstituted C6 to C30 aryl group and/or the substituted or unsubstituted C2 to C30 heterocyclic group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylenyl group, a substituted or unsubstituted perylenyl group, a substituted or unsubstituted fluorenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted carbazolyl group, a substituted or unsubstituted dibenzofuranyl group, or a substituted or unsubstituted dibenzothiophenyl group, or combination thereof, but are not limited thereto.

In the present specification, hole characteristics refer to an ability to donate an electron to form a hole when an electric field is applied, and that a hole formed in the anode may be easily injected into a light emitting layer, and a hole formed in a light emitting layer may be easily transported into an anode and transported in the light emitting layer due to conductive characteristics according to a highest occupied molecular orbital (HOMO) level.

In addition, electron characteristics refer to an ability to accept an electron when an electric field is applied, and that an electron formed in a cathode may be easily injected into a light emitting layer, and an electron formed in a light emitting layer may be easily transported into a cathode and transported in the light emitting layer due to conductive characteristics according to a lowest unoccupied molecular orbital (LUMO) level.

Hereinafter, a compound according to an embodiment is described.

A compound according to an embodiment is represented by a combination of Chemical Formula 1 and Chemical Formula 2 bonded together:

[Chemical Formula 1]

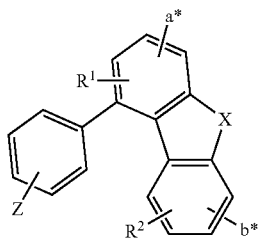

[Chemical Formula 2]

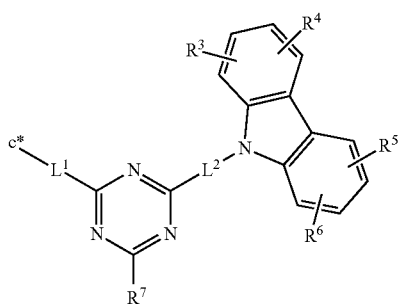

In Chemical Formula 1 and Chemical Formula 2,

X may be O or S,

Z may be hydrogen, deuterium, a substituted or unsubstituted C1 to C10 alkyl group, or a substituted or unsubstituted phenyl group, $L^1$ and $L^2$ may each independently be a single bond, or a substituted or unsubstituted C6 to C20 arylene group, a* or b* of Chemical Formula 1 is linked with c* of Chemical Formula 2, and a* or b* of Chemical Formula 2 not linking with c* and $R^1$ to $R^7$ may each independently be hydrogen, deuterium, a substituted or unsubstituted C1 to C10 alkyl group, or a substituted or unsubstituted C6 to C20 aryl group.

Without being bound by theory, the compound represented by combining Chemical Formulae 1 and 2 may exhibit enhanced stability from a triazine moiety connected with dibenzofuran (or dibenzothiophene) and simultaneously provide further stability through a bipolar characteristic by applying a carbazole moiety. Through applying a carbazole moiety, a glass transition temperature relative to a molecular weight may be effectively improved to help provide heat resistance. A phenyl group is substituted at No. 1 position of dibenzofuran (or dibenzothiophene) to improve electron mobility, such that the deposited layer is effectively improved to provide a device with low driving, high efficient and long life-span characteristics.

The compound represented by the combination of Chemical Formulae 1 and 2 may be, for example, represented by Chemical Formula 1A or Chemical Formula 1B according to a specific linking point of Chemical Formulae 1 and 2.

[Chemical Formula 1A]

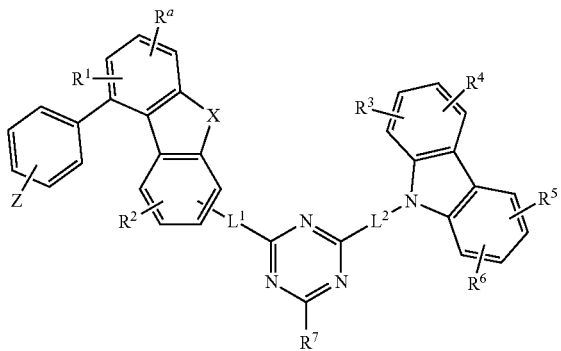

[Chemical Formula 1B]

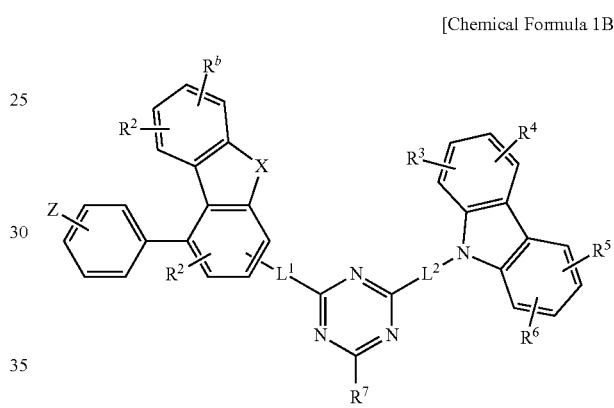

In Chemical Formula 1A and Chemical Formula 1B, X, Z, $L^1$ and $L^2$, $R^a$, $R^b$ and $R^1$ to $R^7$ are the same as described above.

According to the specific position where dibenzofuran (or dibenzothiophene) is linked with triazine through $L^1$, the compound represented by combining Chemical Formulae 1 and 2 may be represented by, for example, any one of Chemical Formulae 1A-1 to 1A-4 and Chemical Formulae 1B-1 to Chemical Formula 1B-3.

[Chemical Formula 1A-1]

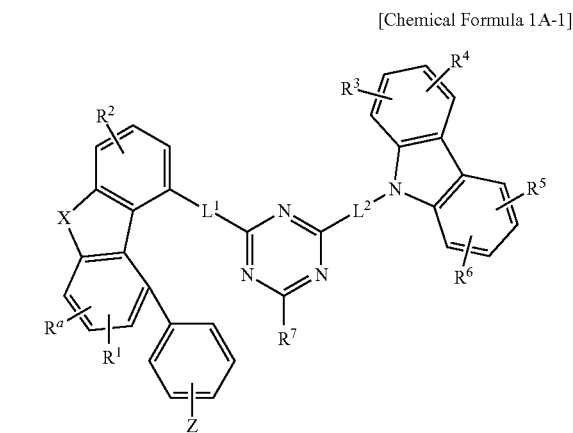

[Chemical Formula 1A-2]

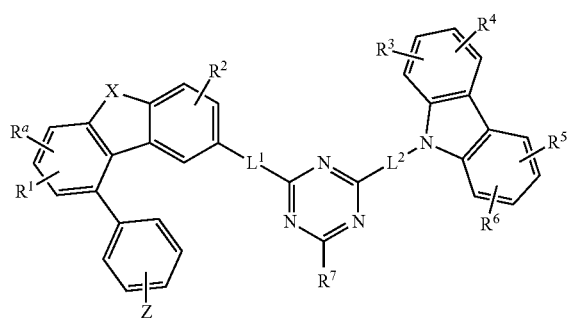

[Chemical Formula 1B-2]

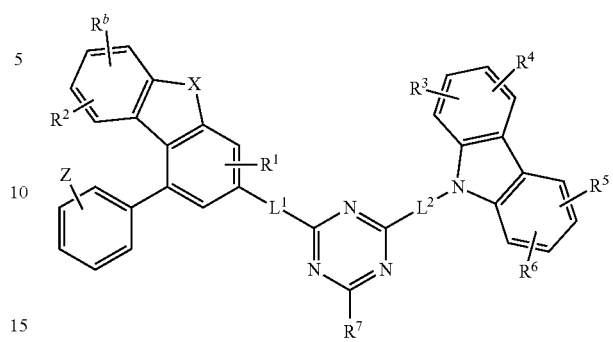

[Chemical Formula 1A-3]

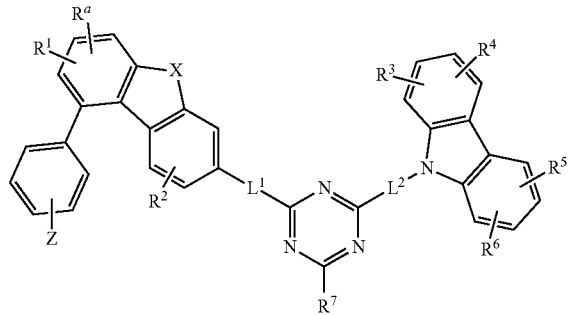

[Chemical Formula 1B-3]

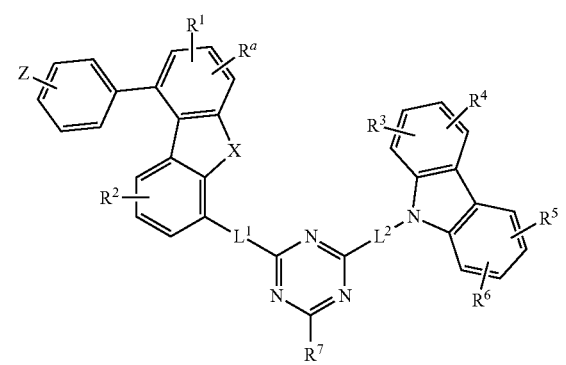

[Chemical Formula 1A-4]

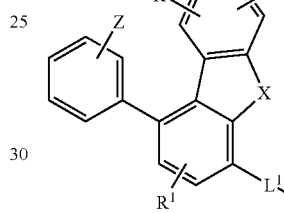

In Chemical Formula 1A-1 to Chemical Formula 1A-4 and Chemical Formula 1B-1 to Chemical Formula 1B-3, X, Z, $L^1$, $L^2$, $R^a$, $R^b$ and $R^1$ to $R^7$ are the same as described above.

In an example embodiment, the compound represented by the combination of Chemical Formulae 1 and 2 may be represented by Chemical Formula 1A-3 or Chemical Formula 1B-2.

Chemical Formula 1A-3 may be, for example, represented by one of Chemical Formulae 1A-3a to 1A-3c according to a specific substitution position of $R^1$ or $R^2$.

[Chemical Formula 1B-1]

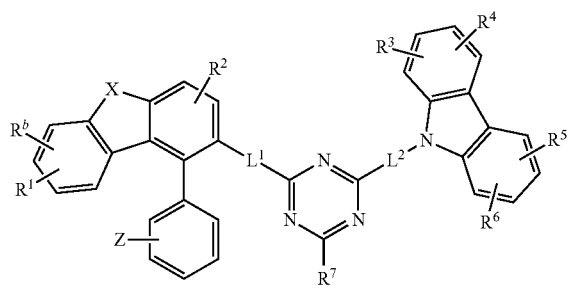

[Chemical Formula 1A-3a]

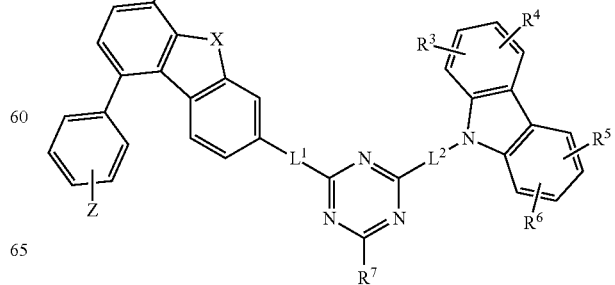

[Chemical Formula 1A-3b]

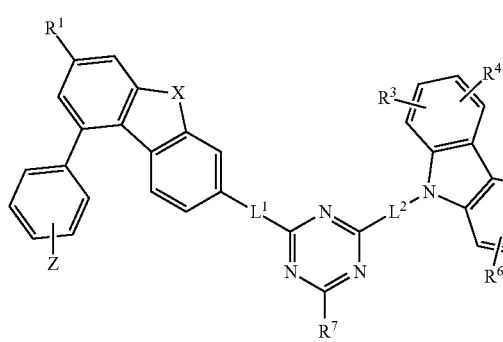

[Chemical Formula 1A-3f]

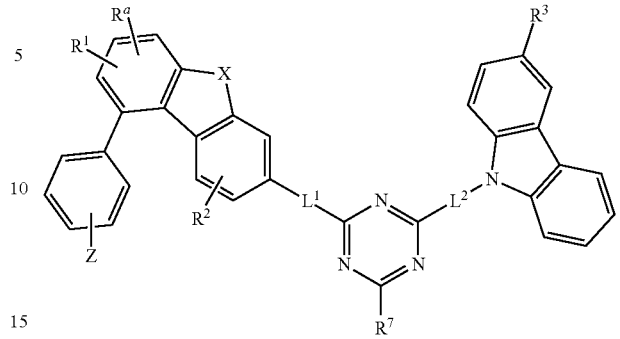

[Chemical Formula 1A-3c]

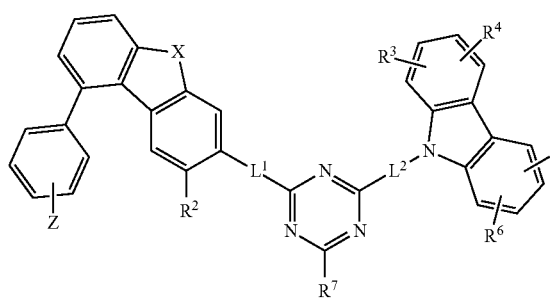

[Chemical Formula 1A-3g]

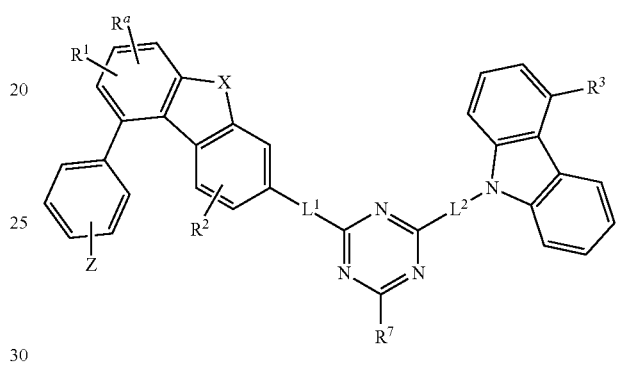

In addition, Chemical Formula 1A-3 may be, for example, represented by one of Chemical Formulae 1A-3d to 1A-3g according to specific substitution positions of $R^3$ to $R^6$.

In addition, Chemical Formula 1A-3 may be, for example, represented by Chemical Formula 1A-3h or Chemical Formula 1A-3i according to a specific substitution position of Z.

[Chemical Formula 1A-3d]

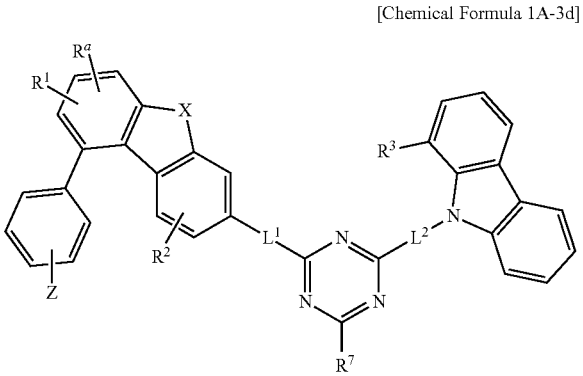

[Chemical Formula 1A-3h]

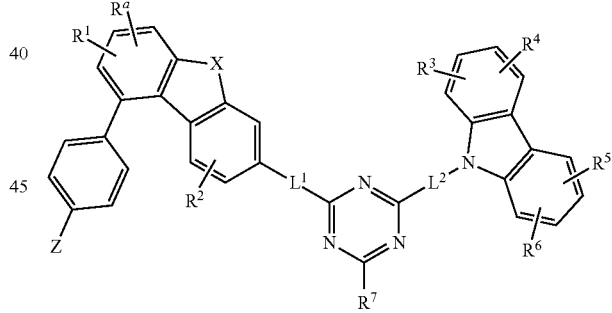

[Chemical Formula 1A-3e]

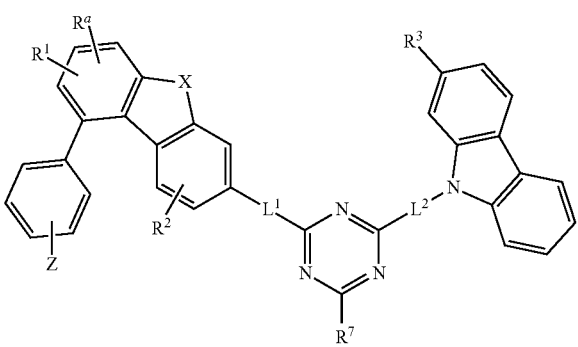

[Chemical Formula 1A-3i]

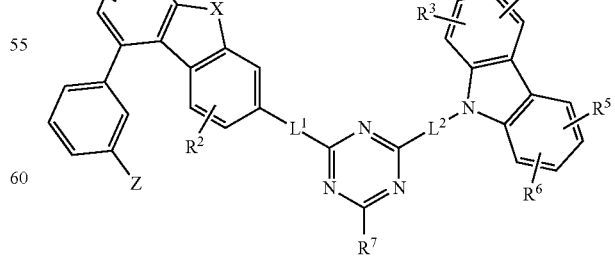

In Chemical Formula 1A-3a to Chemical Formula 1A-3i, X, Z, $L^1$, $L^2$, $R^a$ and $R^1$ to $R^7$ are the same as described above.

For example, Chemical Formula 1B-2 may be, for example, represented by one of Chemical Formula 1B-2a to Chemical Formula 1B-2c according to a specific substitution position of $R^1$ or $R^2$.

[Chemical Formula 1B-2a]

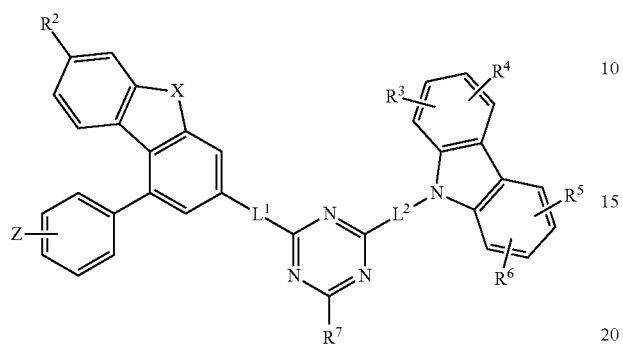

[Chemical Formula 1B-2b]

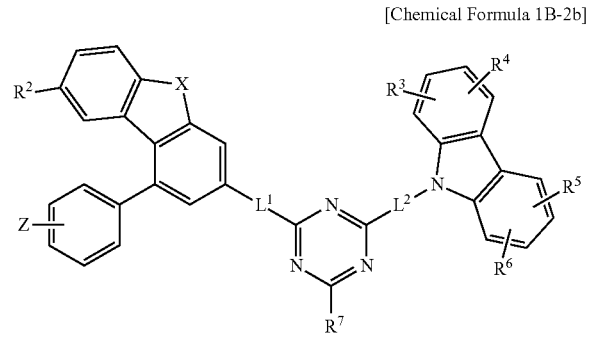

[Chemical Formula 1B-2c]

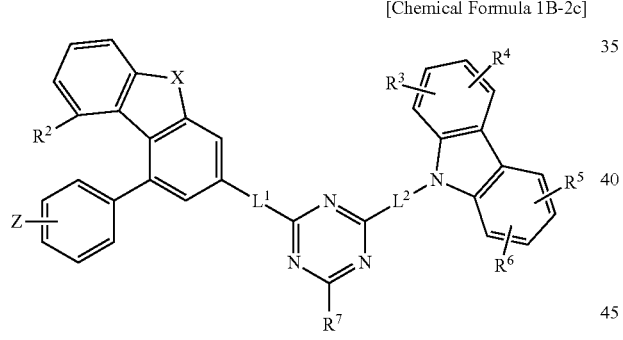

In addition, Chemical Formula 1B-2 may be, for example, represented by one of Chemical Formula 1B-2d to 1B-2g according to specific substitution positions of $R^3$ to $R^6$.

[Chemical Formula 1B-2d]

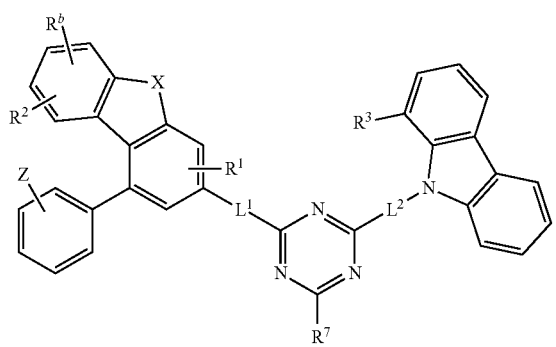

[Chemical Formula 1B-2e]

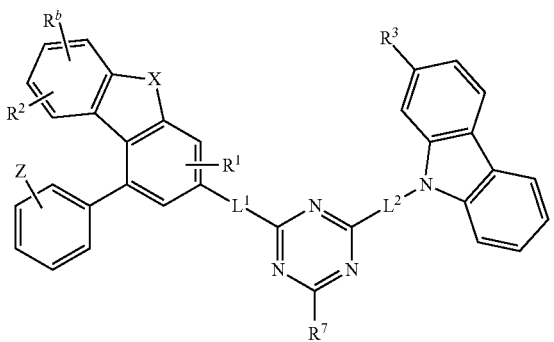

[Chemical Formula 1B-2f]

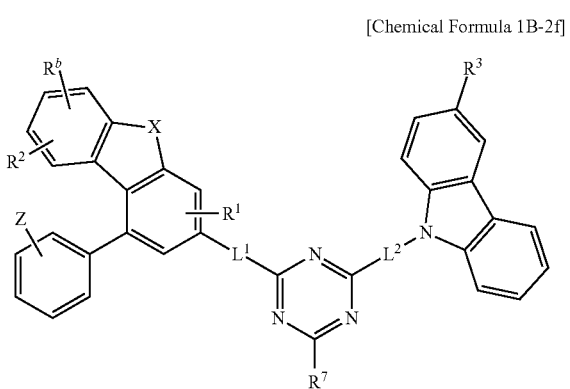

[Chemical Formula 1B-2g]

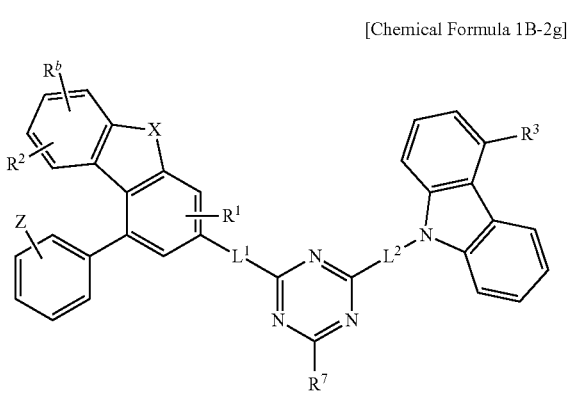

In addition, Chemical Formula 1B-2 may be, for example, represented by Chemical Formula 1B-2h or Chemical Formula 1B-2i according to a specific substitution position of Z.

[Chemical Formula 1B-2h]

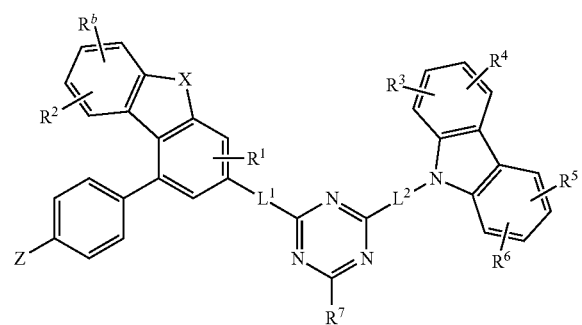

-continued

[Chemical Formula 1B-2i]

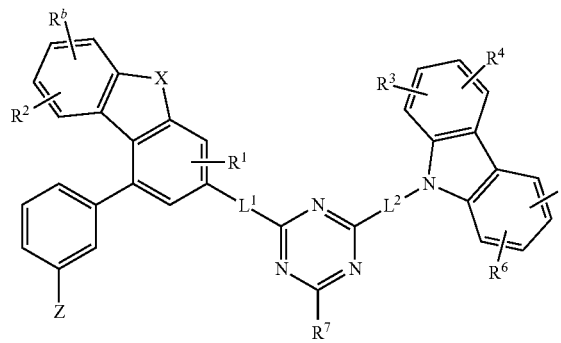

In Chemical Formula 1B-2a to Chemical Formula 1B-2i, X, Z, L$^1$, L$^2$, R$^b$ and R$^1$ to R$^7$ are the same as described above.

In an example embodiment, X may be O.

In an example embodiment, Z may be hydrogen, a C1 to C5 alkyl group, or a phenyl group.

In an example embodiment, L$^1$ and L$^2$ may each independently be a single bond or a substituted or unsubstituted phenylene group, and specifically a single bond or an m-phenylene group. For example. L$^1$ may be a single bond and L$^2$ may be an m-phenylene group.

In an example embodiment, R$^1$ to R$^7$ may each independently be hydrogen or a substituted or unsubstituted C6 to C20 aryl group.

For example, R$^1$ to R$^6$ may each independently be hydrogen or a phenyl group, and R$^7$ may be a substituted or unsubstituted C6 to C20 aryl group.

For example, R$^7$ may be a substituted or unsubstituted phenyl group, a substituted or unsubstituted biphenyl group, a substituted or unsubstituted naphthyl group, a substituted or unsubstituted terphenyl group, a substituted or unsubstituted anthracenyl group, a substituted or unsubstituted phenanthrenyl group, or a substituted or unsubstituted triphenylene group.

In an example embodiment, R$^7$ may be one of substituents of Group I.

In an example embodiment, the compound represented by the combination of Chemical Formula 1 and Chemical Formula 2 may be represented by one of Chemical Formula 1A-3f, Chemical Formula 1A-3h, Chemical Formula 1A-3i, Chemical Formula 1B-2f, Chemical Formula 1B-2h, and Chemical Formula 1B-2i, wherein X is O or S, Z is hydrogen or a phenyl group, L$^1$ and L$^2$ may each independently be a single bond or phenylene group, R$^a$, R$^1$, R$^2$, and R$^4$ to R$^6$ are hydrogen, and R$^3$ is hydrogen or a phenyl group.

In an example embodiment, the compound represented by the combination of Chemical Formula 1 and Chemical Formula 2 may be one of compounds of Group 1:

[Group 1]

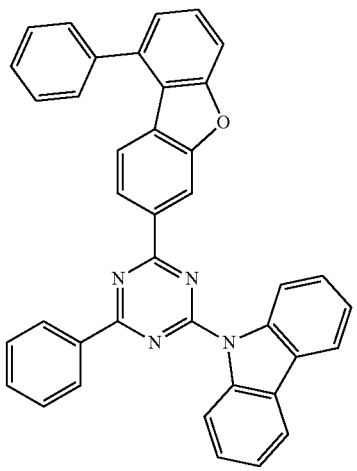

[A-1]

[Group I]

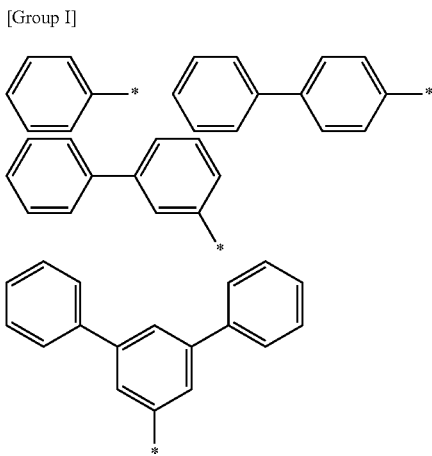

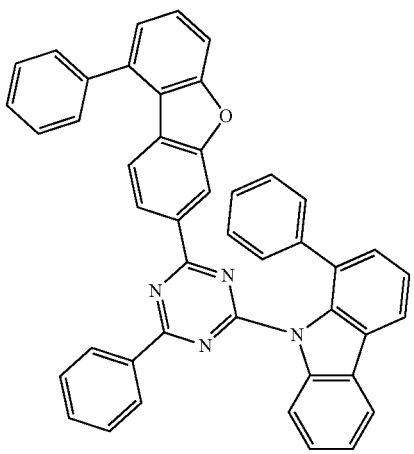

[A-2]

[A-3]
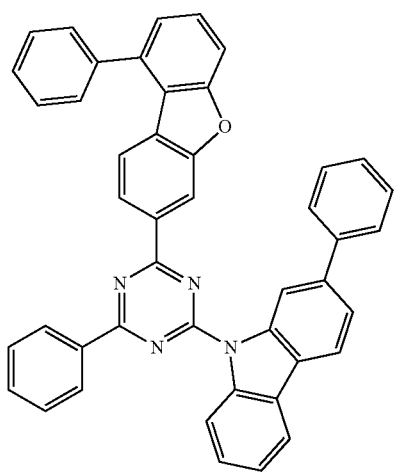
[A-4]
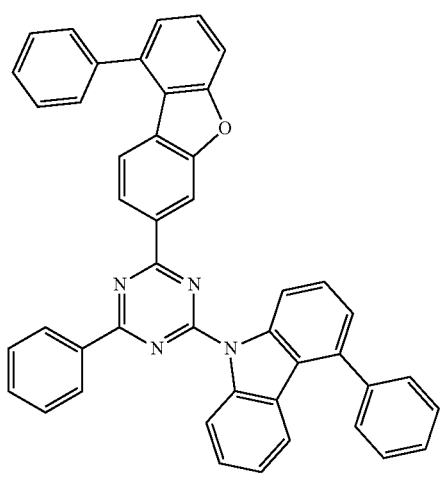
[A-5]
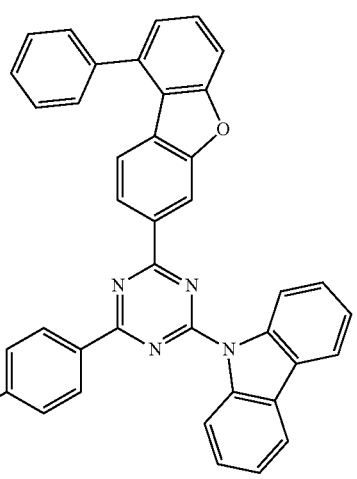
[A-6]
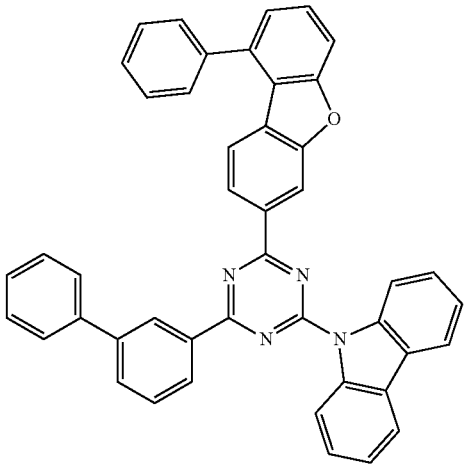
[A-7]
[A-8]
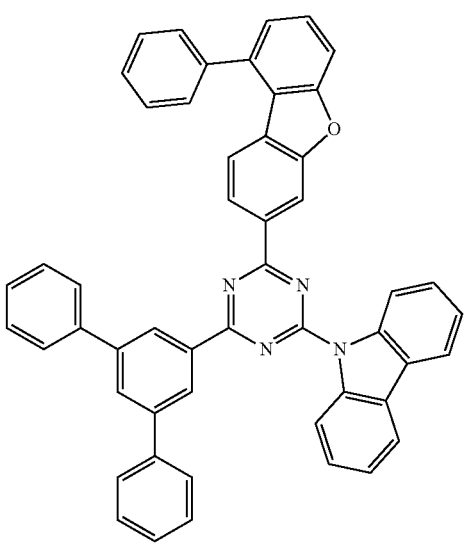

[A-9]
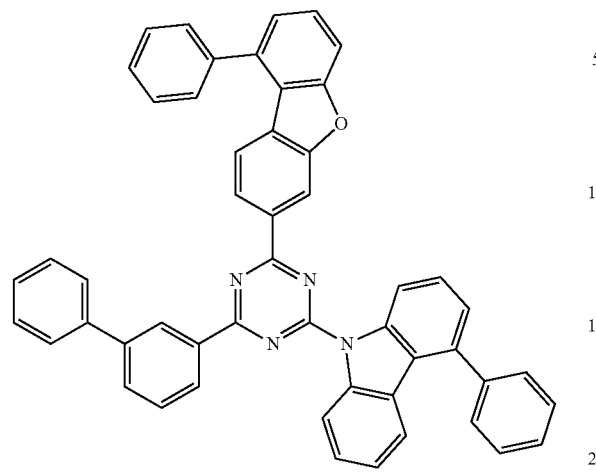
[A-10]
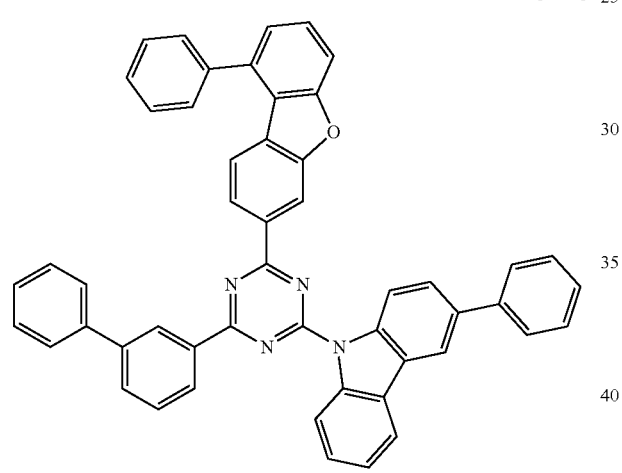
[A-11]
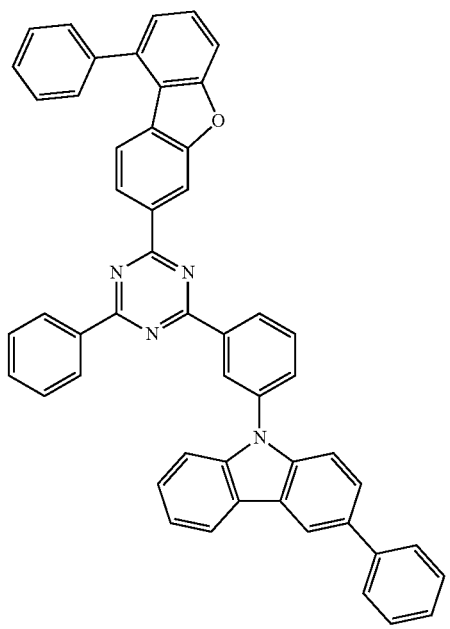
[A-12]
[A-13]
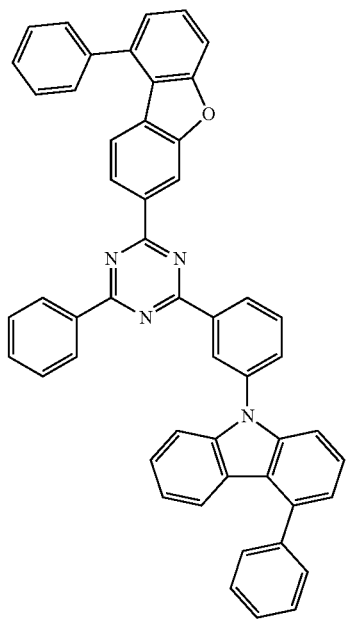

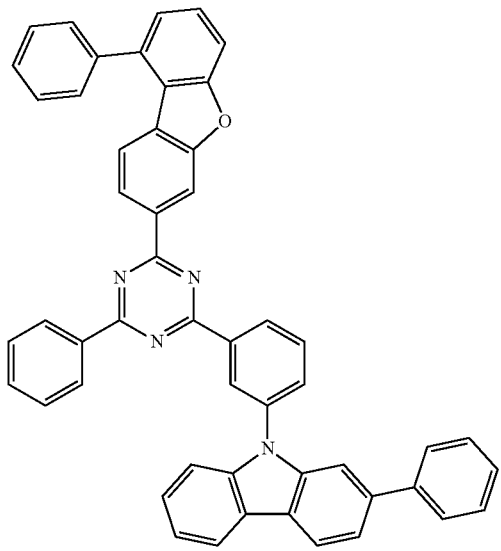 [A-14]
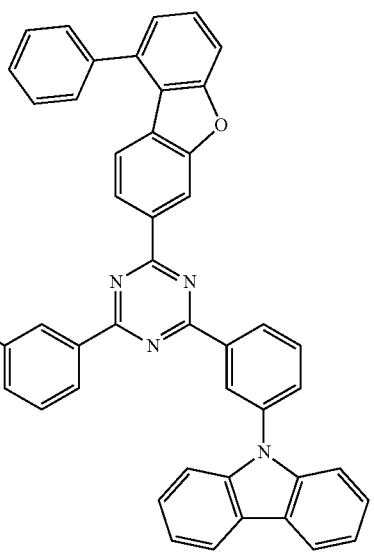 [A-16]
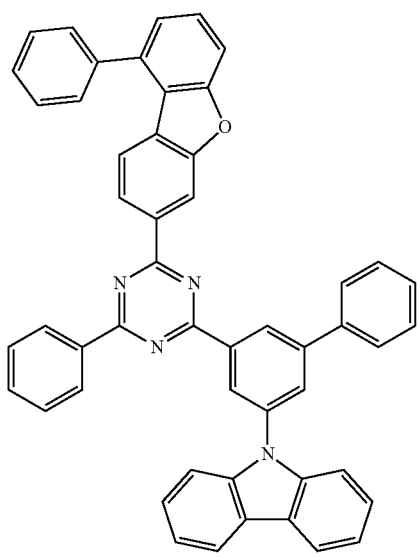 [A-15]
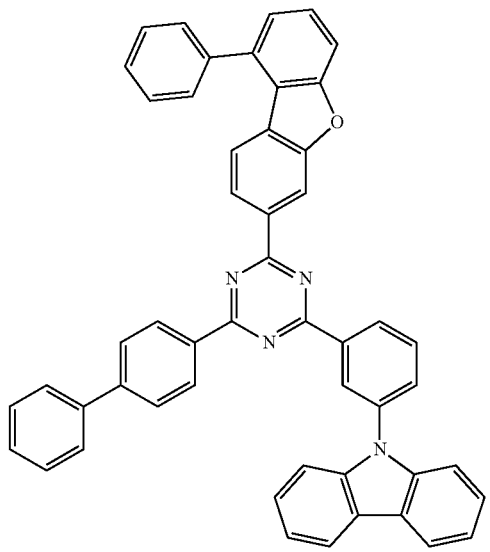 [A-17]

[A-18]
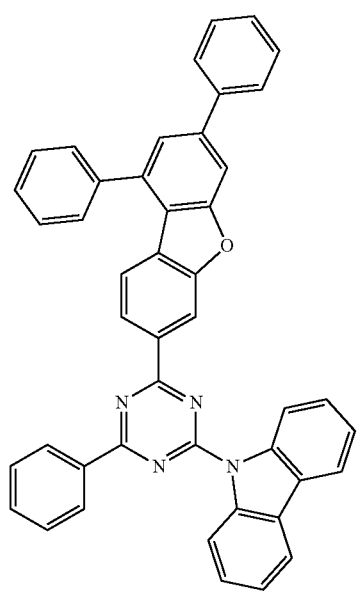
[A-19]
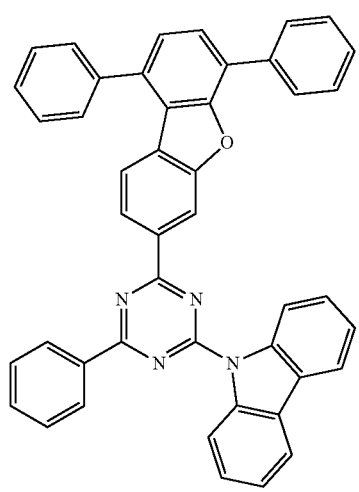
[A-20]
[A-21]
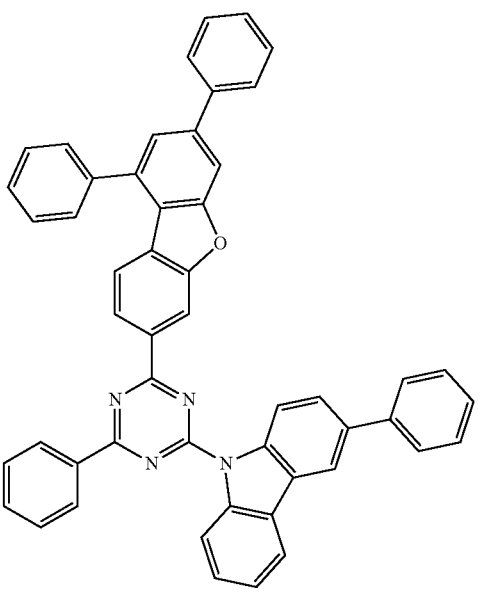
[A-22]
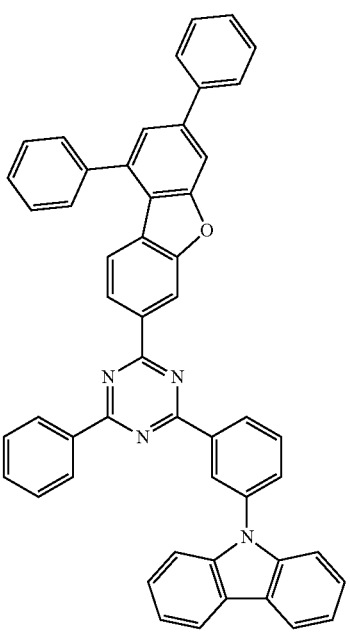

[A-23]
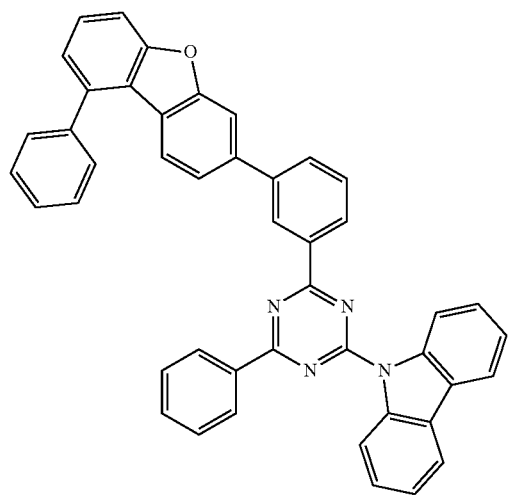
[A-24]
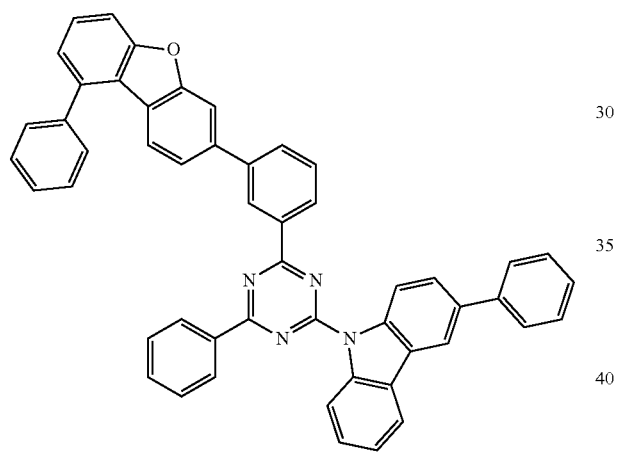
[A-25]
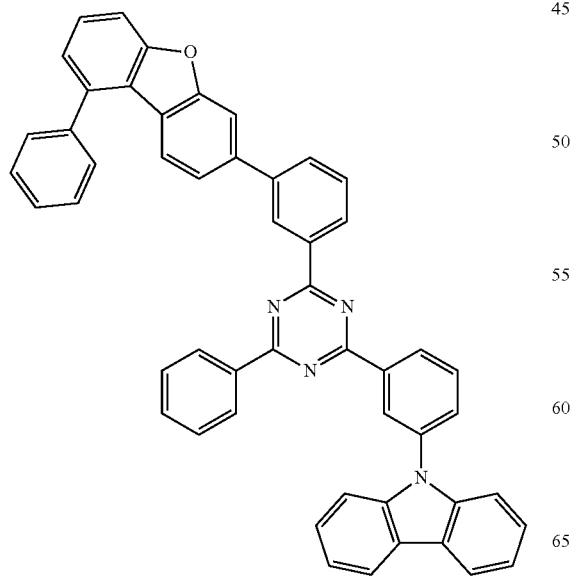
[A-26]
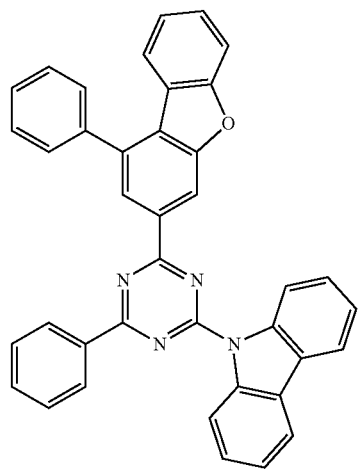
[A-27]
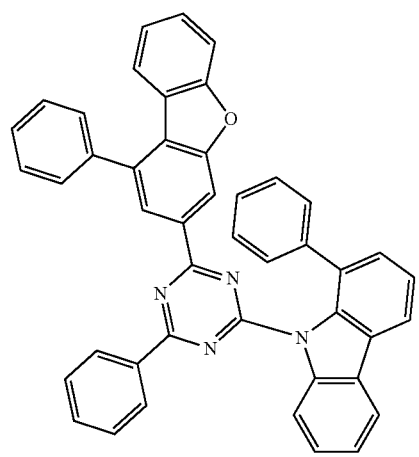
[A-28]
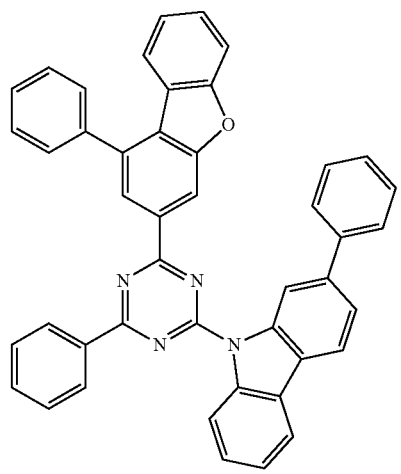

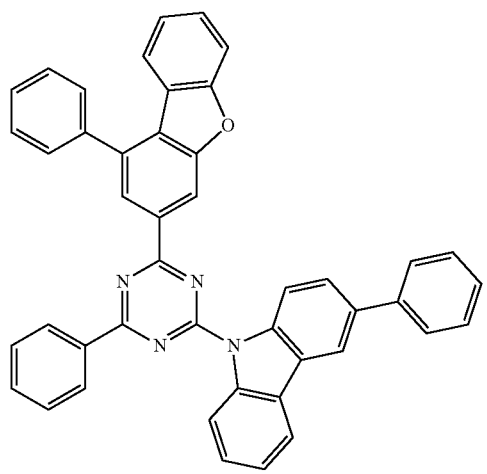
[A-29]
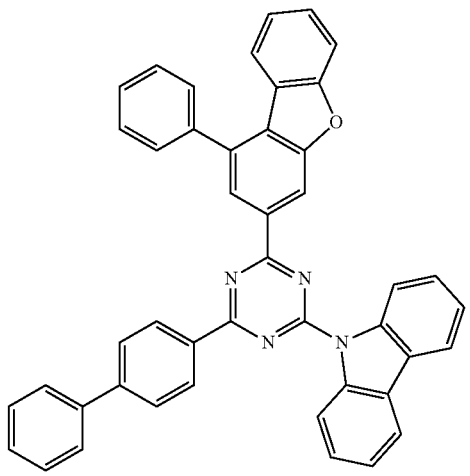
[A-32]
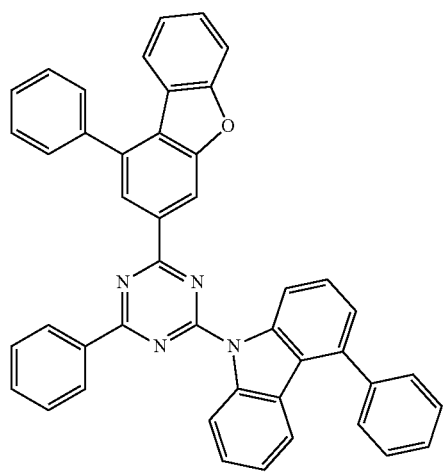
[A-30]
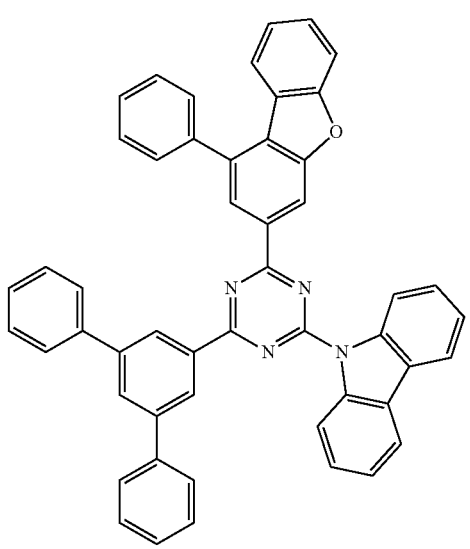
[A-33]
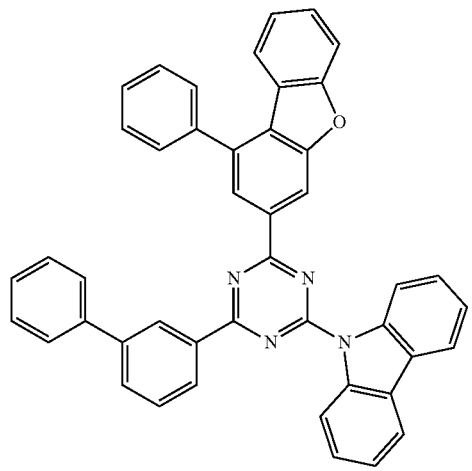
[A-31]
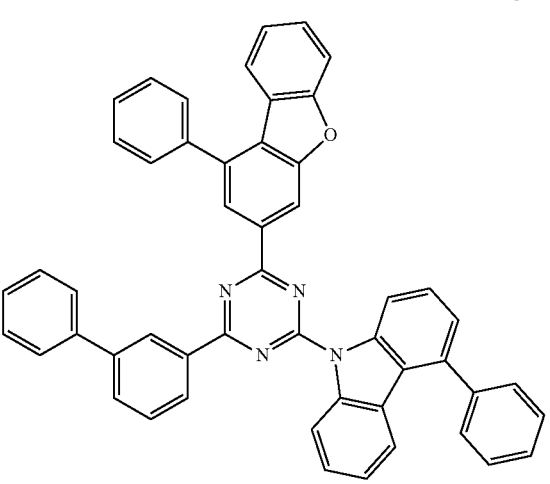
[A-34]

[A-35]
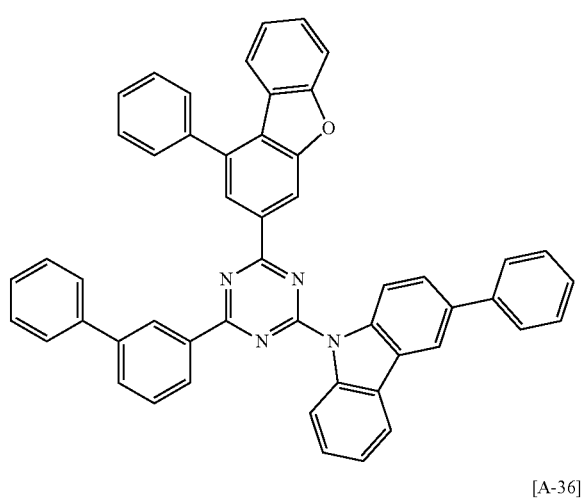
[A-36]
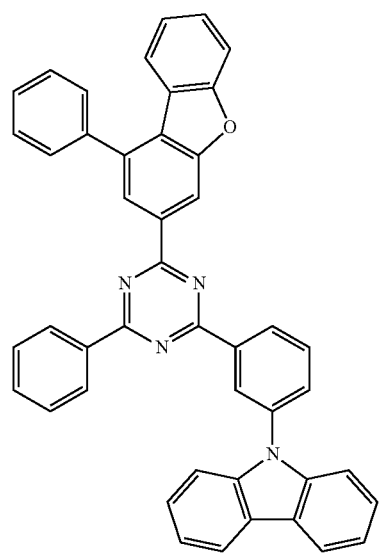
[A-37]
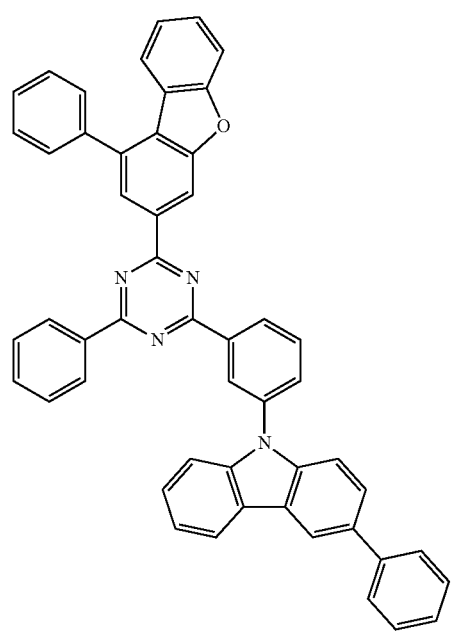
[A-38]
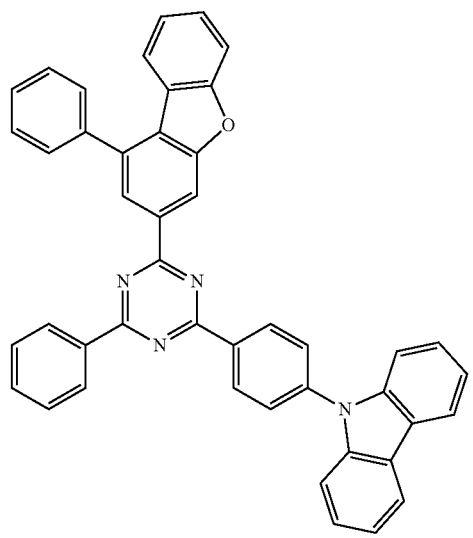
[A-39]
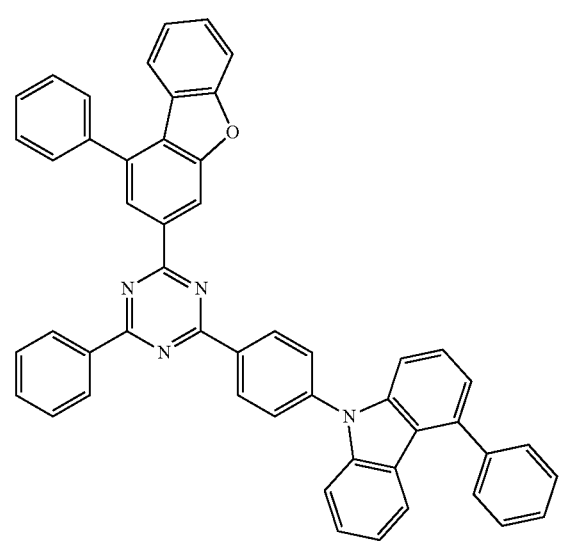
[A-40]
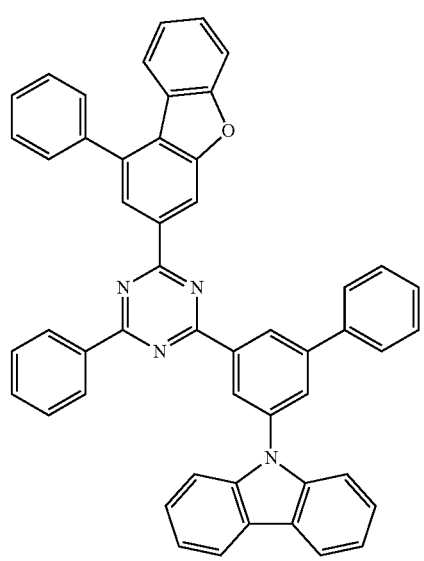

[A-41]
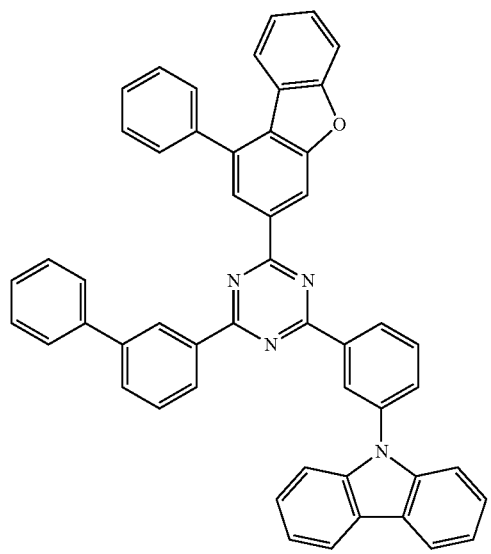
[A-42]
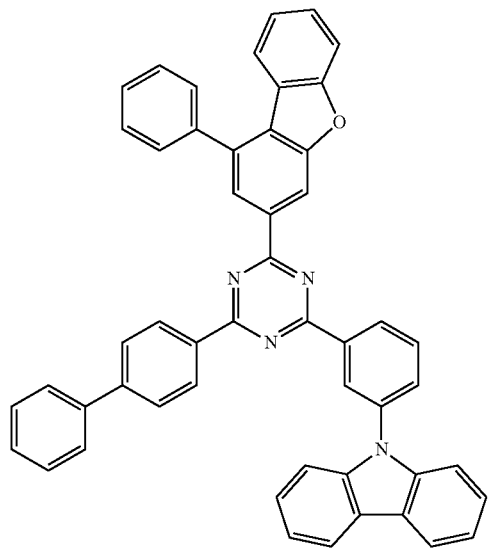
[A-43]
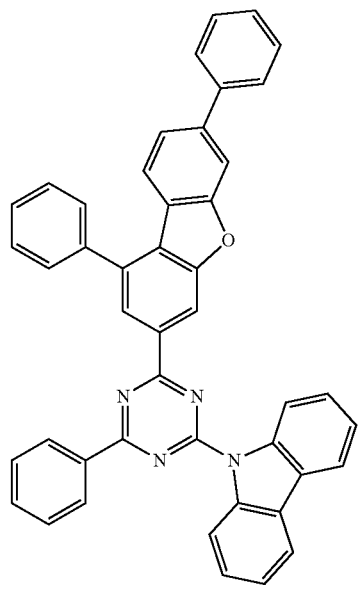
[A-44]
[A-45]
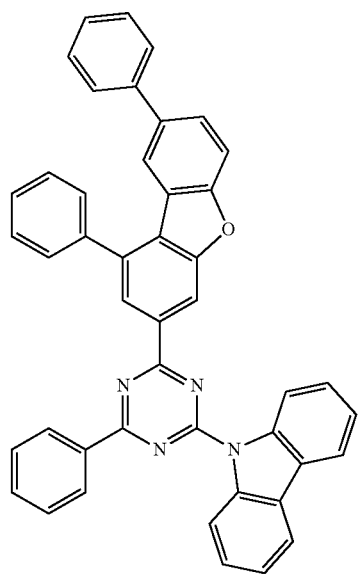

[A-46]
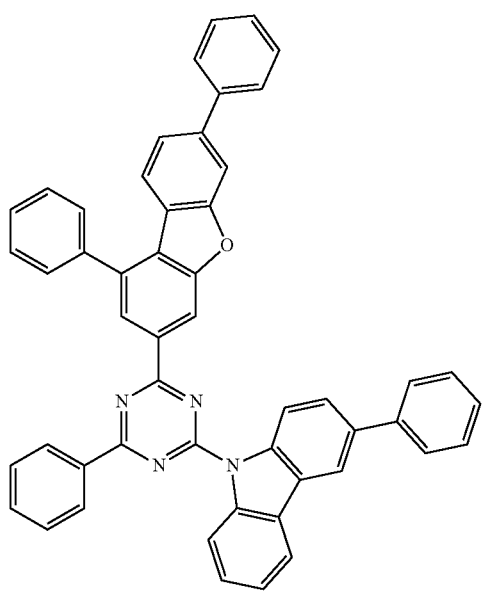
[A-47]
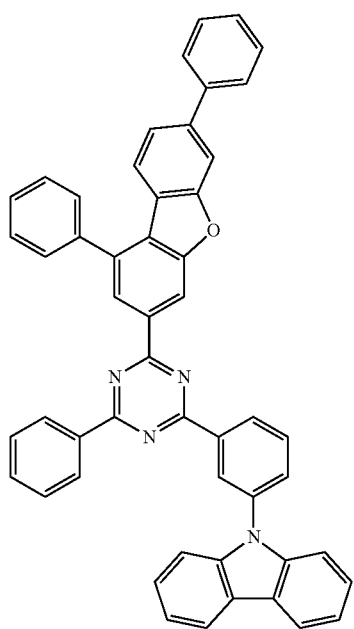
[A-48]
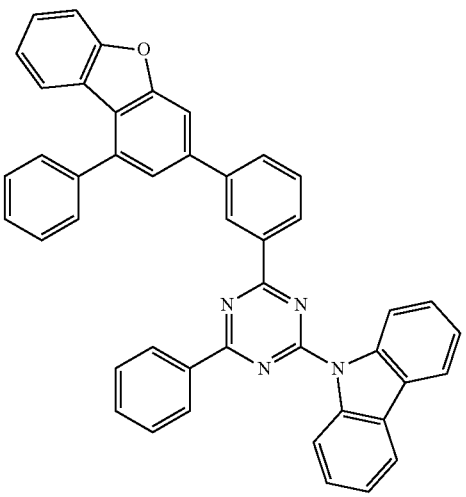
[A-49]
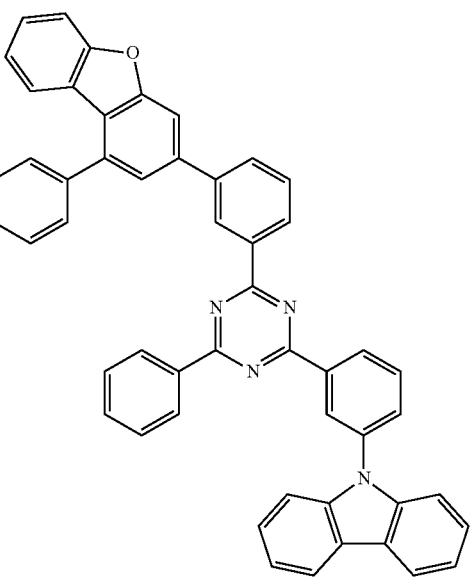
[A-50]
A composition for an organic optoelectronic device according to an example embodiment includes the compound represented by the combination of Chemical Formula 1 and Chemical Formula 2 bonded together (hereinafter, "first compound") and a second compound represented by Chemical Formula 3:

[Chemical Formula 3]

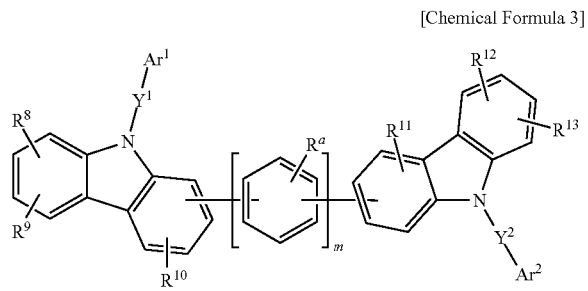

In Chemical Formula 3, $Y^1$ and $Y^2$ may each independently be a single bond or a substituted or unsubstituted C6 to C20 arylene group, $Ar^1$ and $Ar^2$ may each independently be a substituted or unsubstituted C6 to C20 aryl group or a substituted or unsubstituted C2 to C30 heterocyclic group, $R^c$ and $R^8$ to $R^{13}$ may each independently be hydrogen, deuterium, a substituted or unsubstituted C1 to C10 alkyl group, a substituted or unsubstituted C6 to C20 aryl group, a substituted or unsubstituted C2 to C30 heterocyclic group, a cyano group, or a combination thereof, and m may be 0, 1, or 2.

Without being bound by theory, it is believed that the second compound provides fast and stable hole transfer characteristics and, used in a light emitting layer together with the first compound having fast and stable electron transfer characteristics, may provide a charge balance, and may have a desirable glass transition temperature relative to a molecular weight, to provide low driving voltage and long life-span characteristics.

In an example embodiment, $Ar^1$ and $Ar^2$ of Chemical Formula 3 may each independently be a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted triphenylenyl group, a substituted or unsubstituted carbazolyl group, a substituted or unsubstituted dibenzothiophenyl group, a substituted or unsubstituted dibenzofuranyl group, a substituted or unsubstituted fluorenyl group, or a substituted or unsubstituted pyridinyl group, $Y^1$ and $Y^2$ may each independently be a single bond, a substituted or unsubstituted phenylene group, or a substituted or unsubstituted biphenylene group, $R^c$ and $R^8$ to $R^{13}$ may each independently be hydrogen, deuterium, or a substituted or unsubstituted C6 to C12 aryl group, and m may be 0 or 1.

The "substituted" of Chemical Formula 3 may refer to replacement of at least one hydrogen by deuterium, a C1 to C4 alkyl group, a C6 to C18 aryl group, or a C2 to C30 heteroaryl group.

For example, Chemical Formula 3 may be represented by Chemical Formula 3A.

[Chemical Formula 3A]

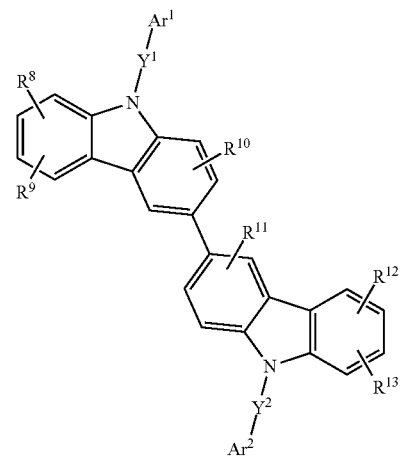

In Chemical Formula 3A, $Y^1$, $Y^2$, $Ar^1$, $Ar^2$ and $R^8$ to $R^{13}$ are the same as described above.

In an example embodiment, Chemical Formula 3 may be one of structures of Group II and —$Y^1$—$Ar^1$ and *—$Y^2$—$Ar^2$ may be one of substituents of Group III.

[Group II]

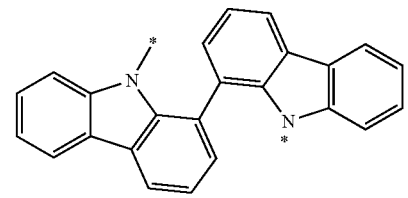
C-1

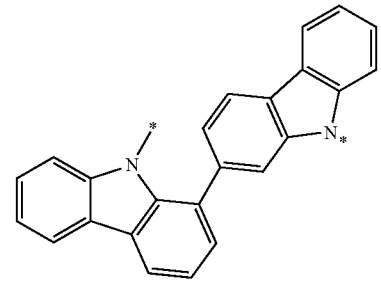
C-2

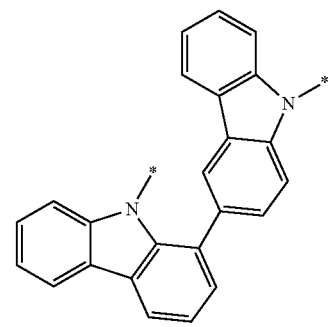
C-3

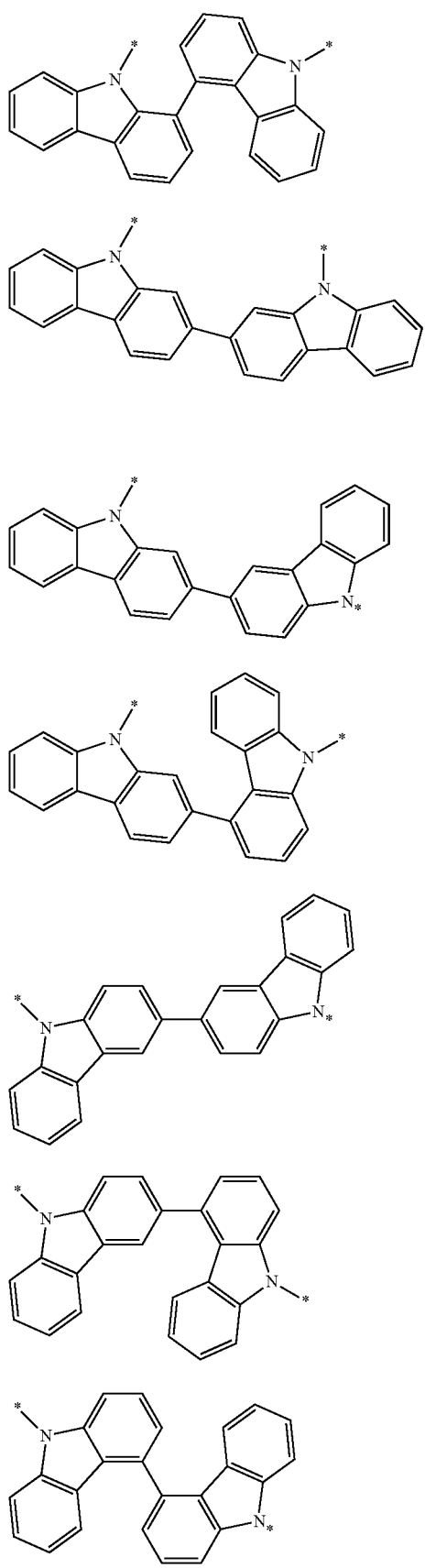
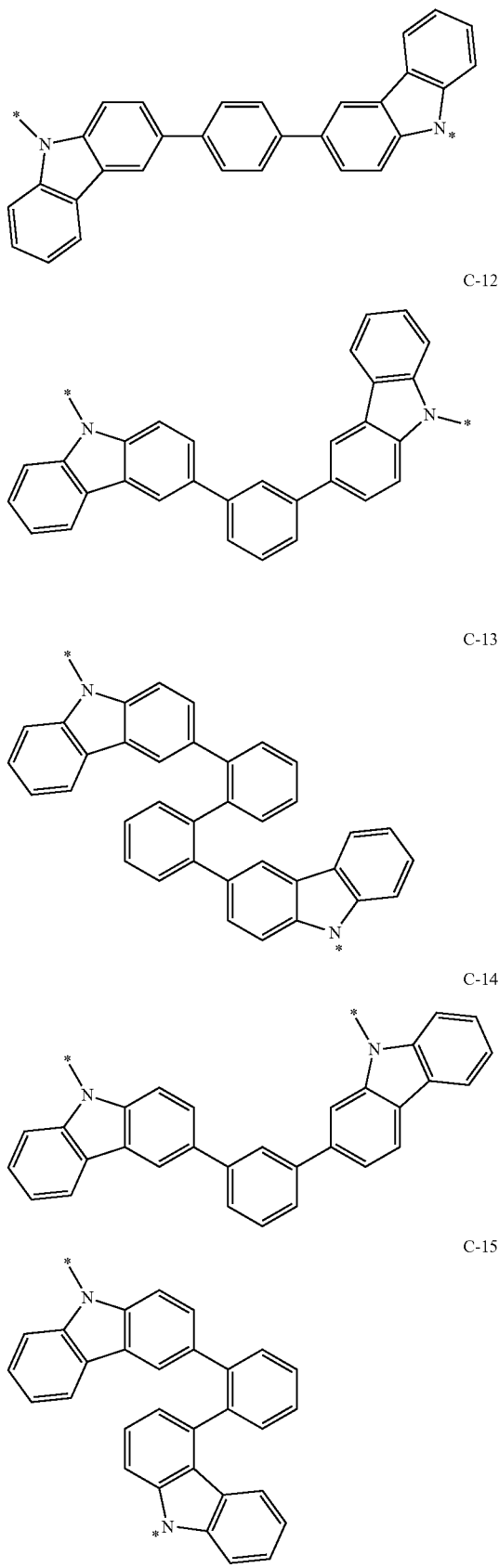

C-16
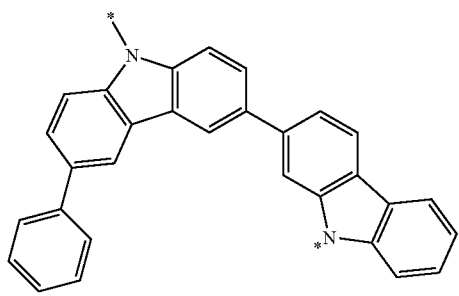
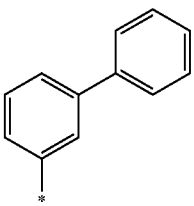
B-3
C-17
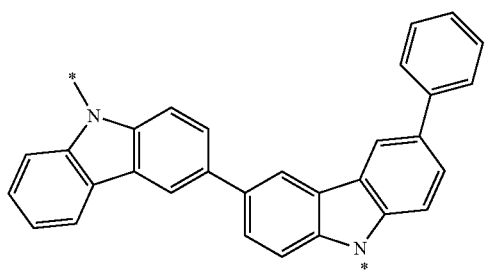
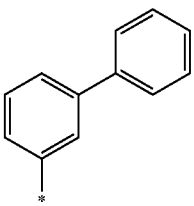
B-4
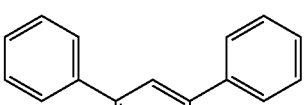
B-5
C-18
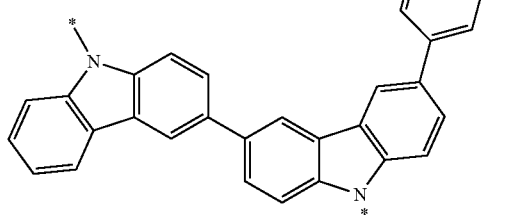
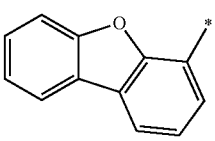
B-6
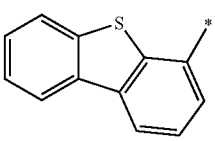
B-7
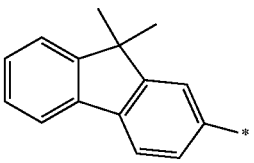
B-8
[Group III]
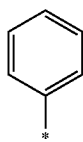
B-1
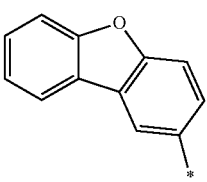
B-9
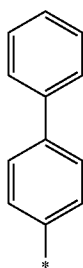
B-2
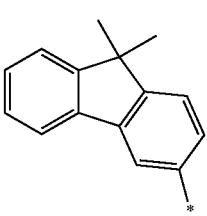
B-10

B-11 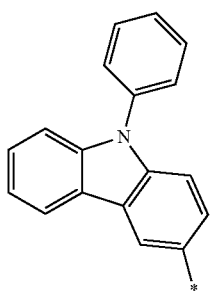
B-12 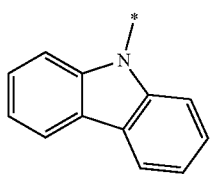
B-13 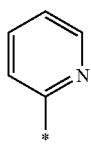
B-14 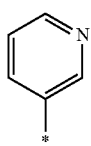
B-15 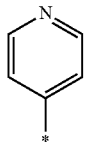
B-16 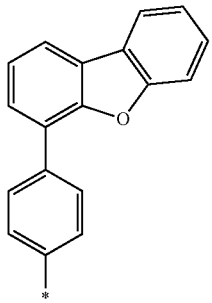
B-17 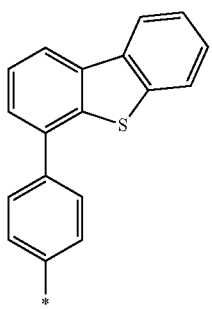
B-18 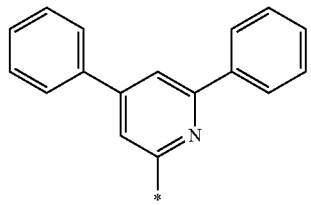
B-19 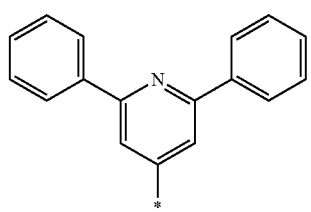
B-20 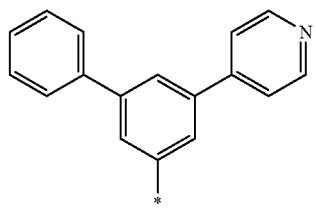
B-21 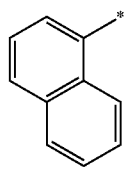
B-22 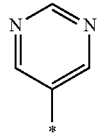
B-23 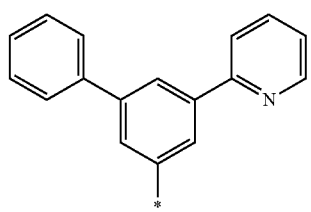
B-24 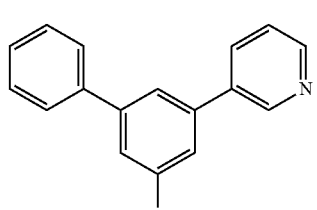
B-25

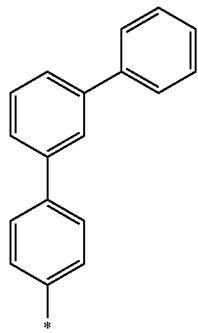
B-26

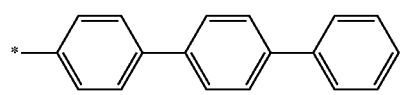
B-27

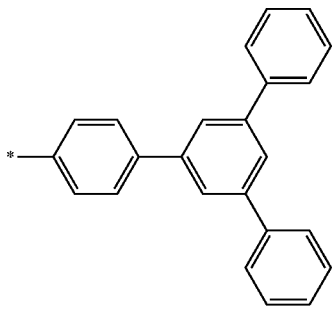
B-28

In Group II and Group III, * is a linking point.

In a more specific example embodiment, Chemical Formula 3 may be represented by Chemical Formula C-8 or Chemical Formula C-17 of Group II and *—$Y^1$—$Ar^1$ and *—$Y^2$—$Ar^2$ may be one of Group III.

In an example embodiment, the compound represented by Chemical Formula 3 may be one of compounds of Group 2, but is not limited thereto.

[Group 2]

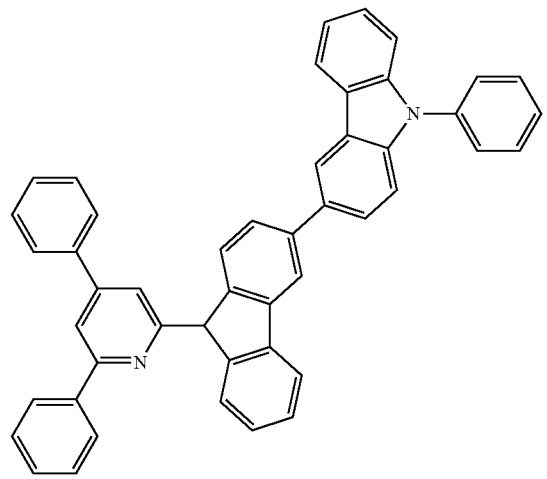
[B-1]

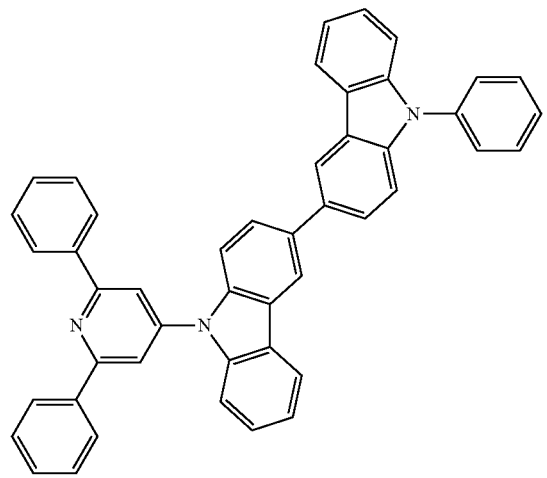
[B-2]

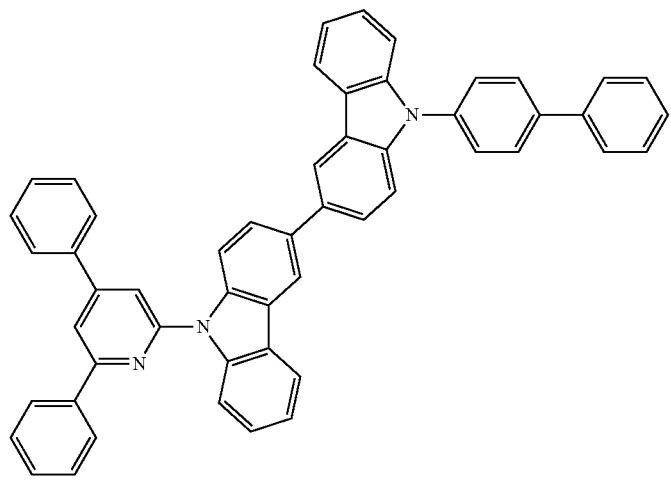
[B-3]
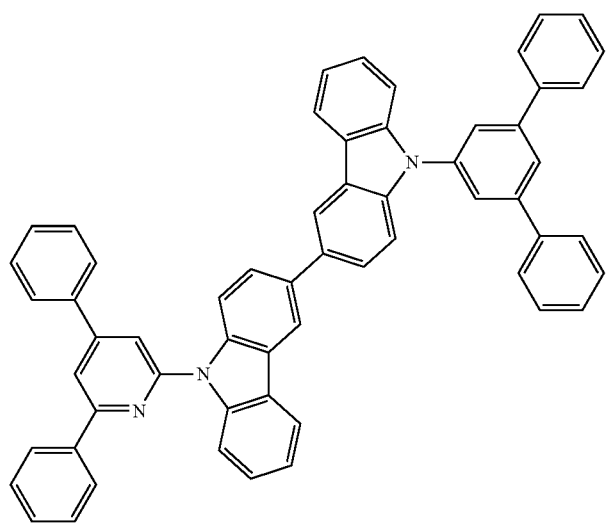
[B-4]
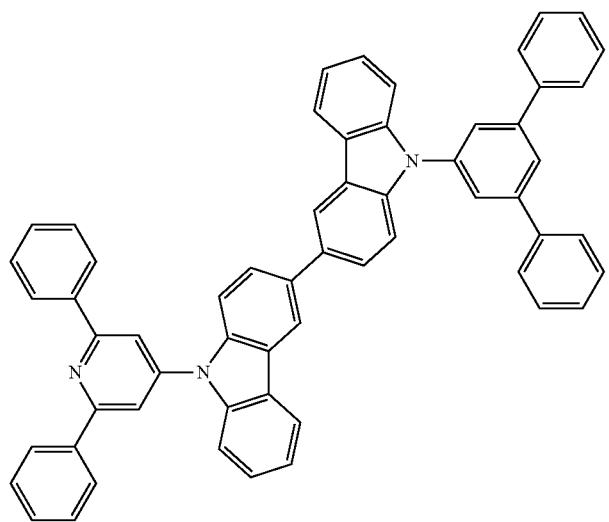
[B-5]

[B-6]
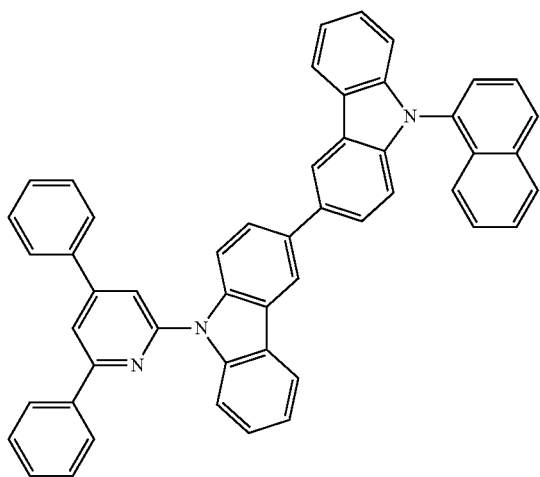
[B-7]
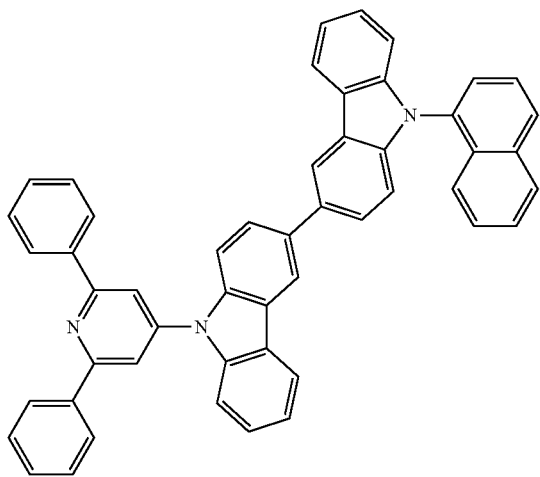
[B-8]
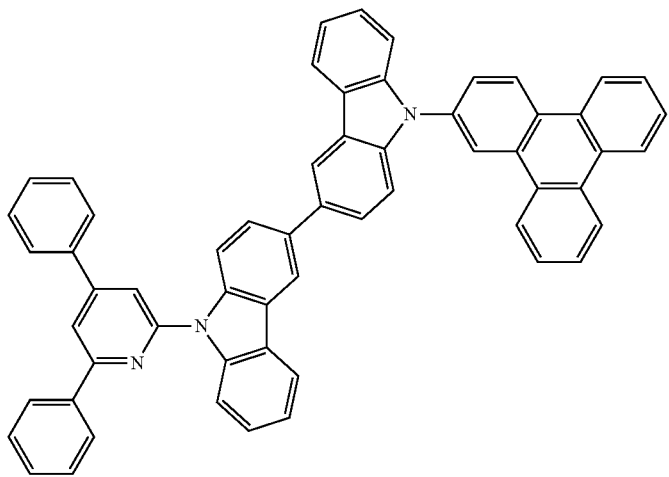

[B-9]
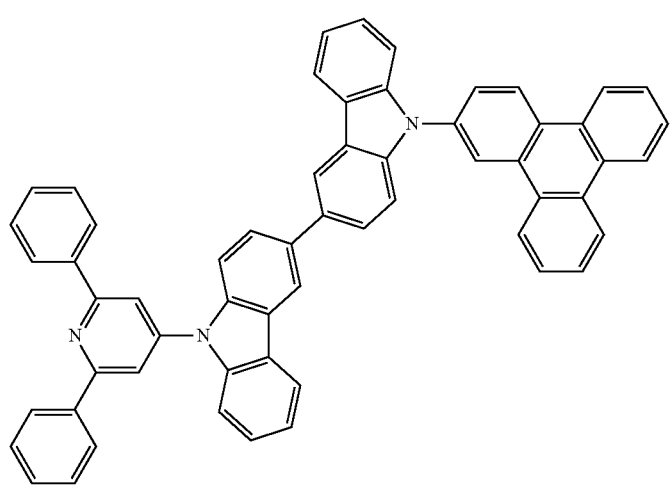
[B-10]
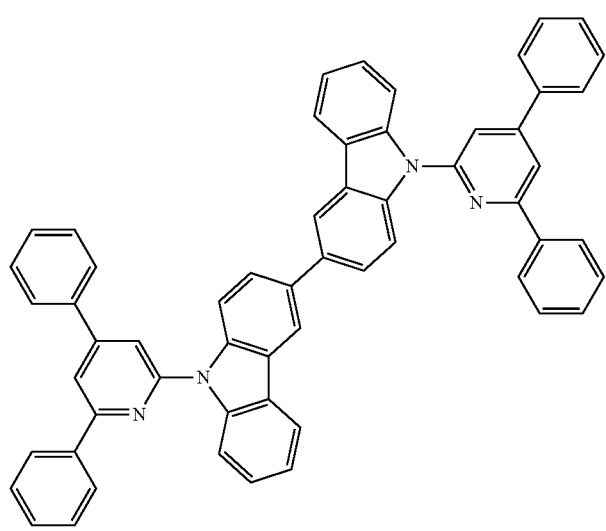
[B-11]
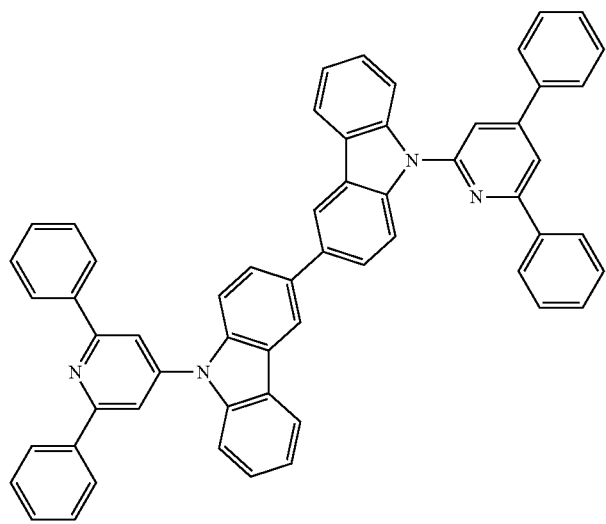

[B-12]
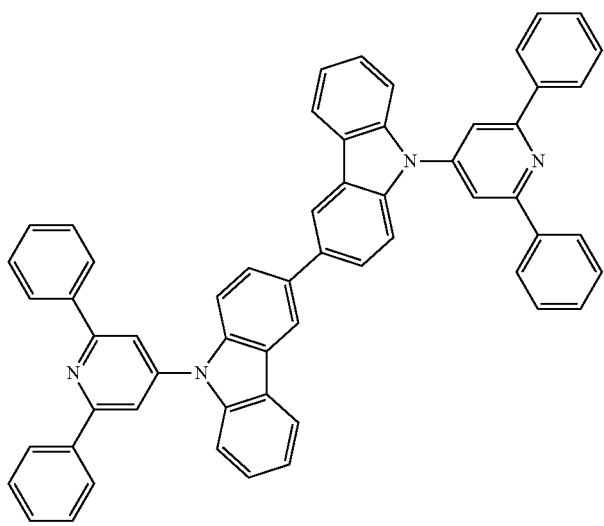
[B-13]
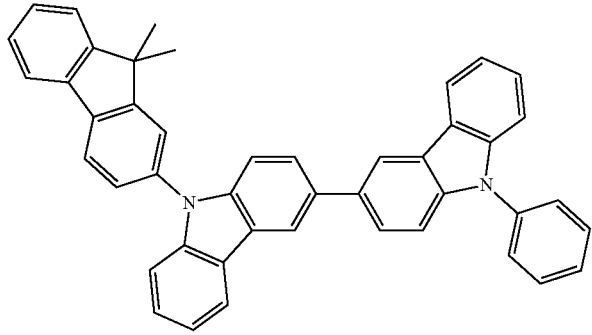
[B-14]
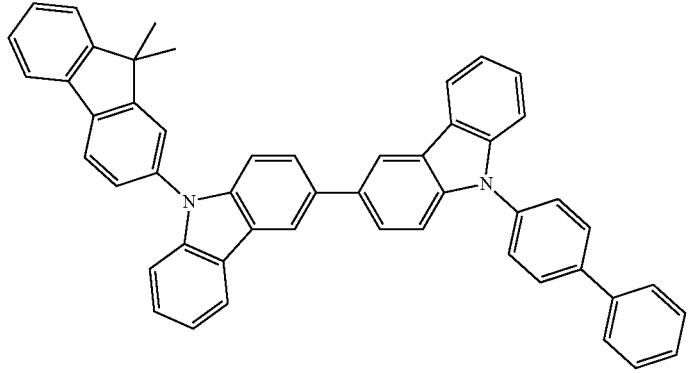
[B-15]
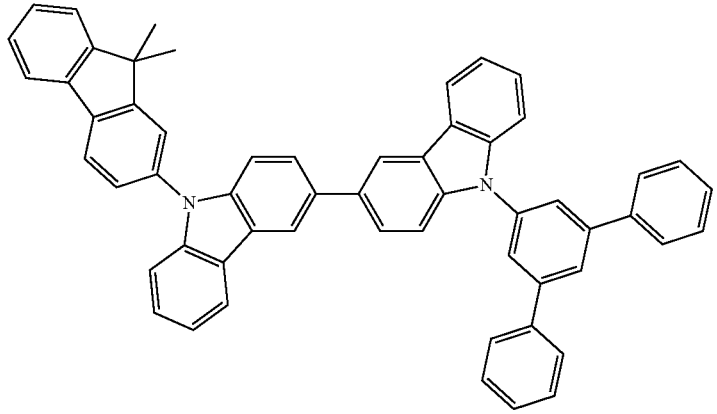

[B-16]
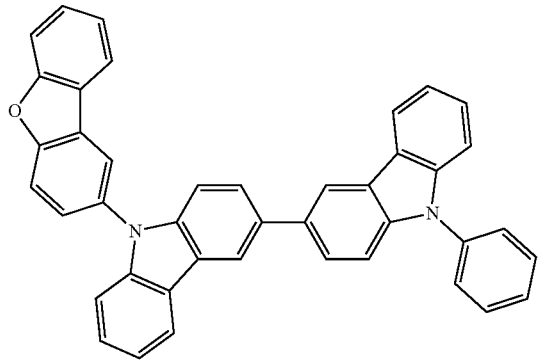
[B-17]
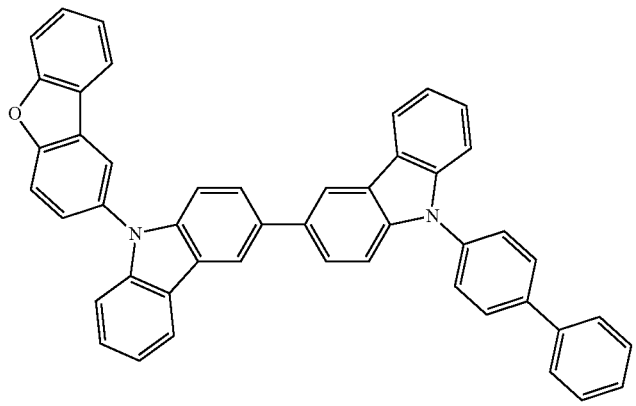
[B-18]
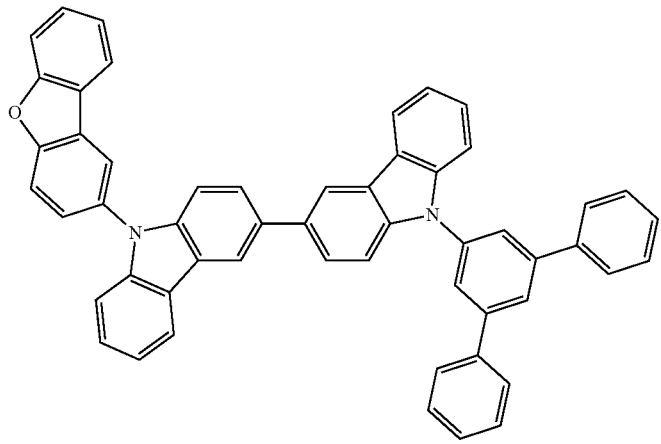
[B-19]
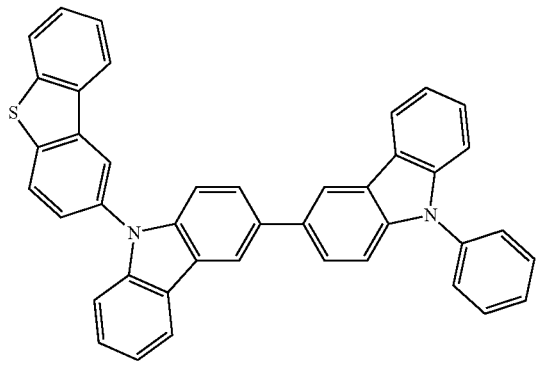

[B-20]
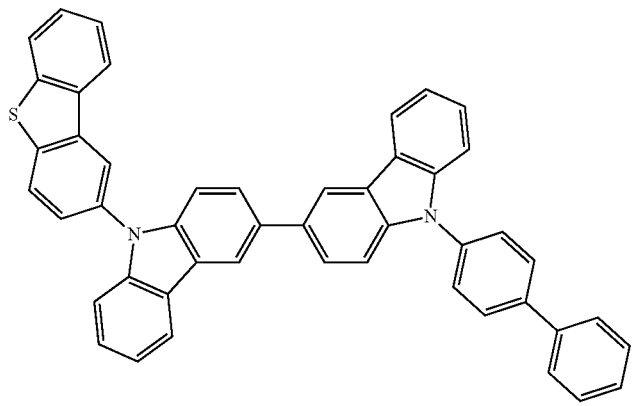
[B-21]
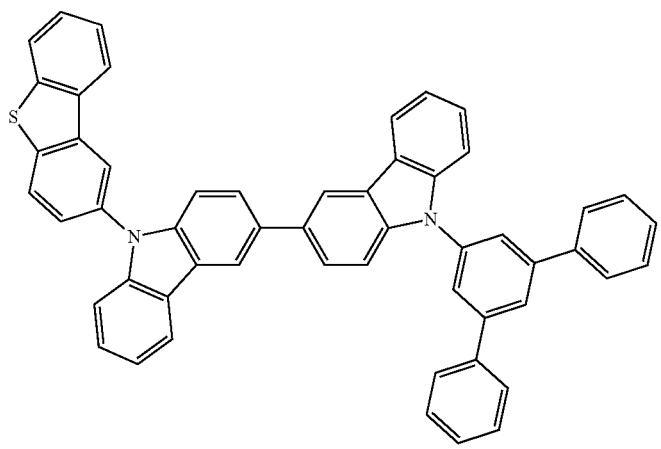
[B-22]
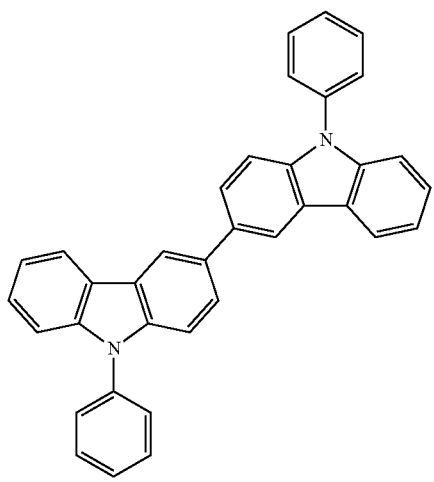

-continued
[B-23]
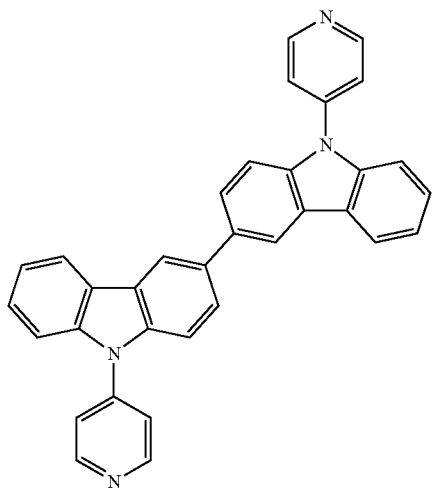
[B-24]
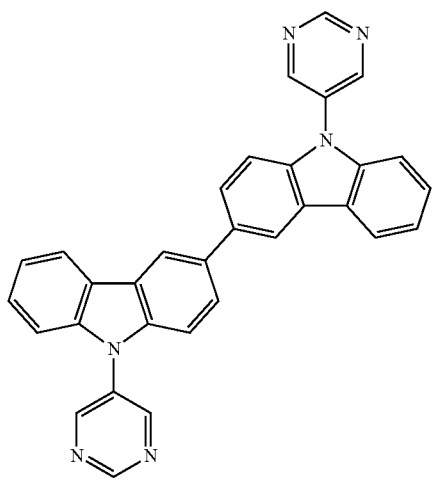
[B-25]
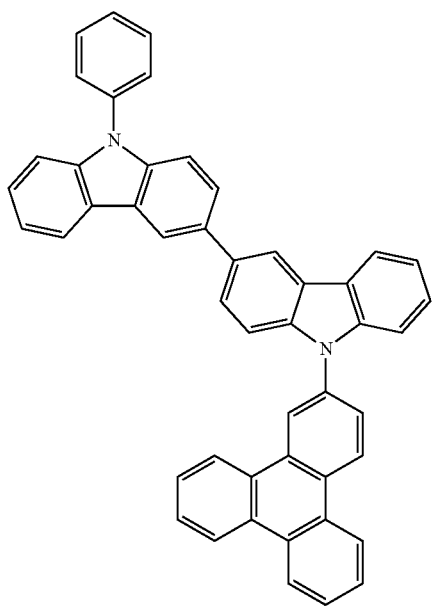

[B-26]
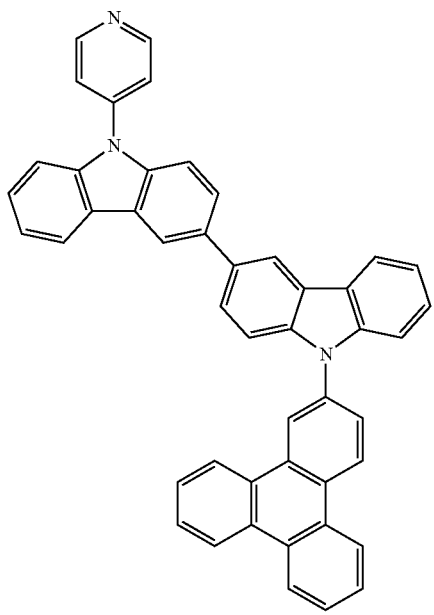
[B-27]
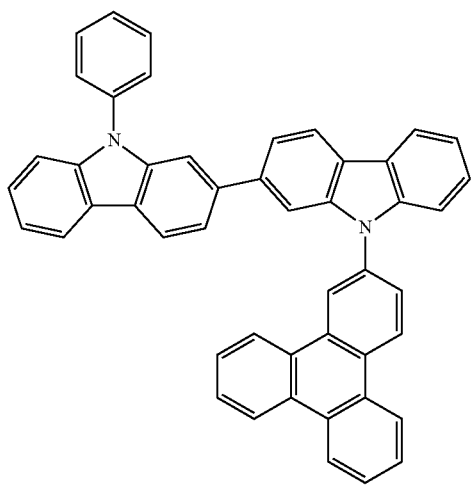
[B-28]
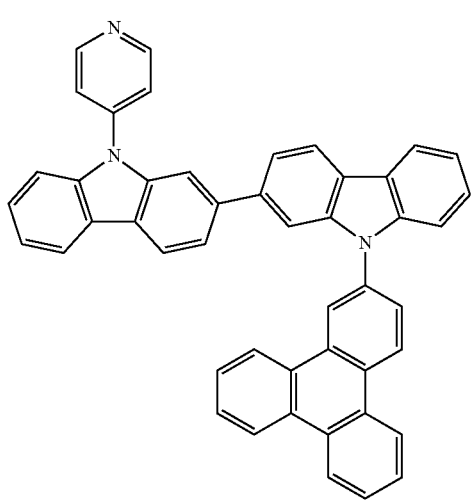

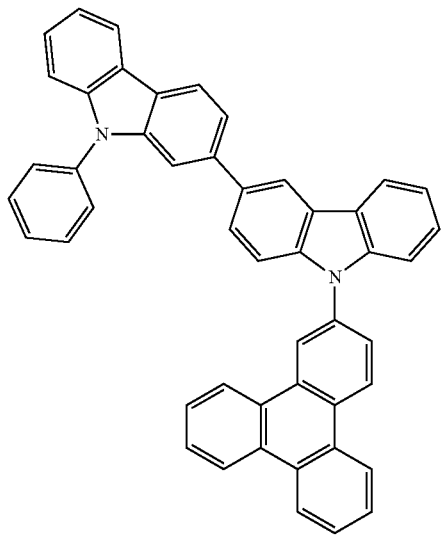
[B-29]
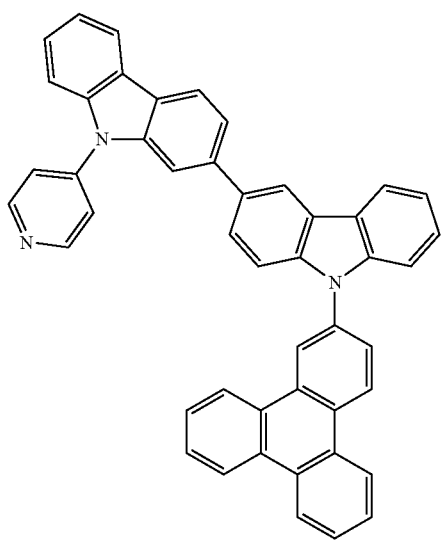
[B-30]

[B-31]
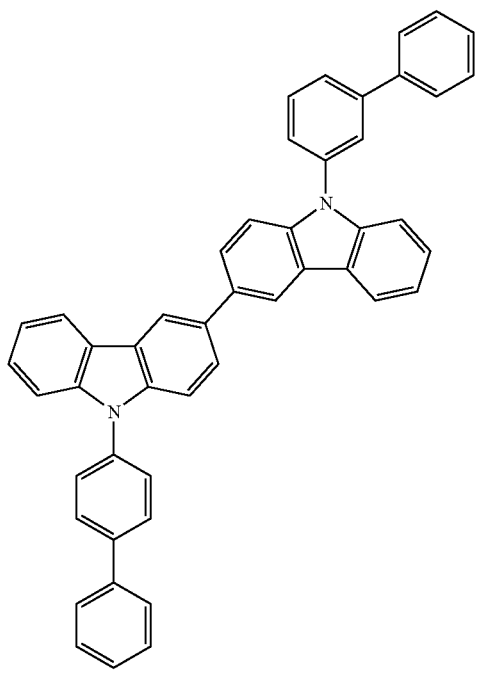
[B-32]
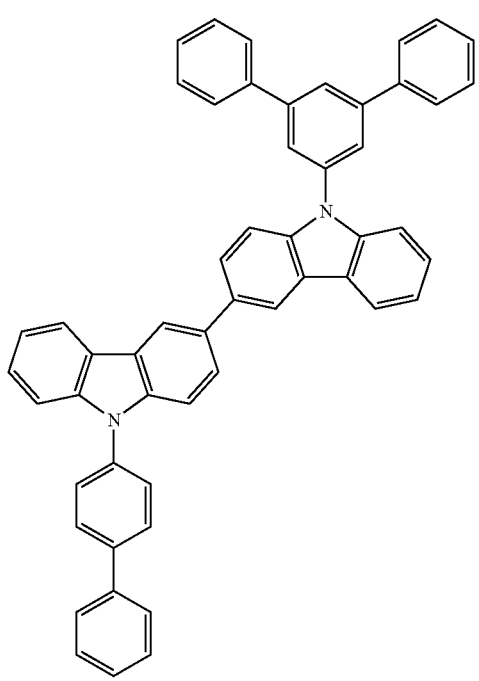

[B-33]
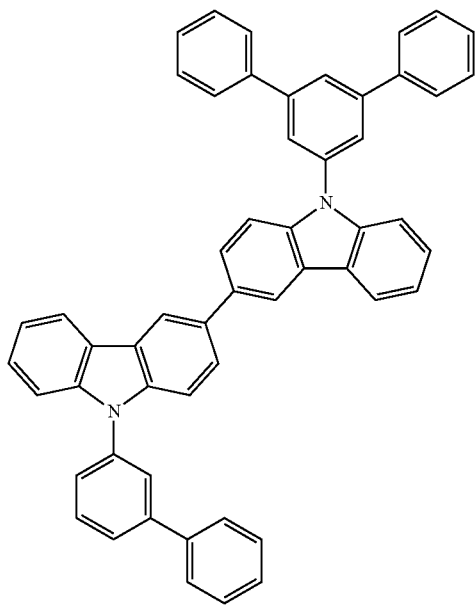
[B-34]
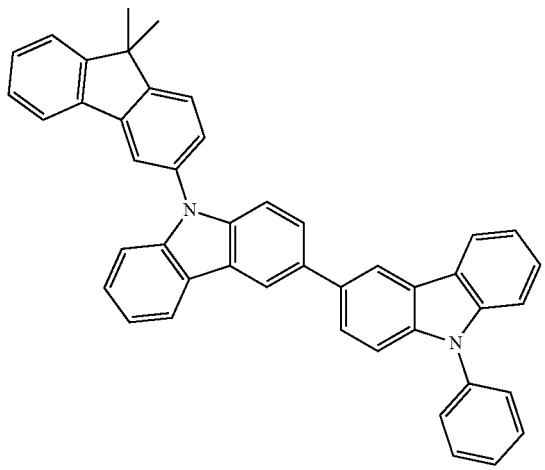
[B-35]
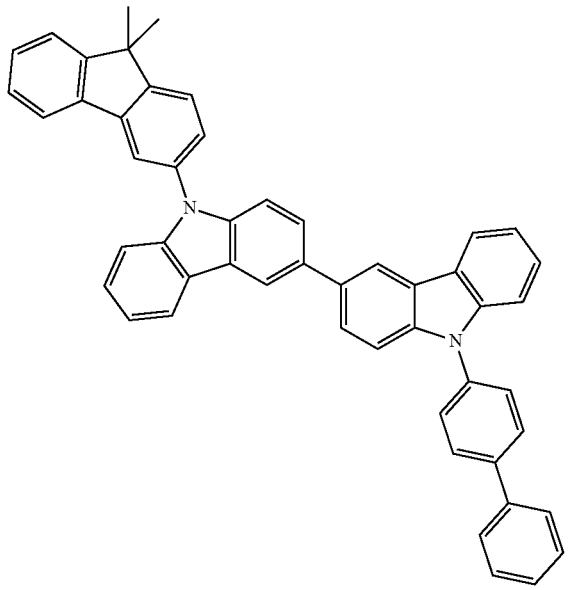

[B-36]
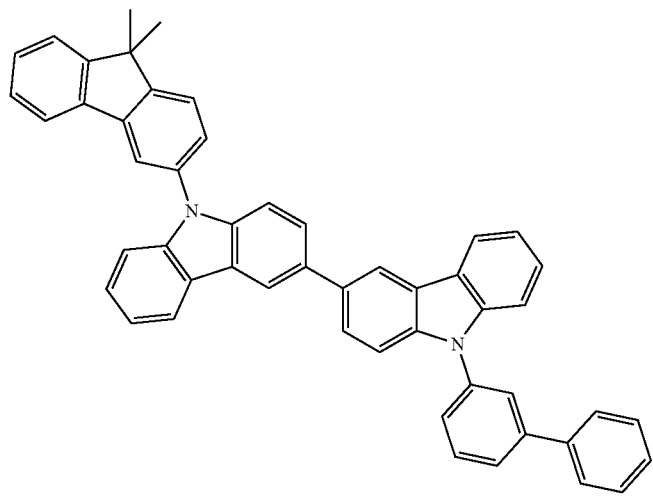
[B-37]
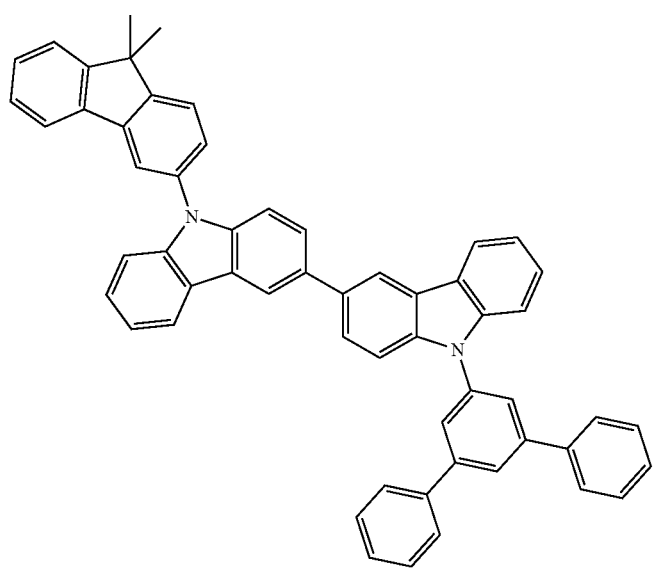
[B-38]
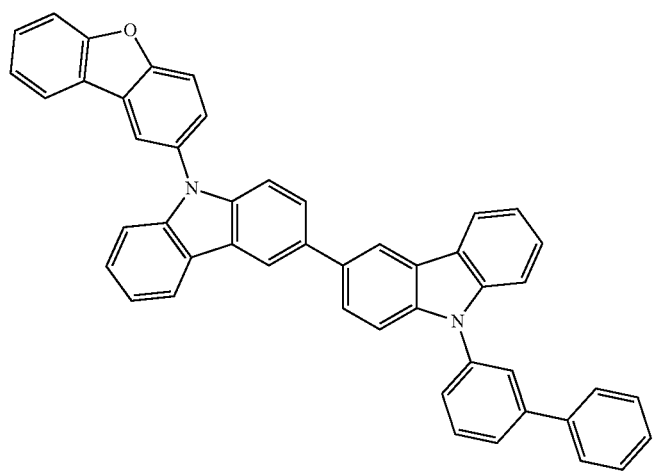

[B-39]
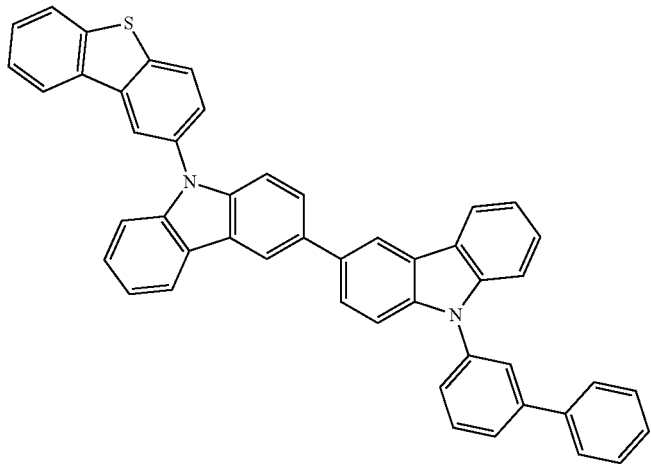
[B-40]
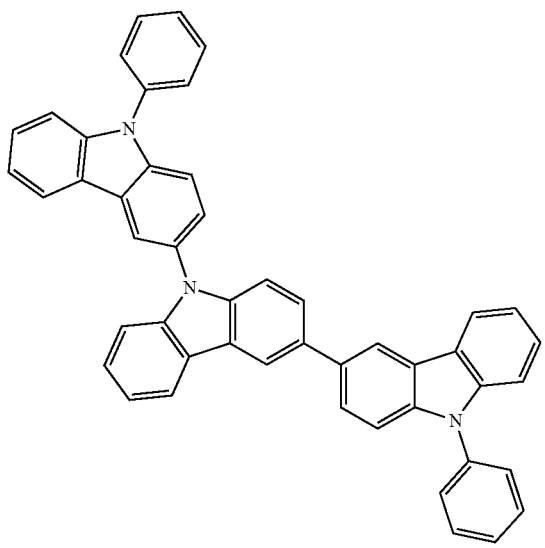
[B-41]
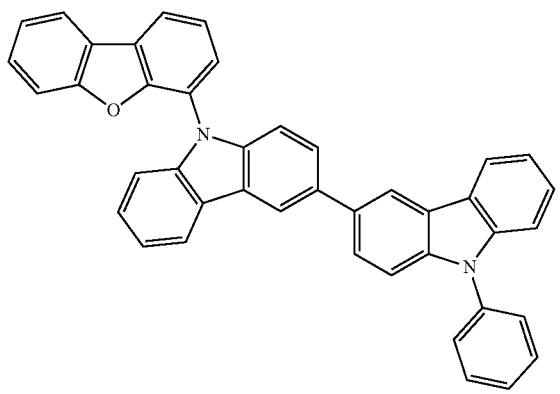

[B-42]
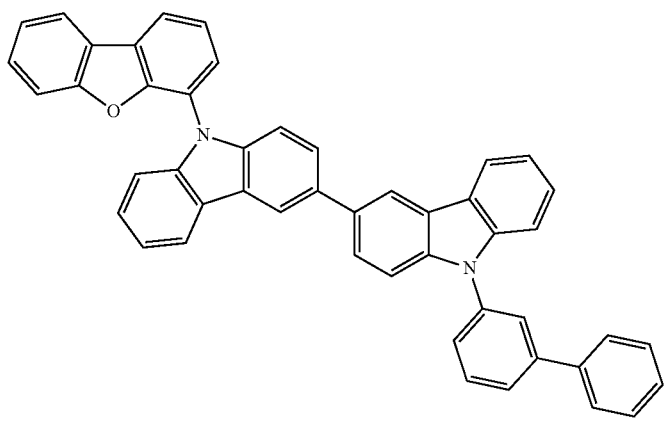
[B-43]
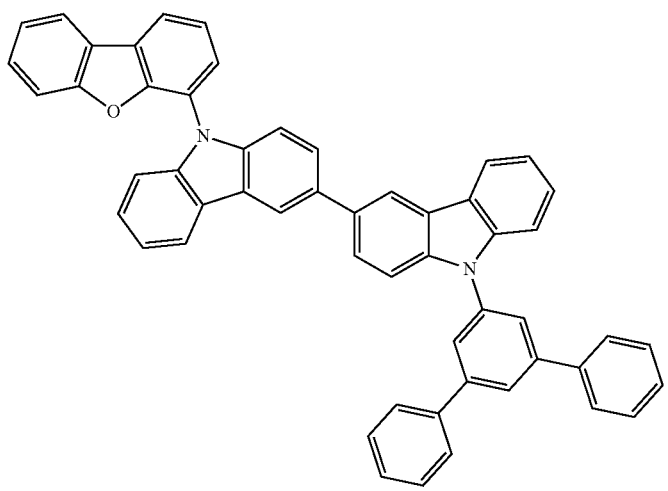
[B-44]
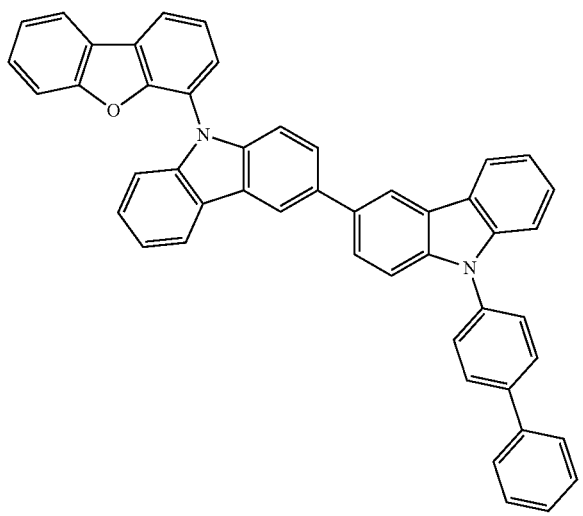

[B-45]
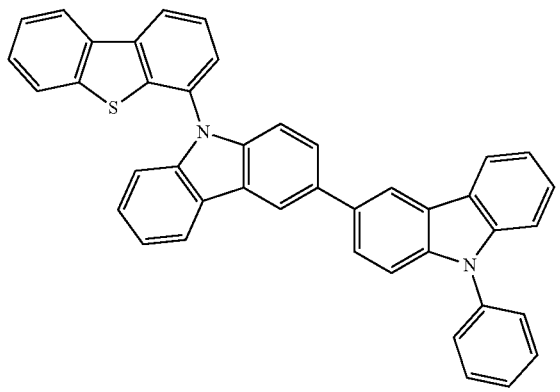
[B-46]
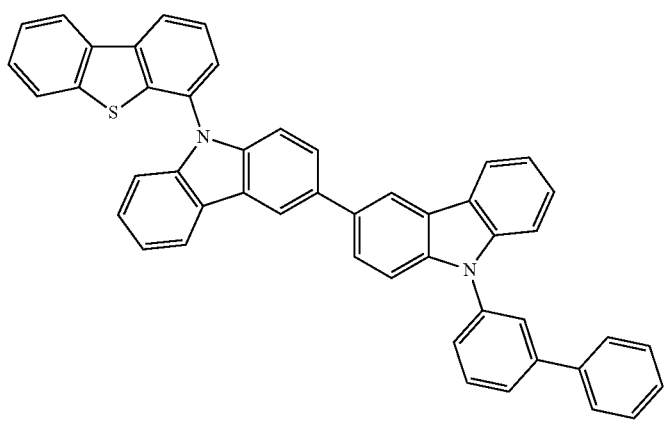
[B-47]
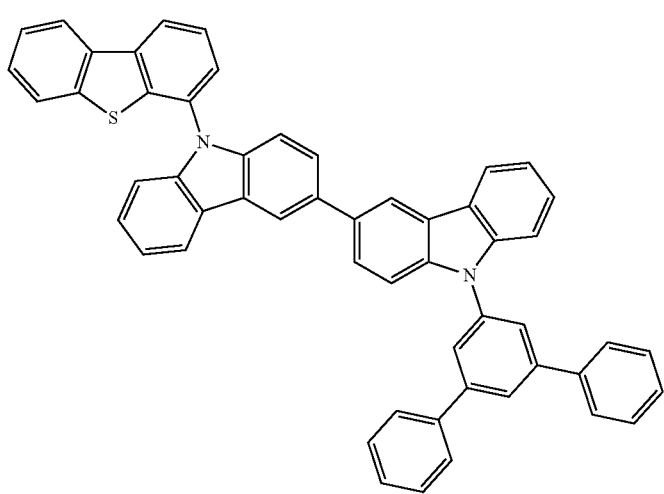

[B-48]
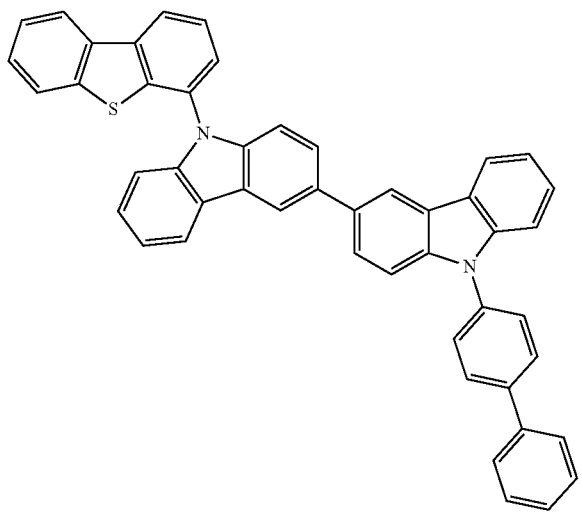
[B-49]
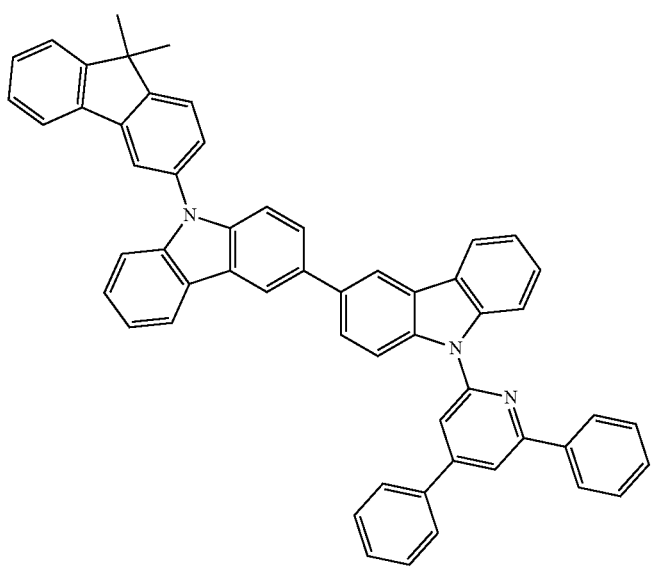
[B-50]
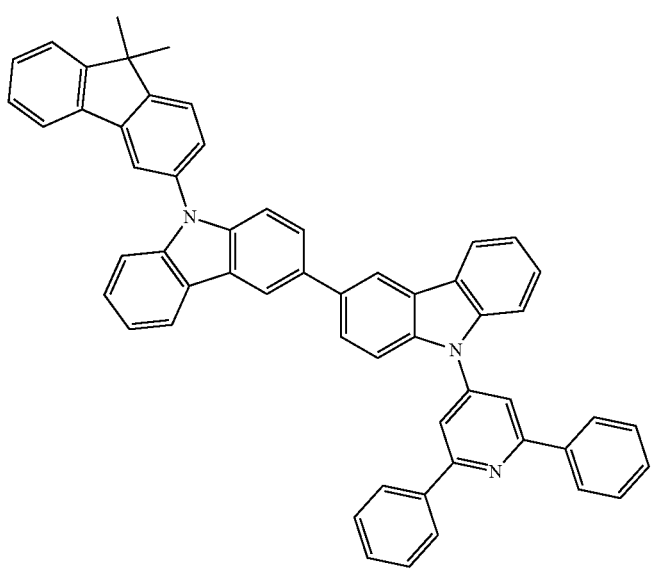

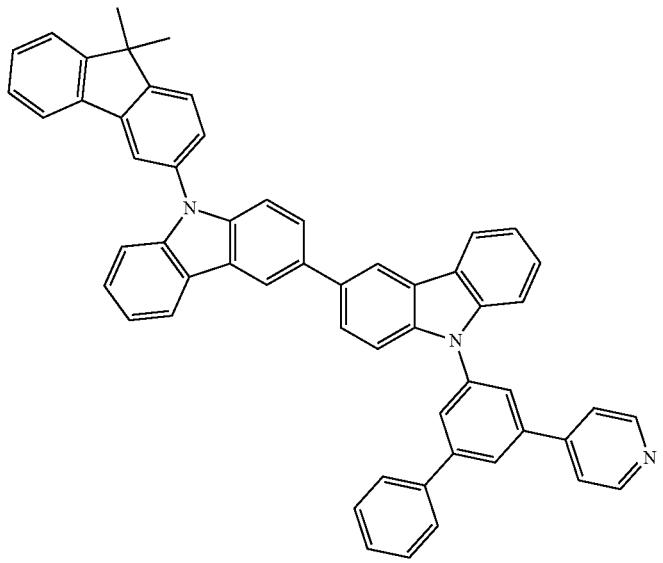
[B-51]
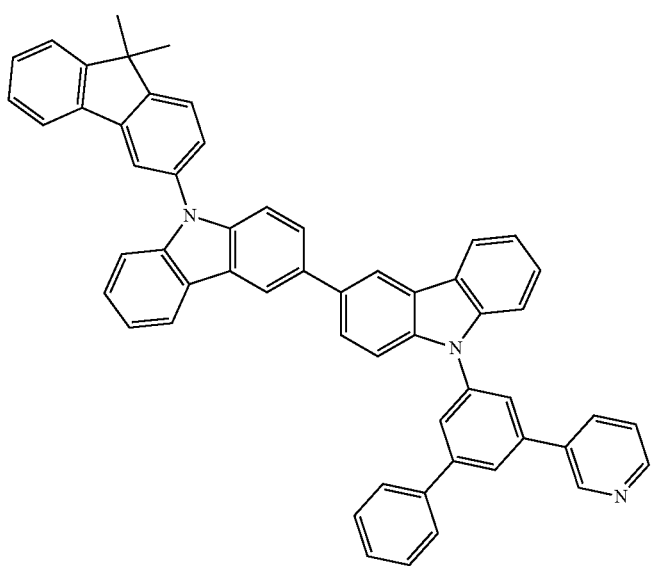
[B-52]

[B-53]
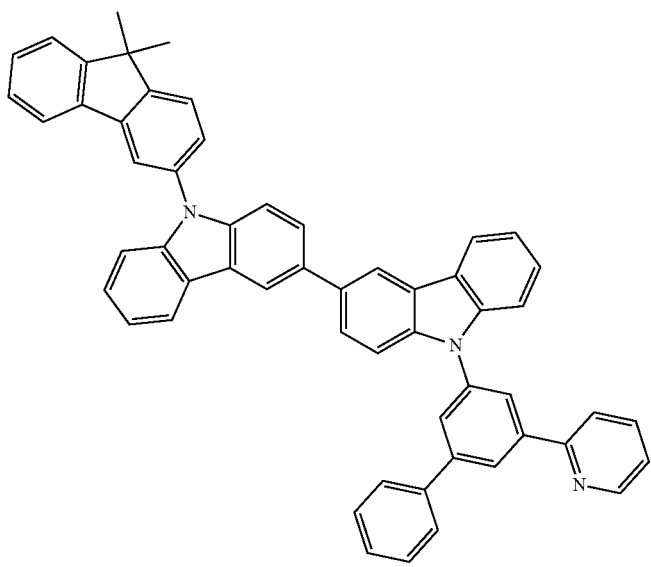
[B-54]
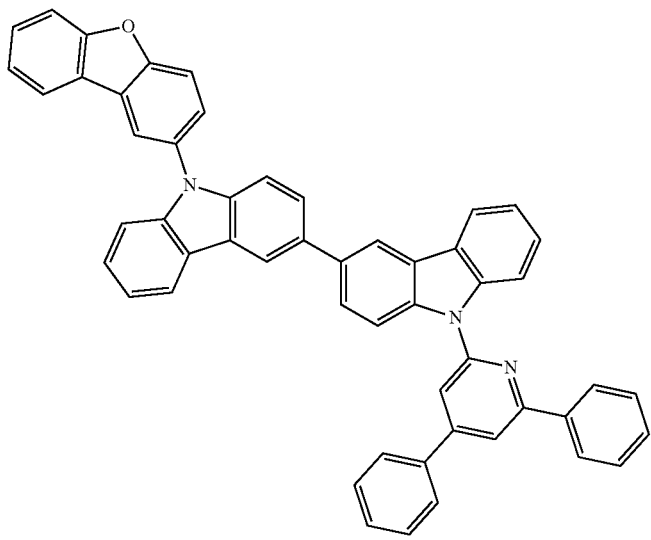
[B-55]
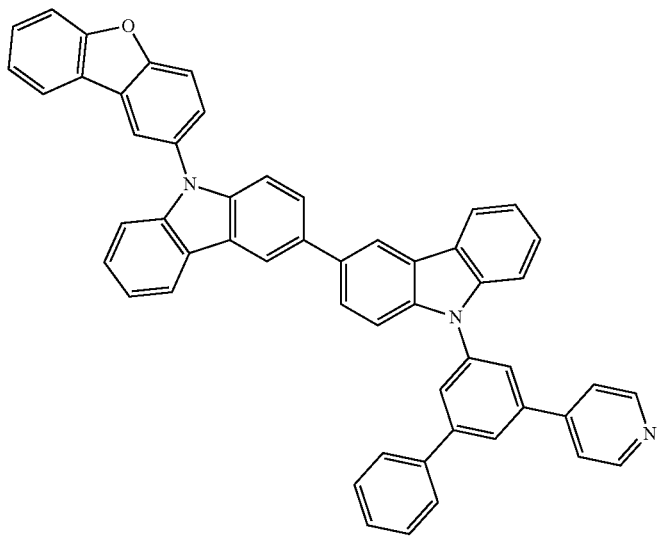

[B-56]
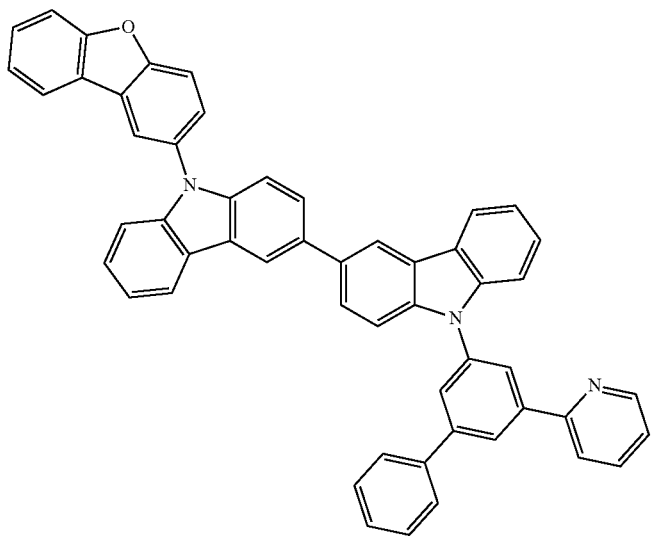
[B-57]
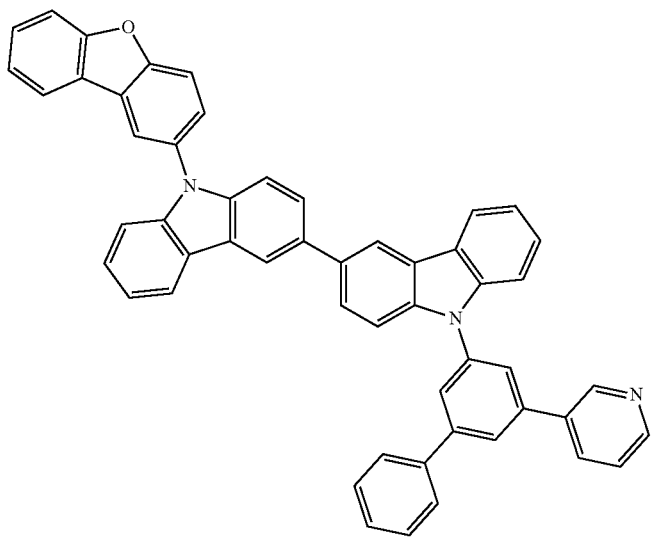
[B-58]
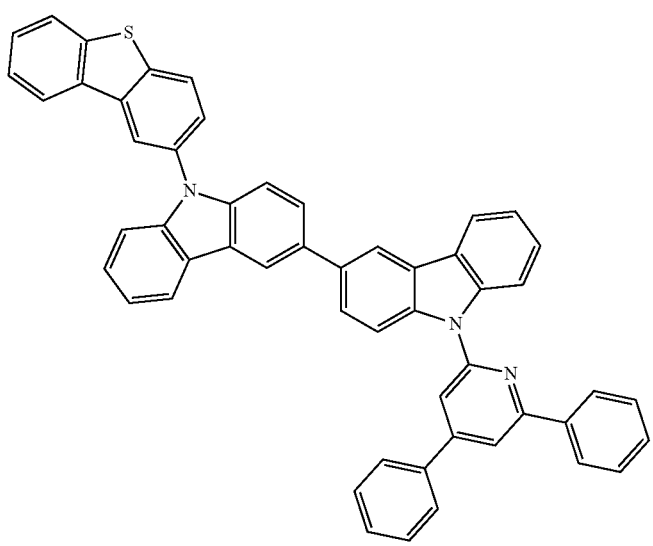

[B-59]
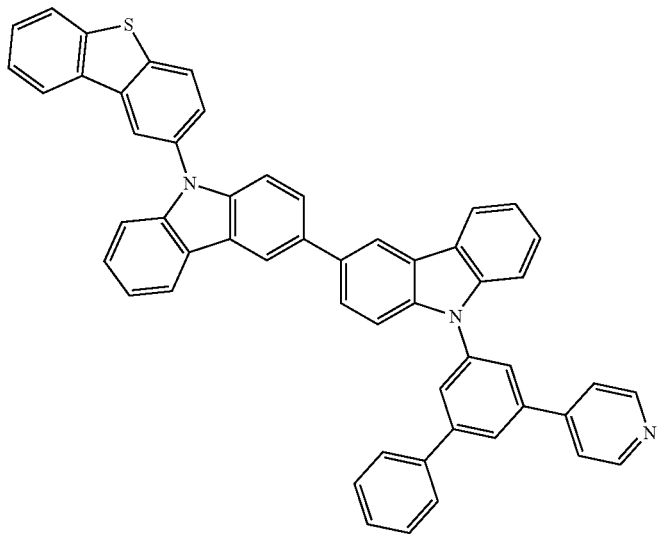
[B-60]
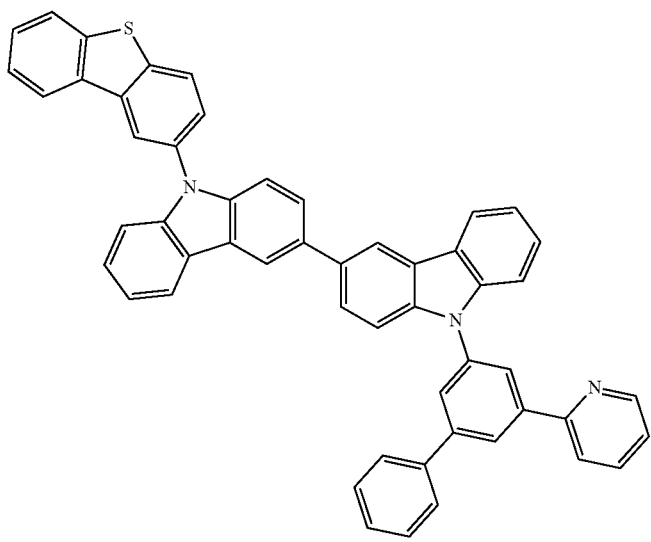
[B-61]
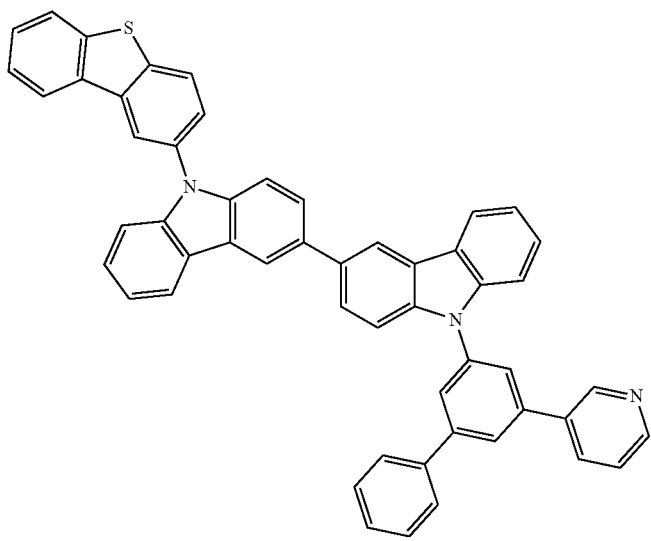

-continued
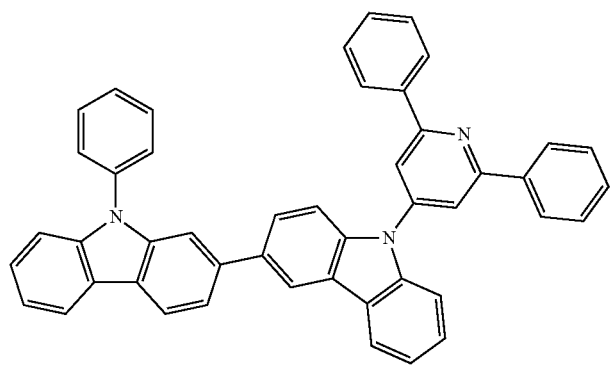
[B-62]
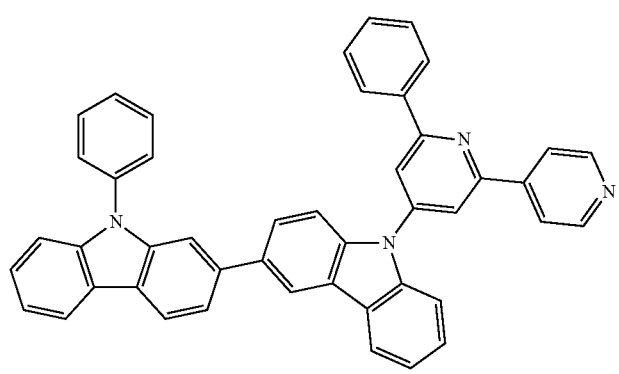
[B-63]
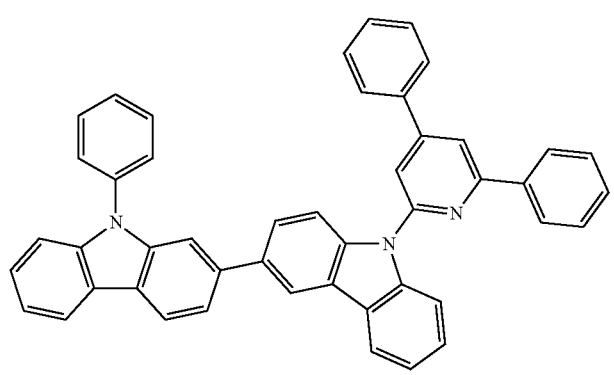
[B-64]
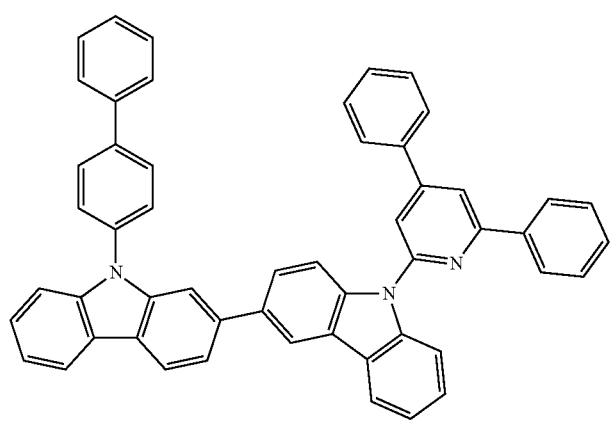
[B-65]

[B-66]
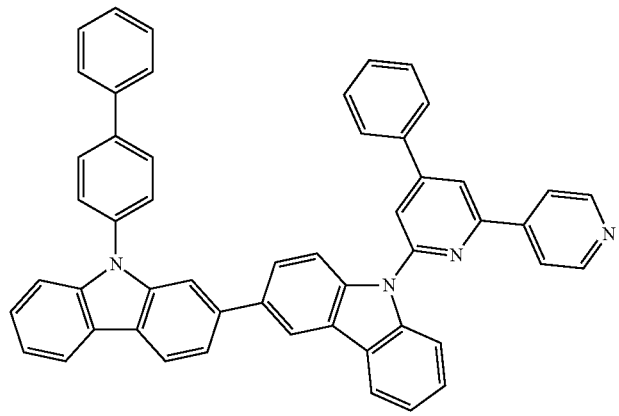
[B-67]
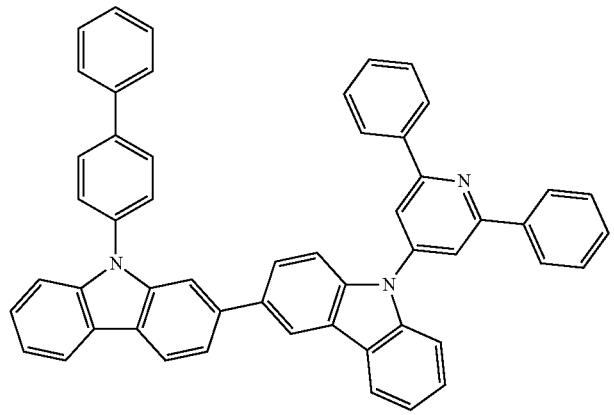
[B-68]
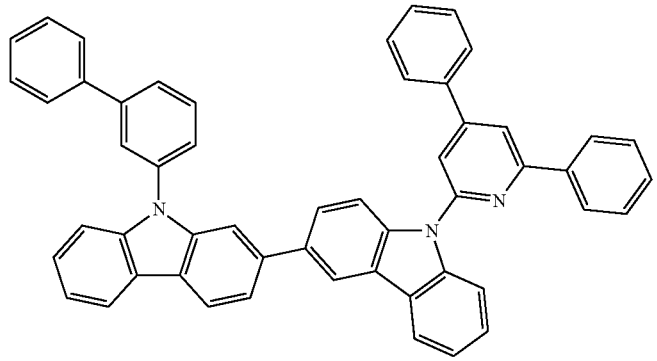
[B-69]
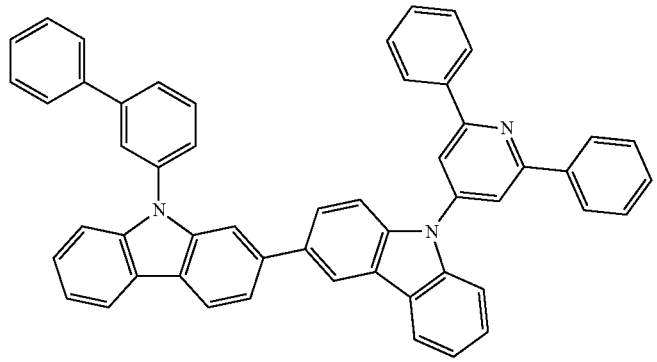

[B-70]
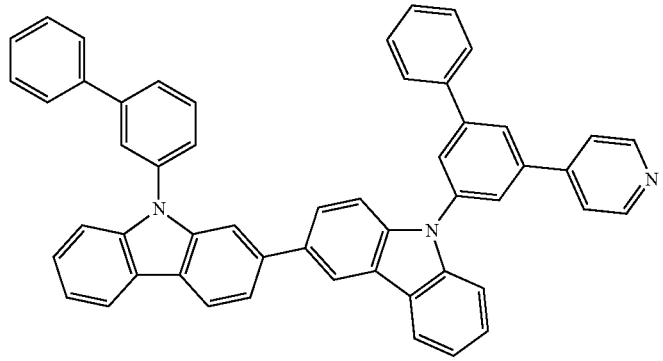
[B-71]
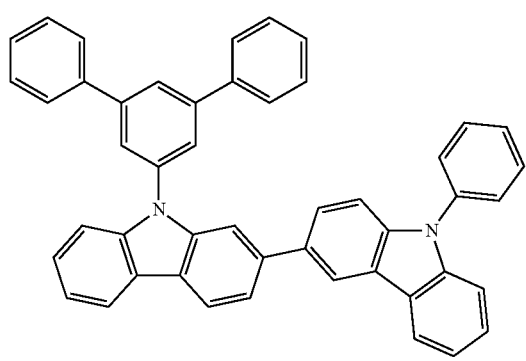
[B-72]
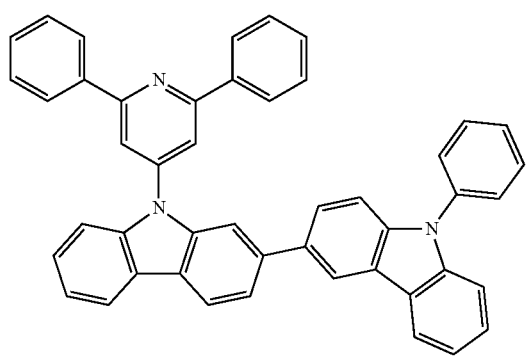
[B-73]
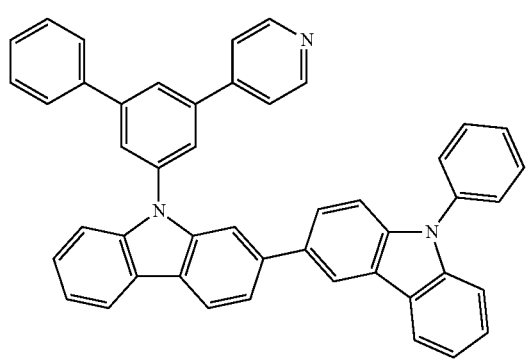

-continued
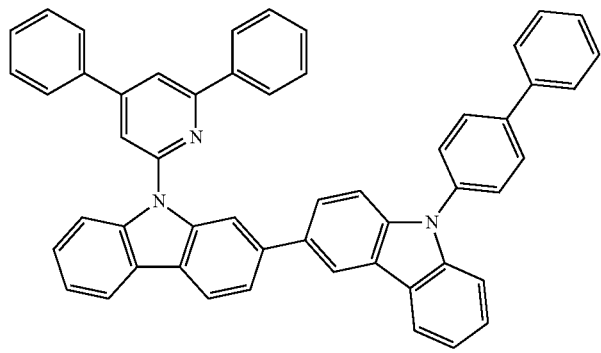
[B-74]
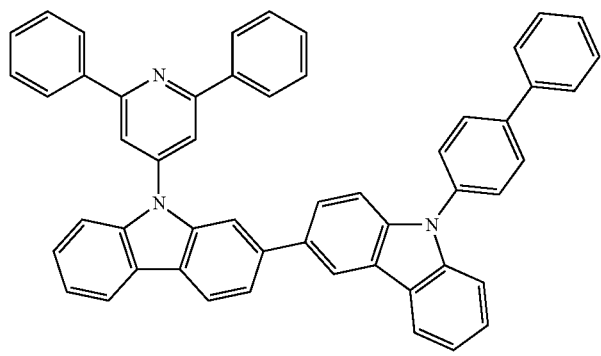
[B-75]
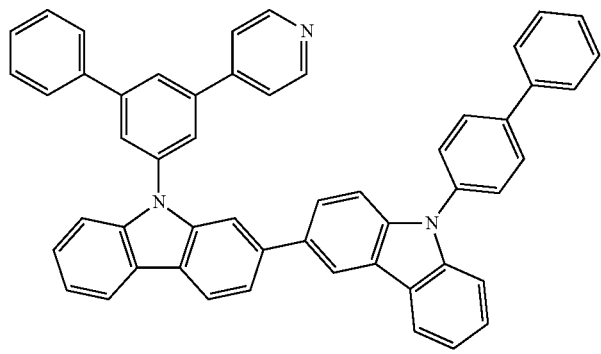
[B-76]
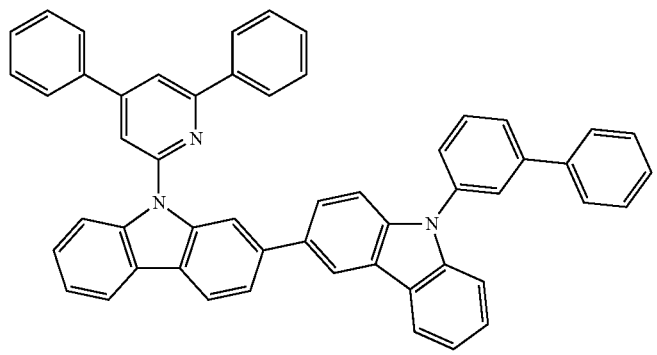
[B-77]

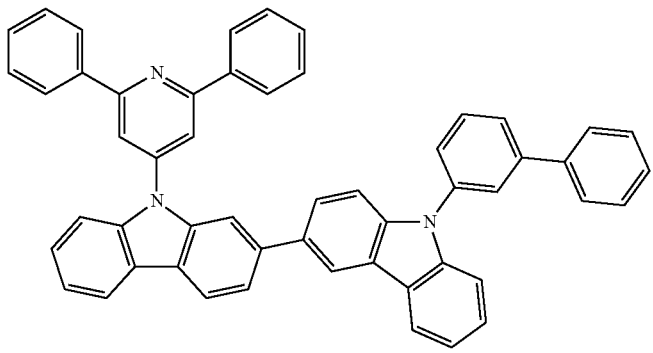
[B-78]
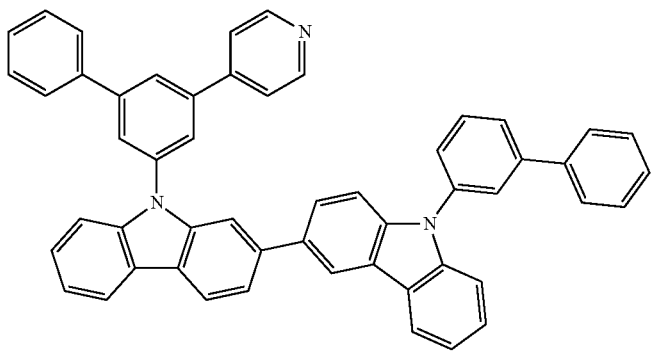
[B-79]
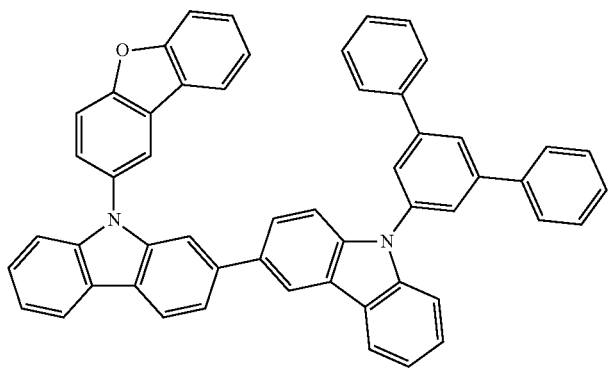
[B-80]
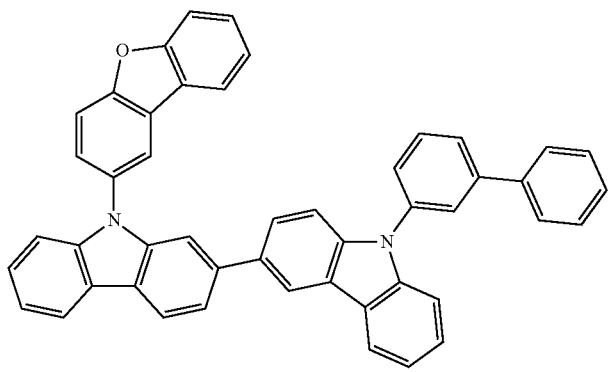
[B-81]

[B-82]
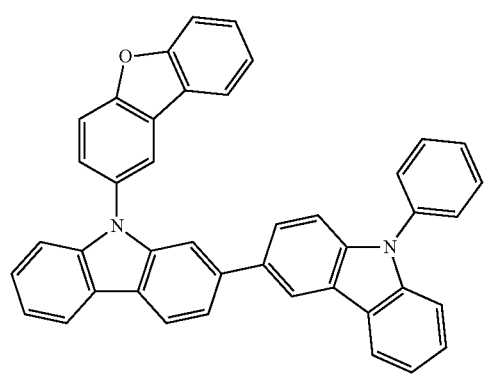
[B-83]
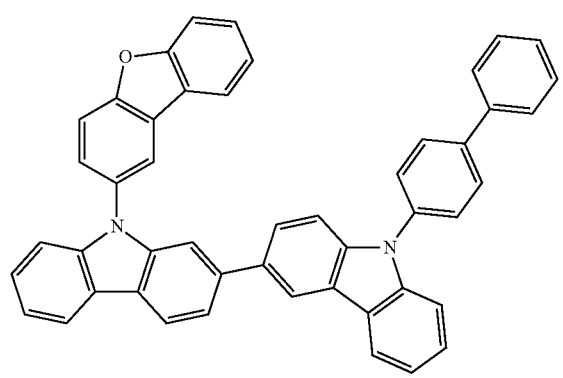
[B-84]
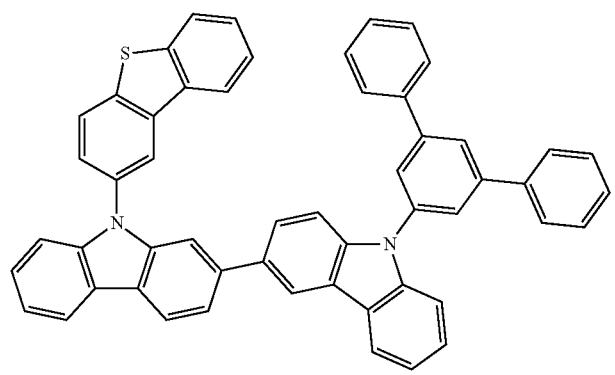
[B-85]
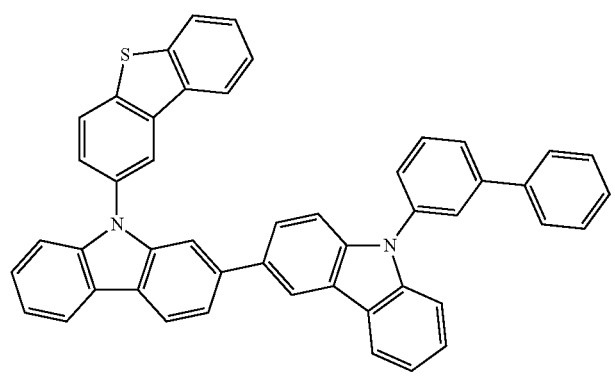

-continued
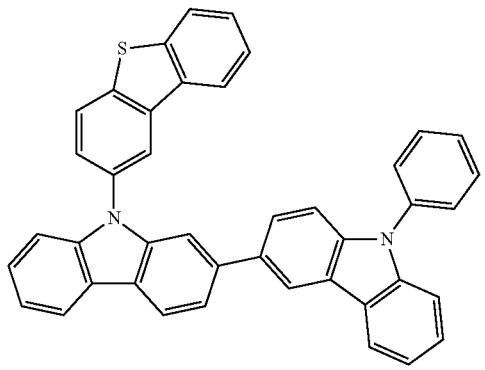
[B-86]
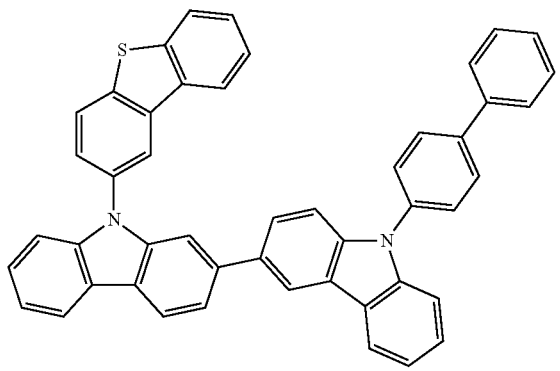
[B-87]
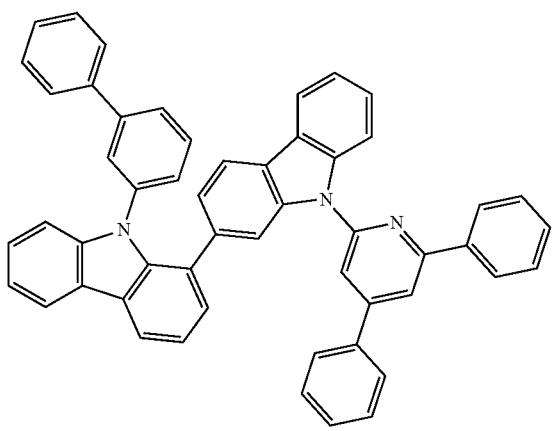
[B-88]
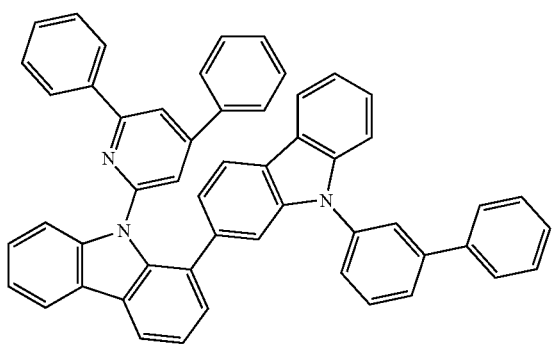
[B-89]

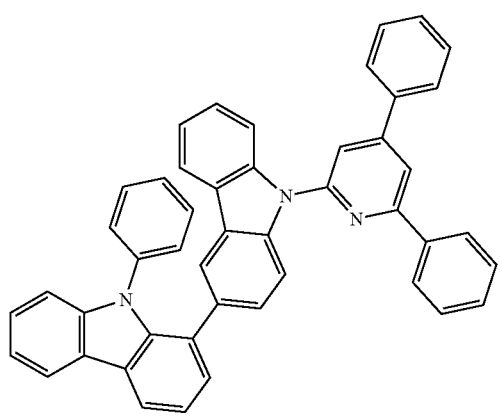
[B-90]
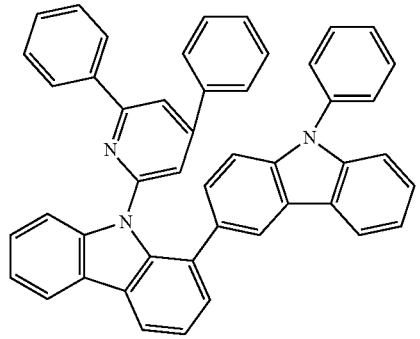
[B-91]
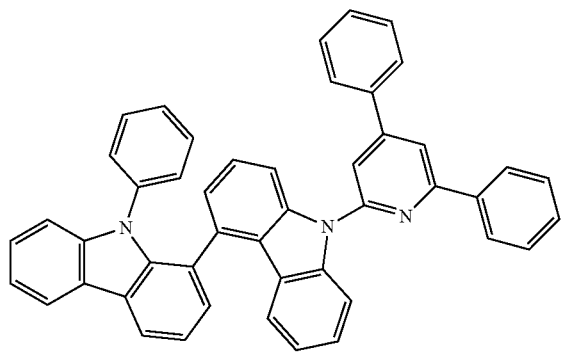
[B-92]
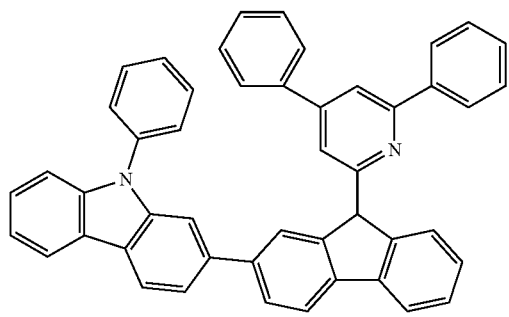
[B-93]

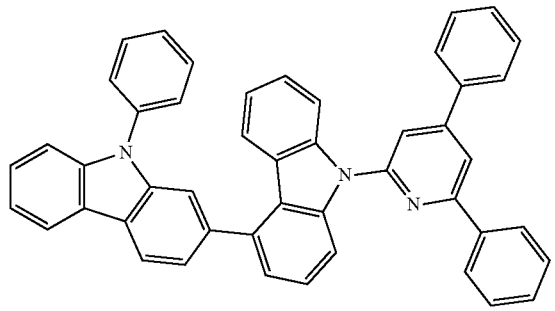
[B-94]
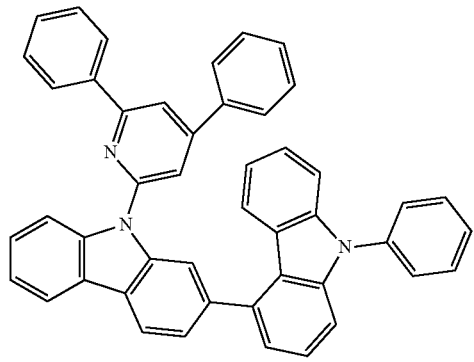
[B-95]
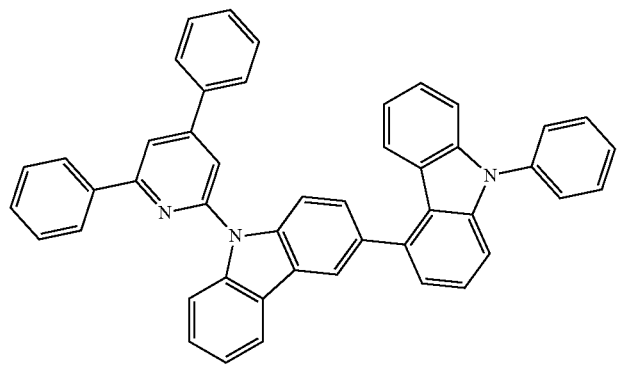
[B-96]

[B-97]
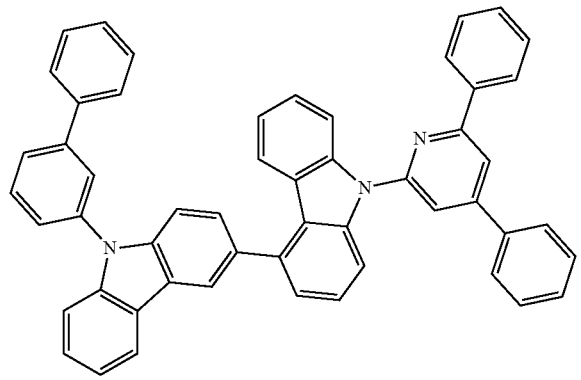
[B-98]
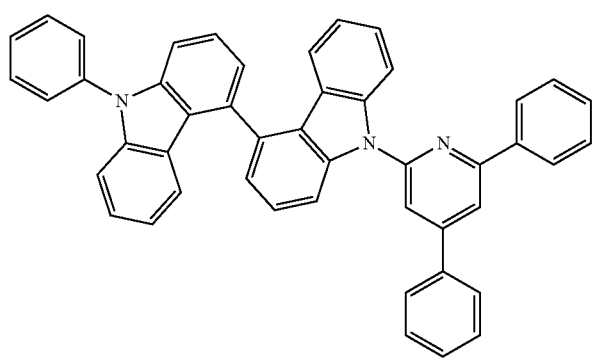
[B-99]
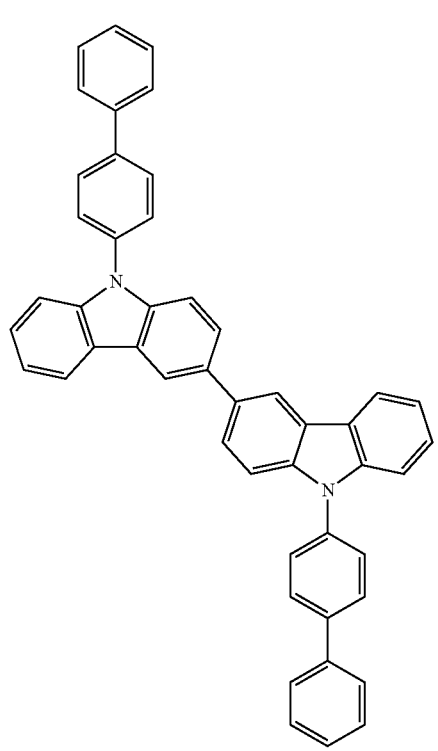

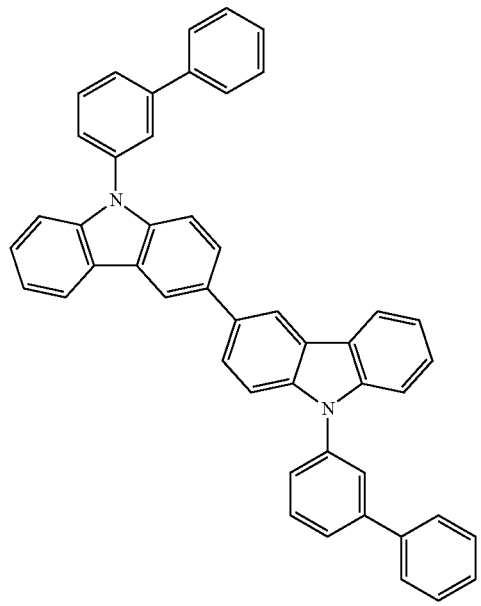
[B-100]
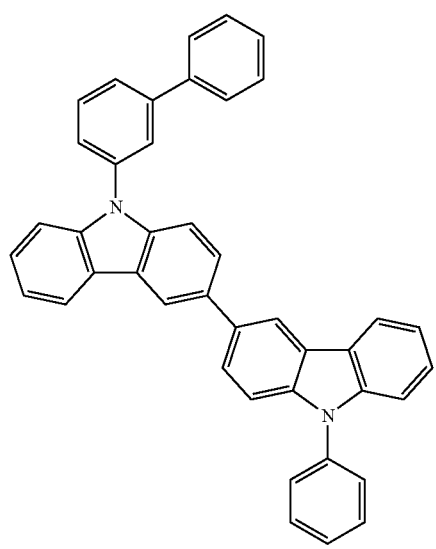
[B-101]
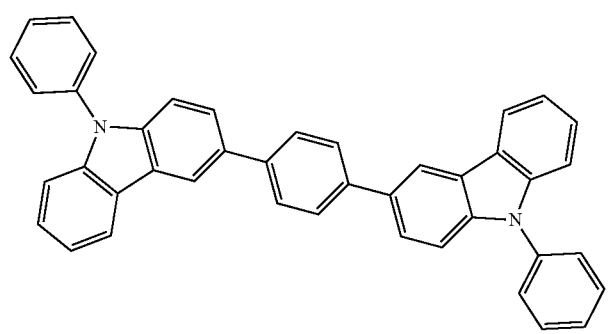
[B-102]

-continued
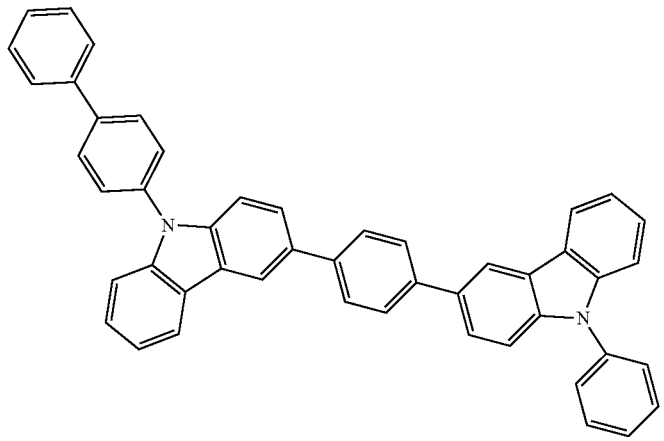
[B-103]
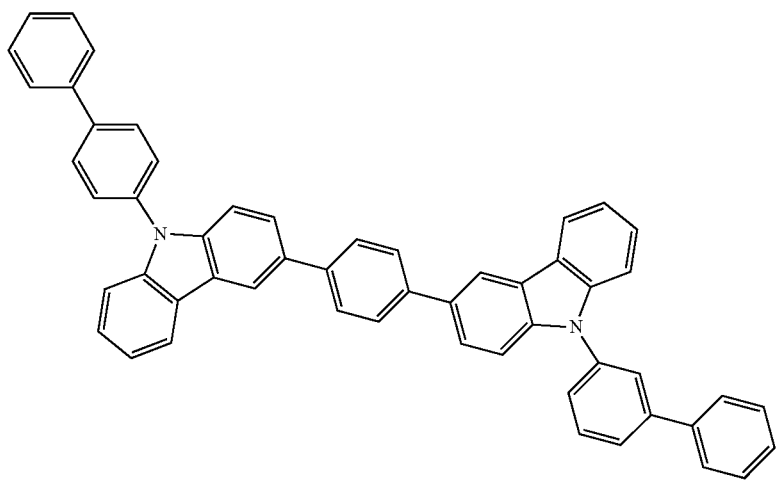
[B-104]
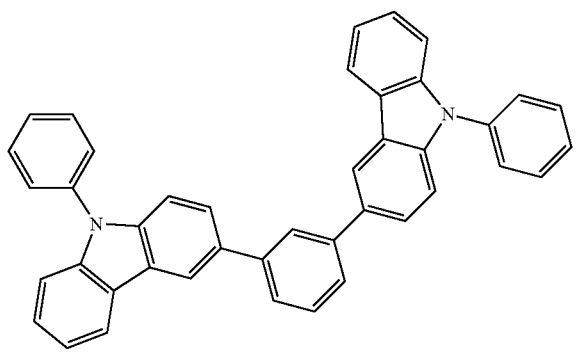
[B-105]
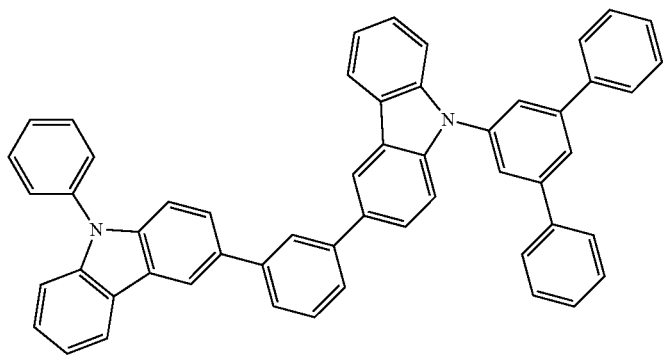
[B-106]

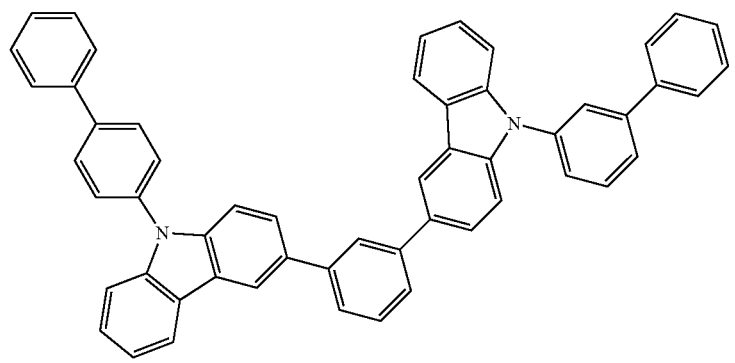
[B-107]
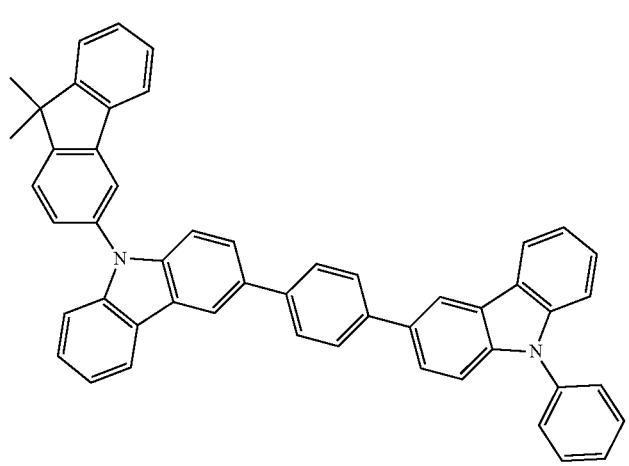
[B-108]
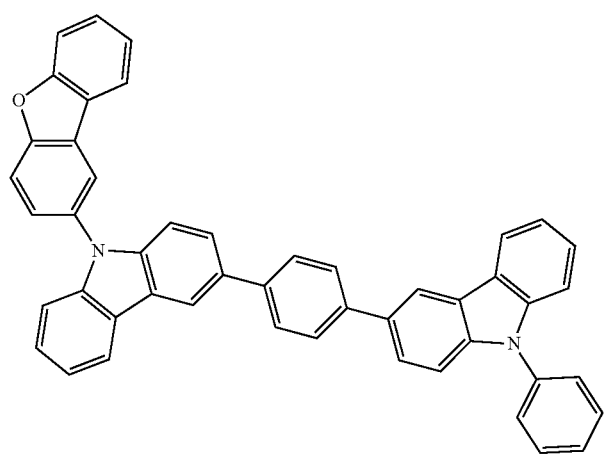
[B-109]

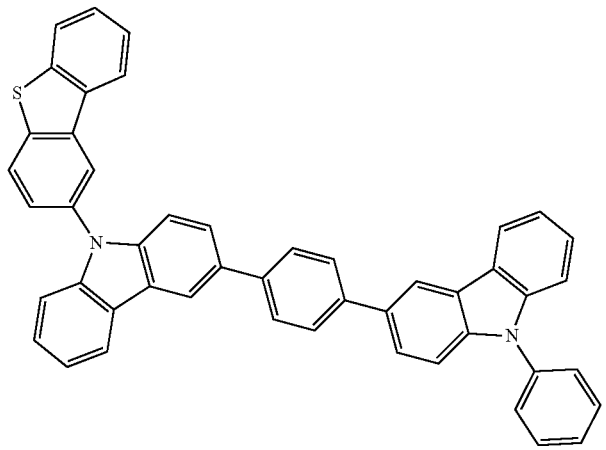
[B-110]
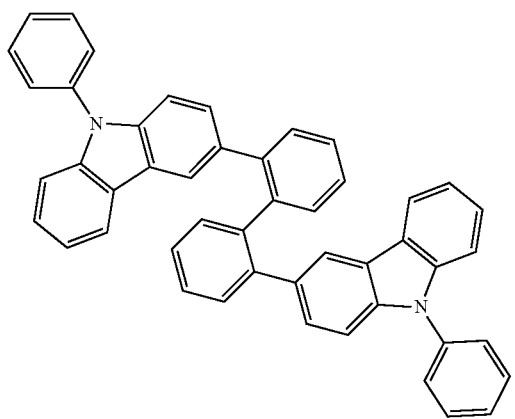
[B-111]
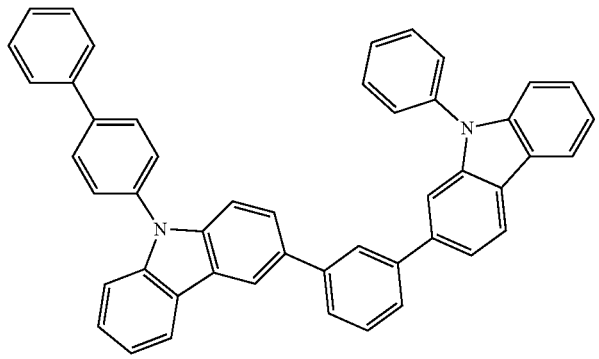
[B-112]

[B-113]
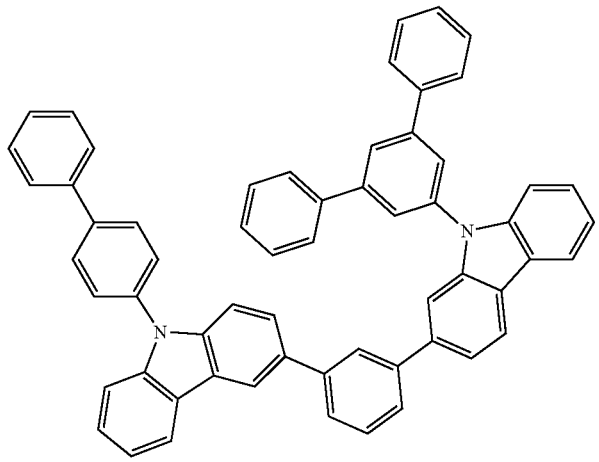
[B-114]
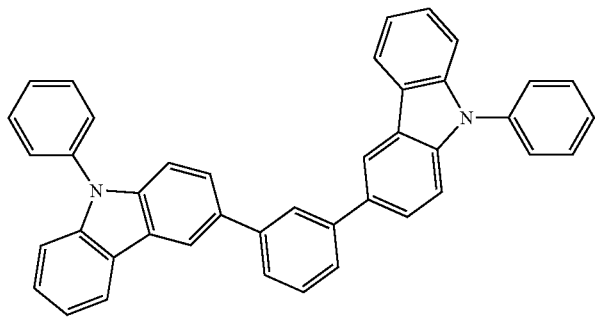
[B-115]
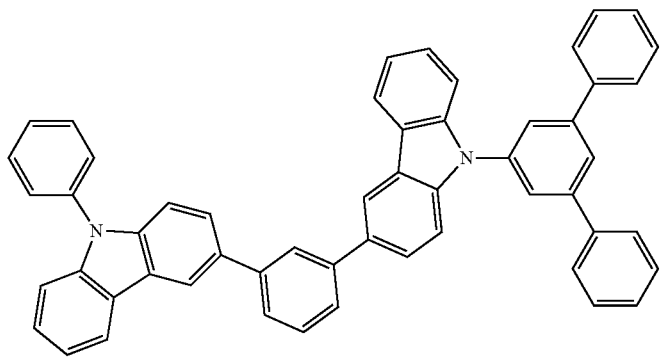
[B-116]
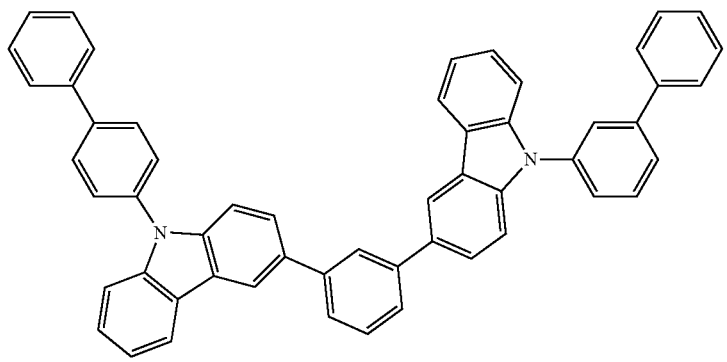

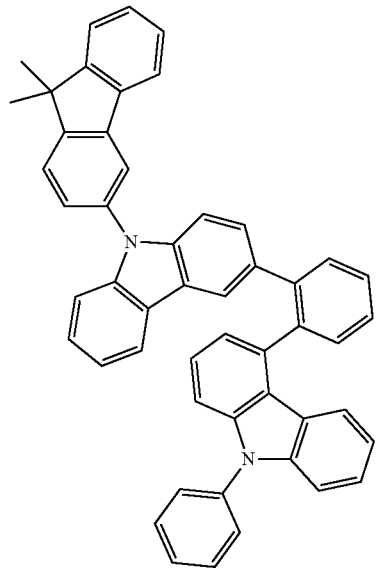
[B-117]
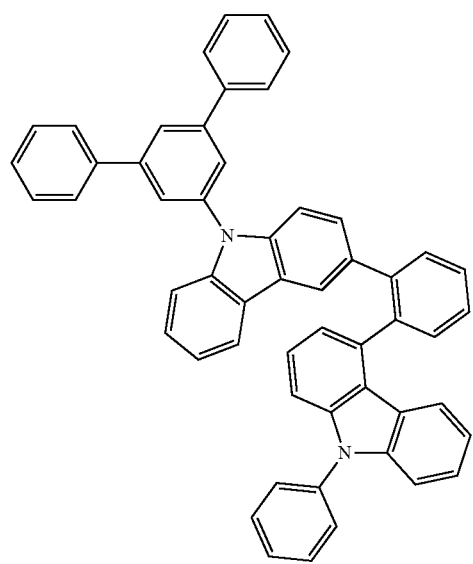
[B-118]

-continued
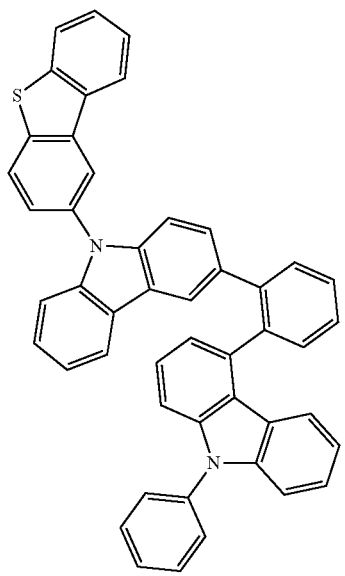
[B-119]
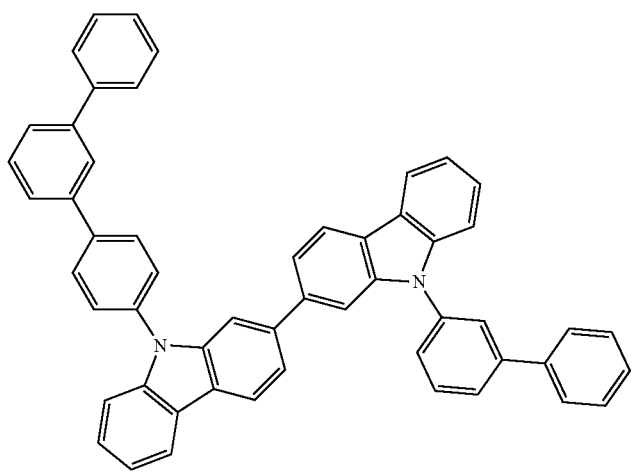
[B-120]
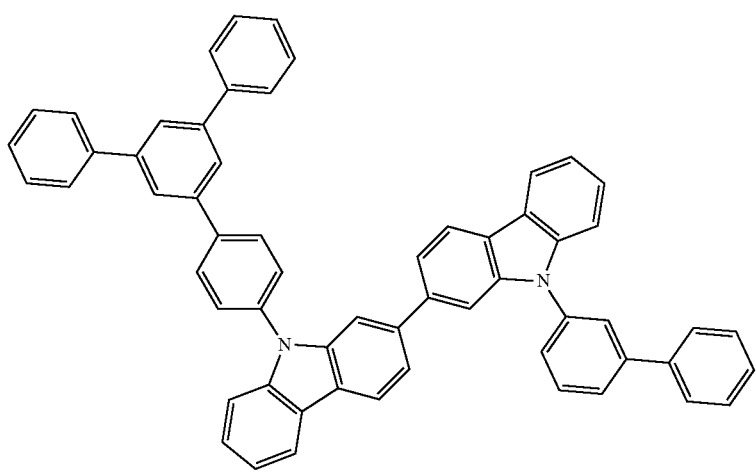
[B-121]

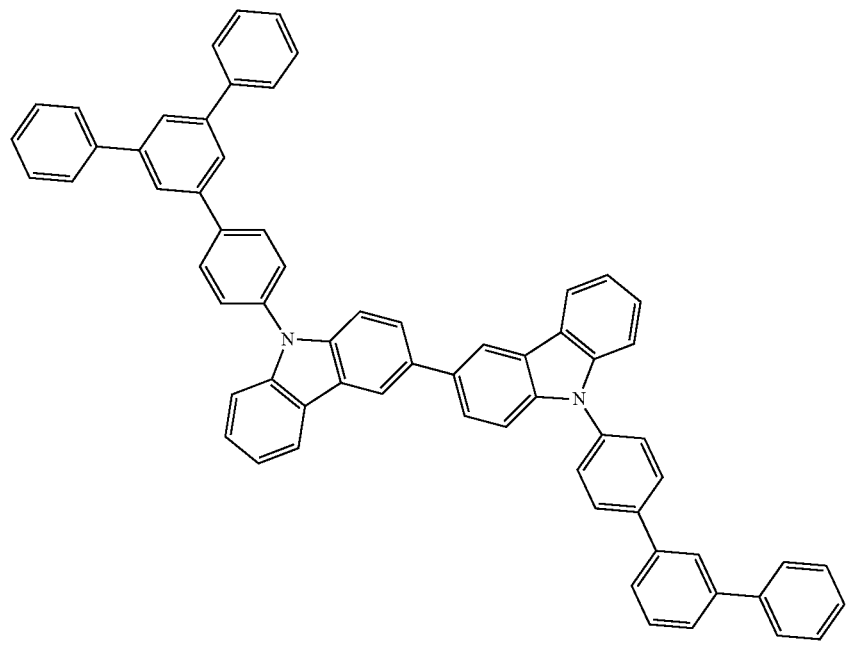
[B-122]
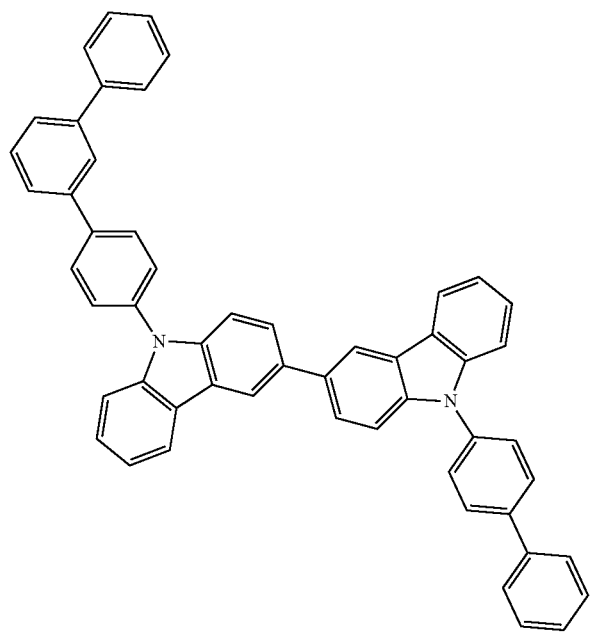
[B-123]

[B-124]
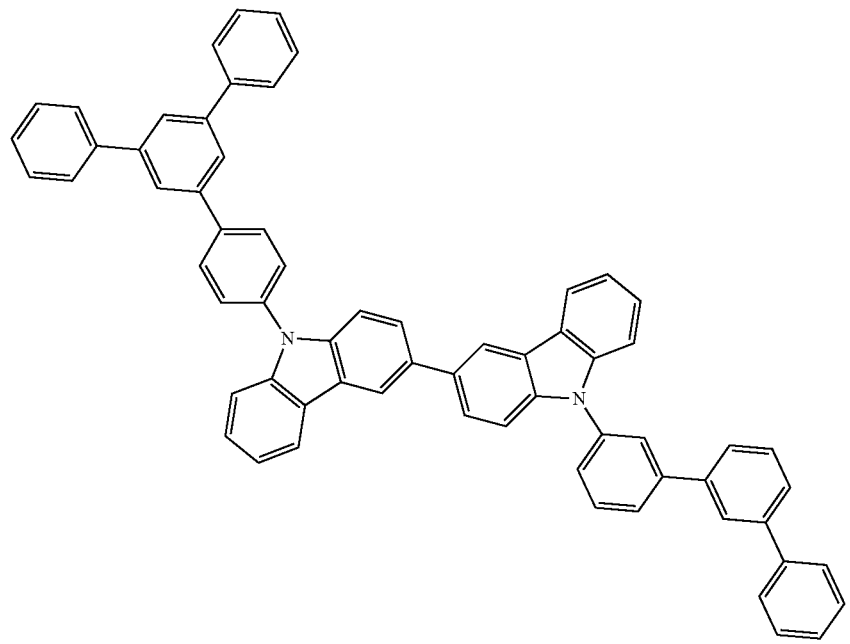
[B-125]
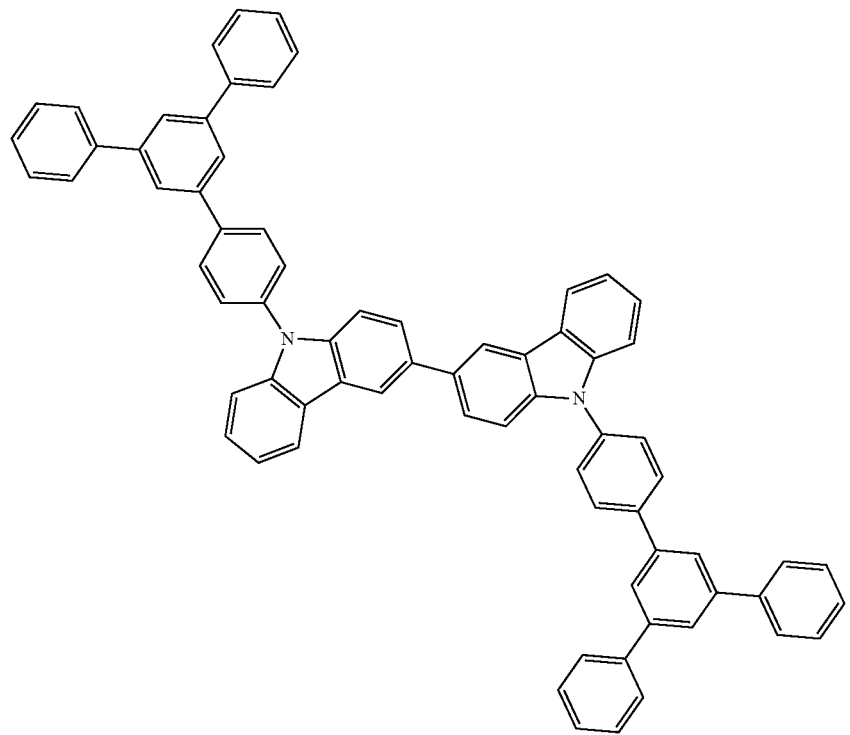

[B-126]
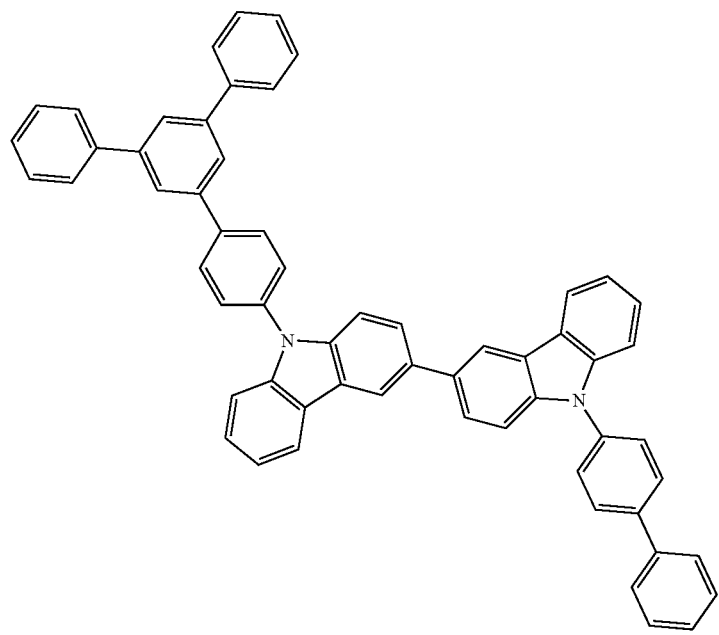
[B-127]
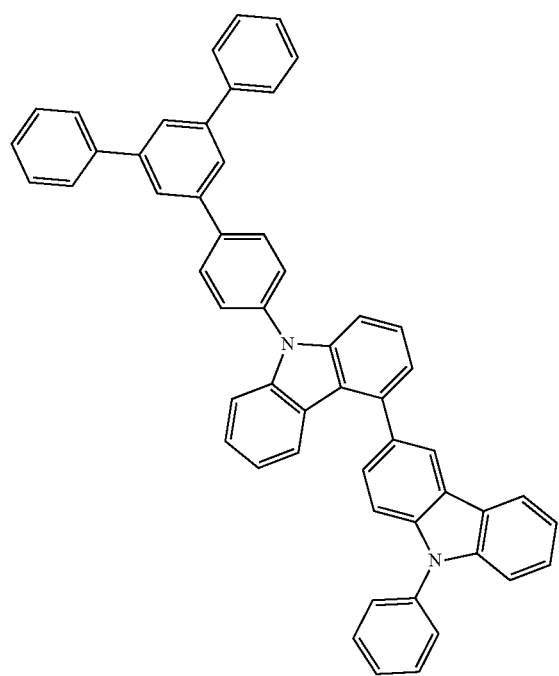

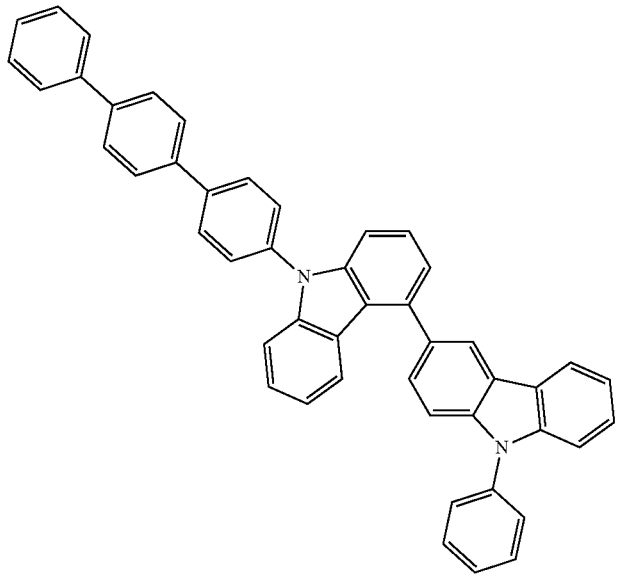
[B-128]
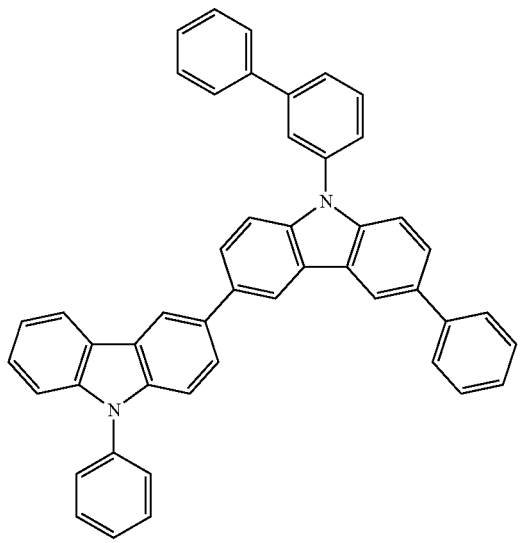
[B-129]

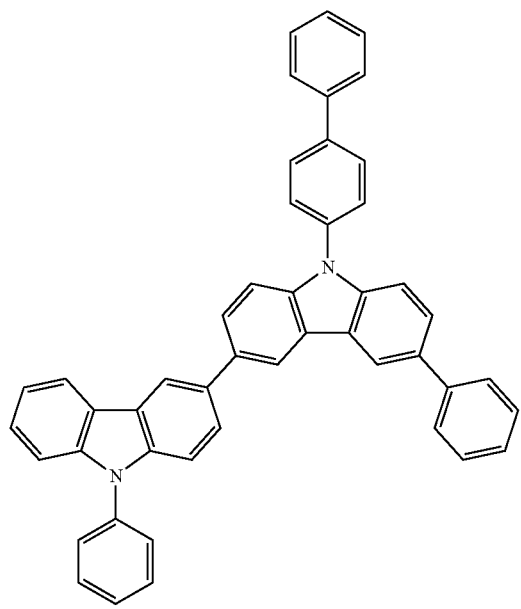
[B-130]
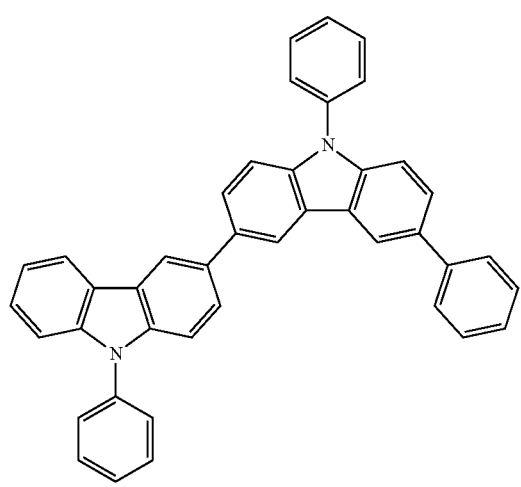
[B-131]
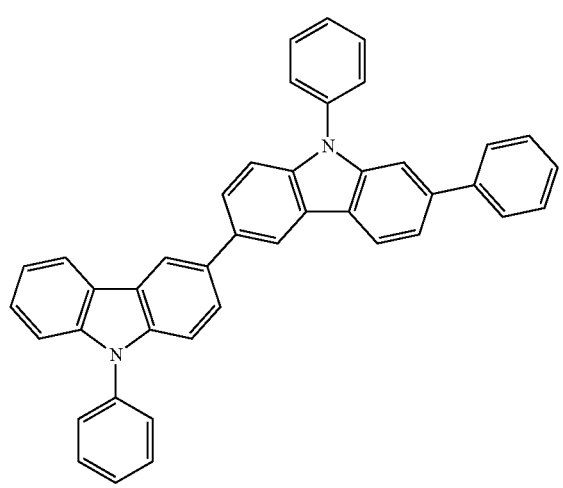
[B-132]

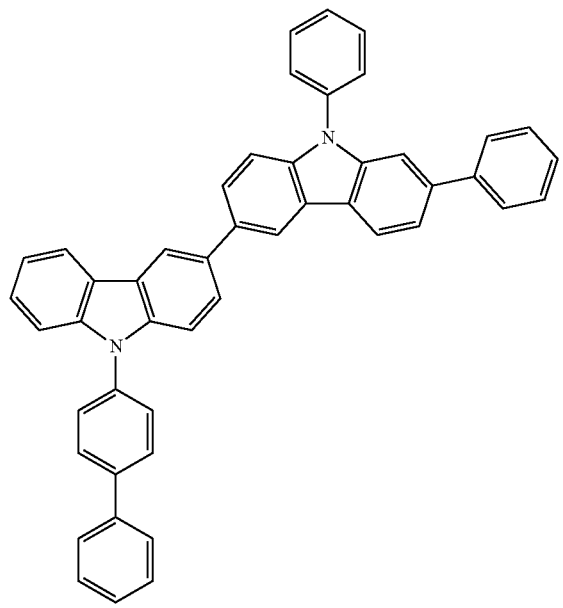
[B-133]
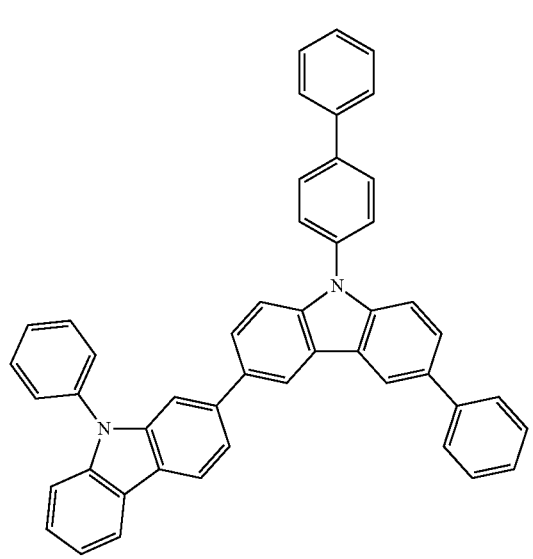
[B-134]
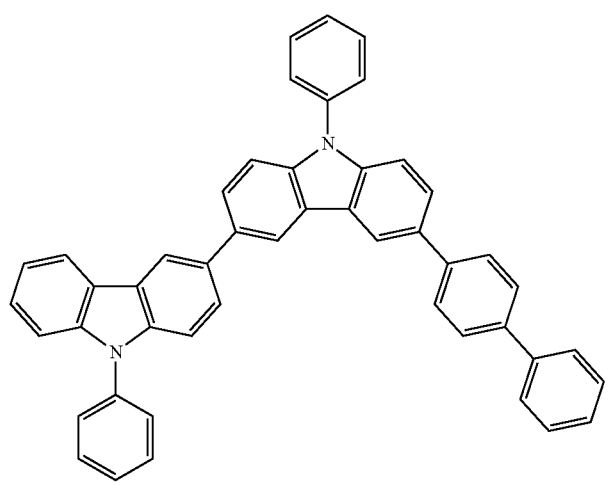
[B-135]

-continued
[B-136]
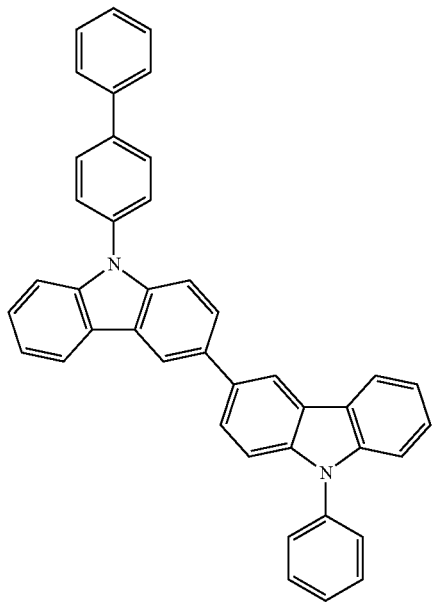
[B-137]
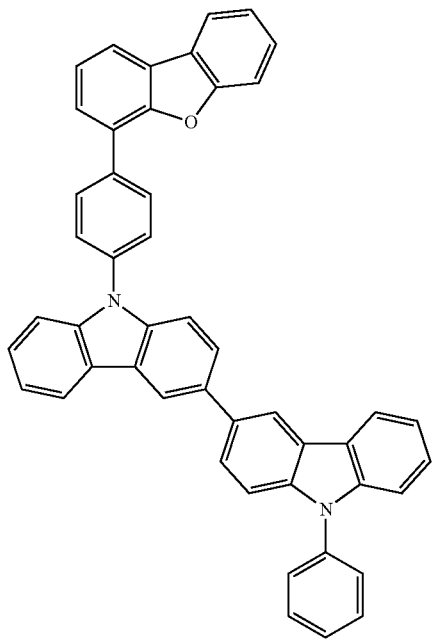

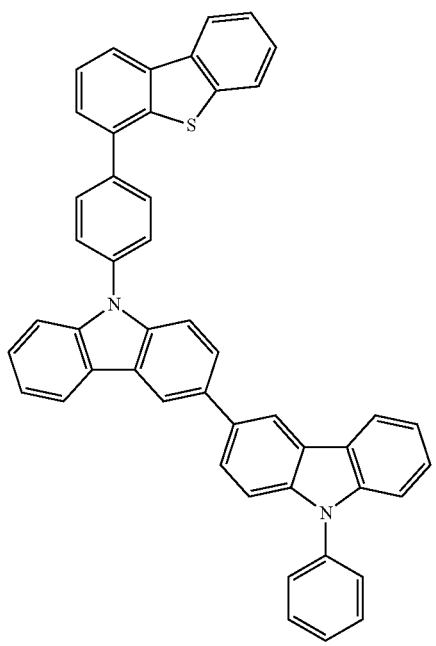

[B-138]

The first compound and the second compound may be applied in a form of a composition.

In an example embodiment, the compound or the composition may be a host.

In an example embodiment, the composition may include the first compound represented by Chemical Formula 1A-3 and the second compound represented by Chemical Formula 3A as each host.

For example, the first compound of the composition may be represented by one of Chemical Formula 1A-3f, Chemical Formula 1A-3h, and Chemical Formula 1A-3i.

The first compound and the second compound may be for example included in a weight ratio of about 1:99 to about 99:1. Within the range, a desirable weight ratio may be adjusted using an electron transport capability of the first compound and a hole transport capability of the second compound to realize bipolar characteristics and thus to improve efficiency and life-span. Within the range, they may be for example included in a weight ratio of about 90:10 to about 10:90, about 80:20 to about 20:80, about 80:20 to about 30: 70, about 80:20 to about 40:60, or about 80:20 to about 50:50. In an example embodiment, they may be included in a weight ratio of about 80:20 to 60:40, and specifically, a weight ratio of about 70:30.

The compound or the composition may further include a dopant. The dopant may be for example a phosphorescent dopant, for example a red, green, or blue phosphorescent dopant, for example a red or green phosphorescent dopant.

The dopant is a material in small amount to cause light emission and generally a material such as a metal complex that emits light by multiple excitation into a triplet or more. The dopant may be, for example an inorganic, organic, or organic/inorganic compound, and one or more kinds thereof may be used.

Examples of the dopant may be a phosphorescent dopant and examples of the phosphorescent dopant may be an organic metal compound including Ir, Pt, Os, Ti, Zr, Hf, Eu, Tb, Tm, Fe, Co, Ni, Ru, Rh, Pd, or a combination thereof.

The phosphorescent dopant may be, for example a compound represented by Chemical Formula Z.

$$L^3MX^4 \qquad [\text{Chemical Formula Z}]$$

In Chemical Formula Z, M may be a metal, and $L^3$ and $X^4$ may be the same or different, and may be a ligand to form a complex compound with M.

The M may be for example Ir, Pt, Os, Ti, Zr, Hf, Eu, Tb, Tm, Fe, Co, Ni, Ru, Rh, Pd, or a combination thereof, and the $L^3$ and $X^4$ may be, for example a bidendate ligand.

The compound or the composition may be formed by a dry film formation method such as chemical vapor deposition (CVD).

Hereinafter, an organic optoelectronic device including the compound or the composition is described.

The organic optoelectronic device may be a device to convert electrical energy into photo energy or vice versa, and may be for example an organic photoelectric device, an organic light emitting diode, an organic solar cell, and an organic photo conductor drum.

Herein, an organic light emitting diode as an example of an organic optoelectronic device is described referring to drawings.

FIGS. 1 and 2 illustrate cross-sectional views of organic light emitting diodes according to example embodiments.

Referring to FIG. 1, an organic optoelectronic device 100 according to an example embodiment includes an anode 120 and a cathode 110 and facing each other and an organic layer 105 disposed between the anode 120 and the cathode 110.

The anode 120 may be made of a conductor having a large work function to help hole injection, and may be for example metal, metal oxide and/or a conductive polymer. The anode 120 may be, for example a metal such as nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of metal and oxide such as ZnO and Al or $SnO_2$ and Sb; a conductive polymer such as poly(3-methylthiophene), poly(3,4-(ethylene-1,2-dioxy) thiophene) (PEDOT), polypyrrole, and polyaniline, but is not limited thereto.

The cathode 110 may be made of a conductor having a small work function to help electron injection, and may be for example metal, metal oxide and/or a conductive polymer. The cathode 110 may be for example a metal such as magnesium, calcium, sodium, potassium, titanium, indium, yttrium, lithium, gadolinium, aluminum, silver, tin, lead, cesium, barium, and the like or an alloy thereof; a multi-layer structure material such as LiF/Al, LiO$_2$/Al, LiF/Ca, LiF/Al and BaF$_2$/Ca, but is not limited thereto.

The organic layer 105 may include a light emitting layer 130 including the compound or the composition.

The light emitting layer 130 may include for example the compound or the composition according to an embodiment.

Referring to FIG. 2, in an example embodiment, an organic light emitting diode 200 further includes a hole auxiliary layer 140 in addition to the light emitting layer 130. The hole auxiliary layer 140 may further increase hole injection and/or hole mobility and block electrons between the anode 120 and the light emitting layer 130. The hole auxiliary layer 140 may be for example a hole transport layer (HTL), a hole injection layer (HIL), and/or an electron blocking layer, and may include at least one layer.

The hole auxiliary layer 140 may include for example at least one of compounds of Group A below.

For example, the hole auxiliary layer 140 may include a hole transport layer between the anode 120 and the light emitting layer 130 and a hole transport auxiliary layer between the light emitting layer 130 and the hole transport layer, and at least one of compounds of Group A may be included in the hole transport auxiliary layer.

[Group A]

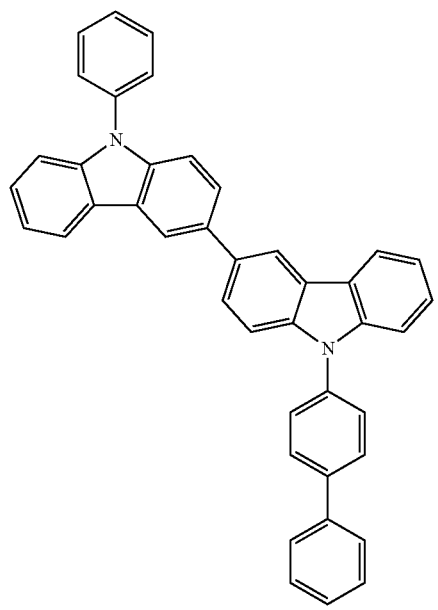

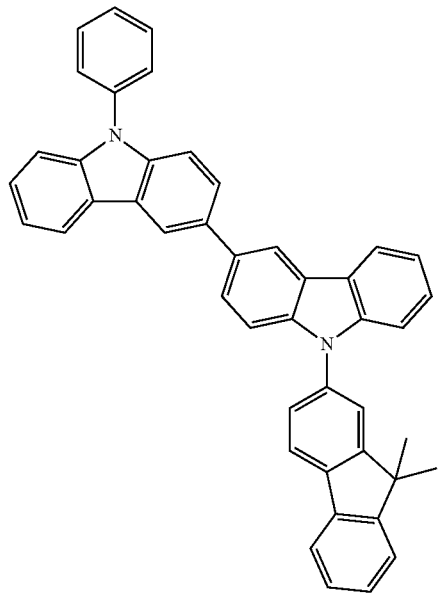

-continued

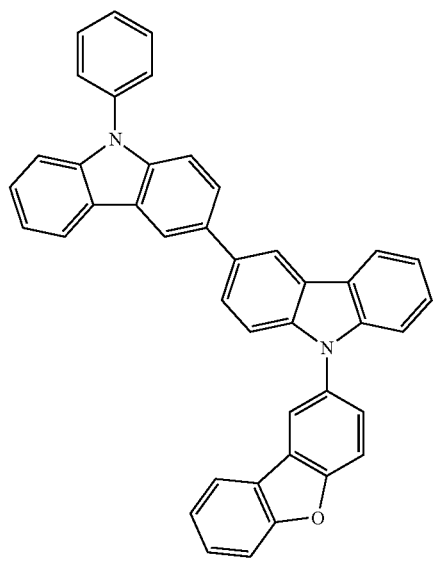

135
-continued
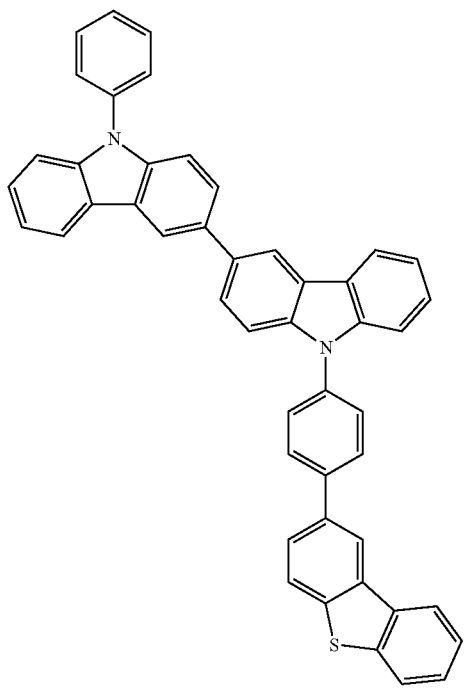
136
-continued
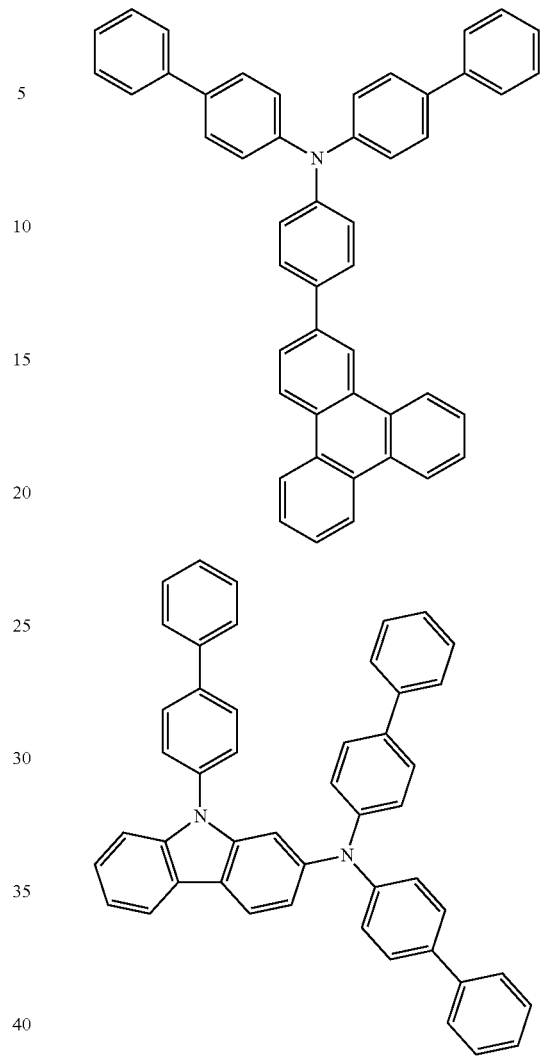
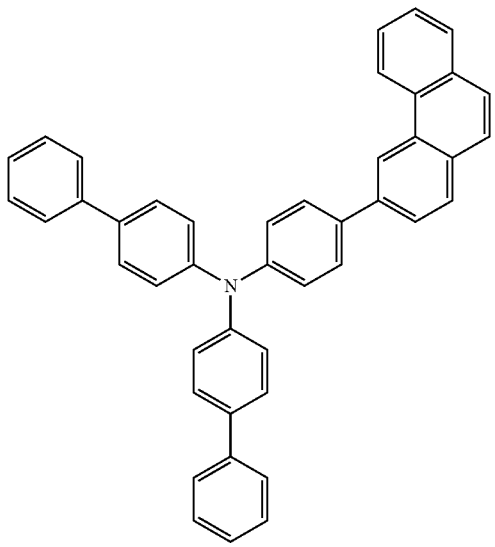
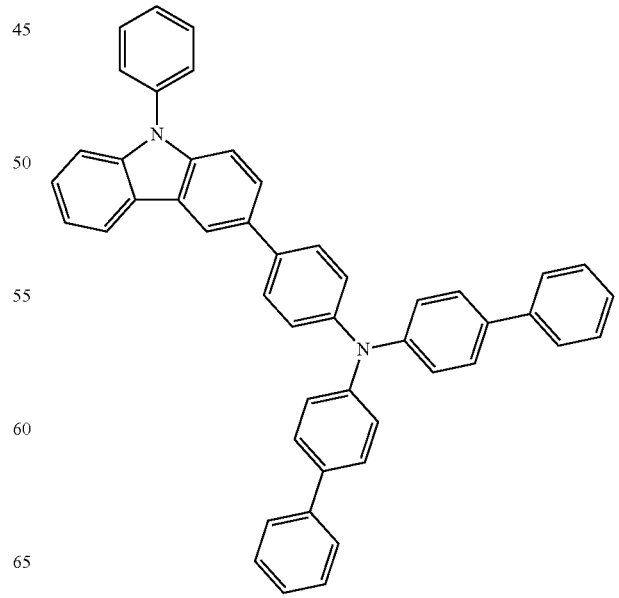

137 -continued
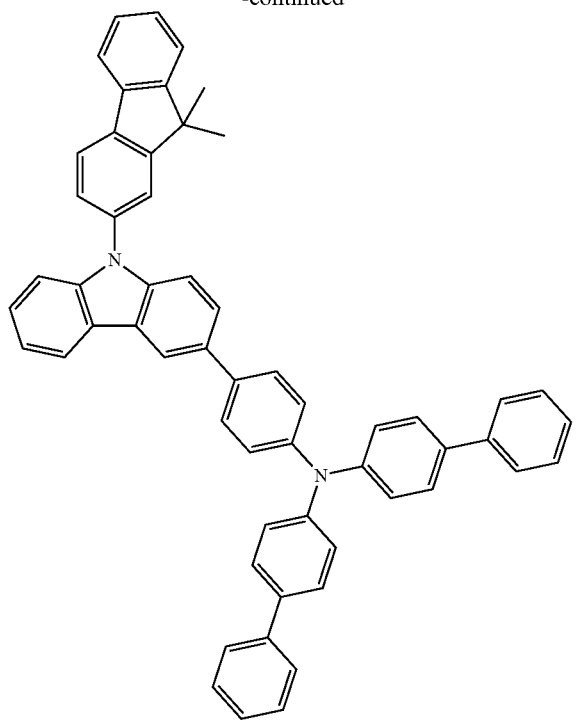
138 -continued
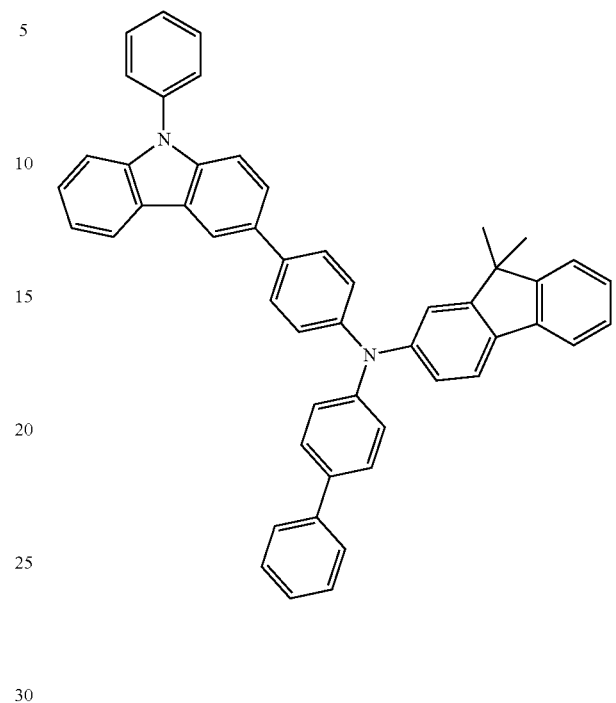
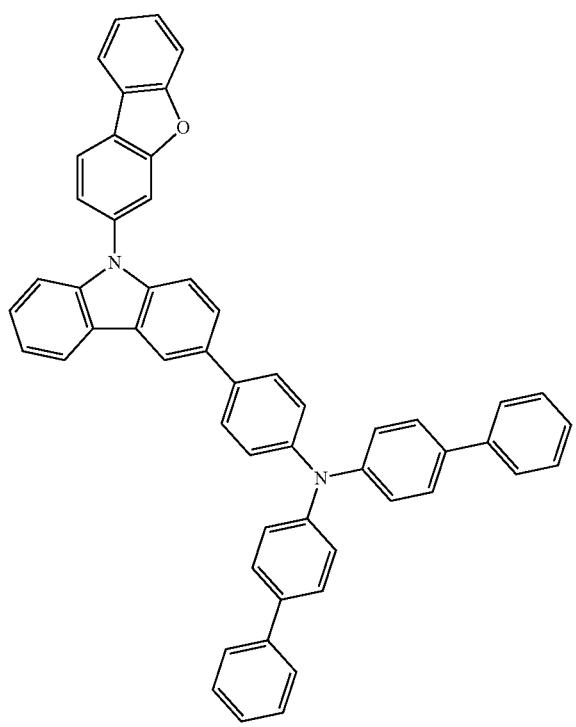
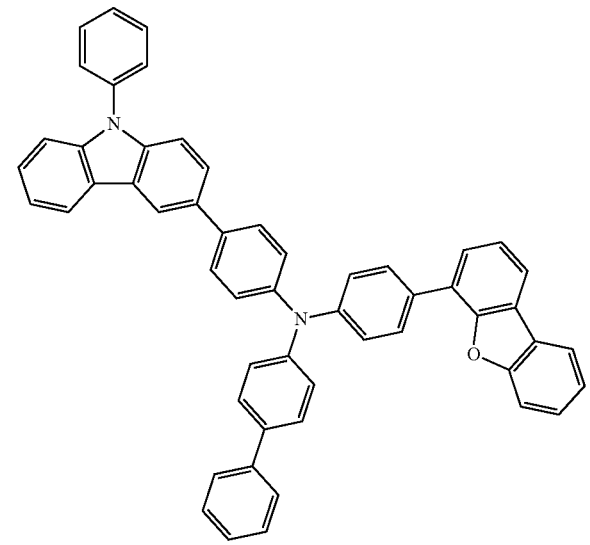

139
-continued
140
-continued
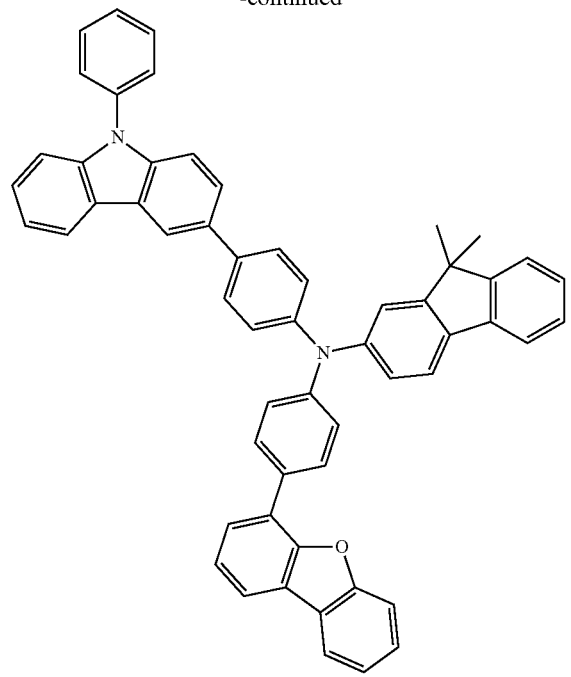
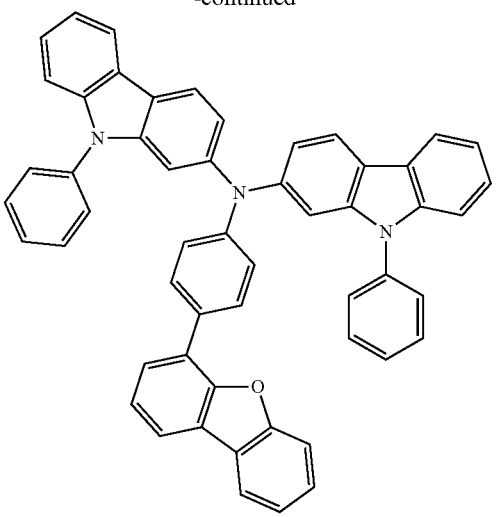
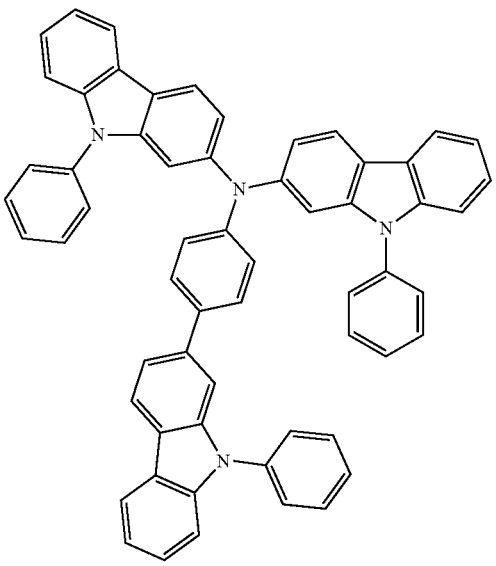
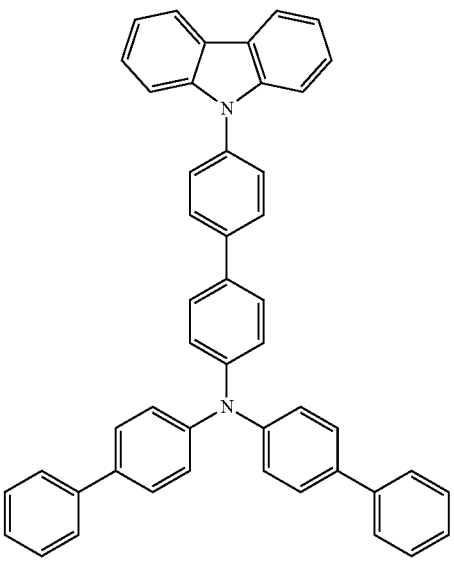

141
-continued
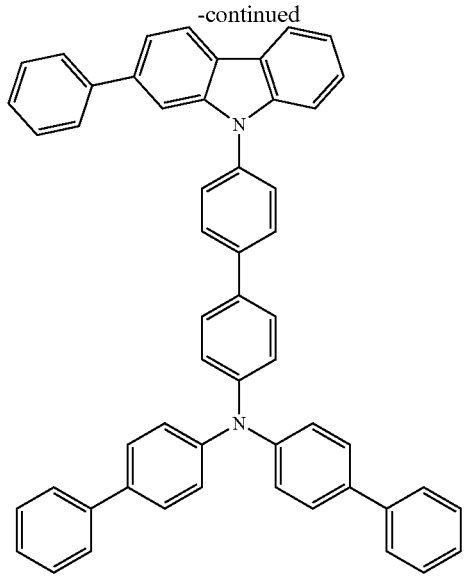
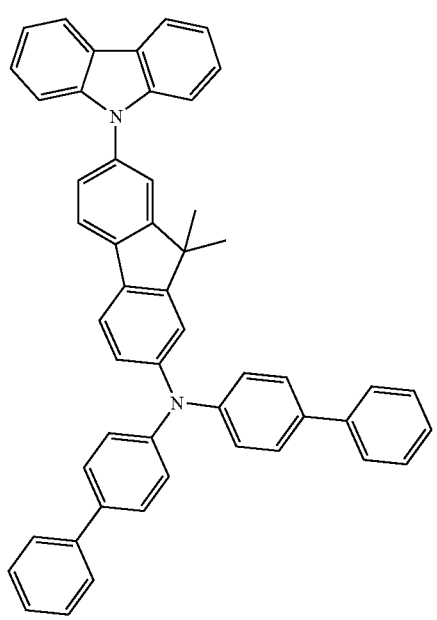
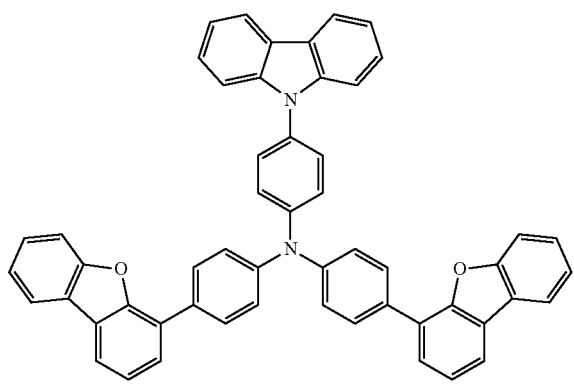
142
-continued
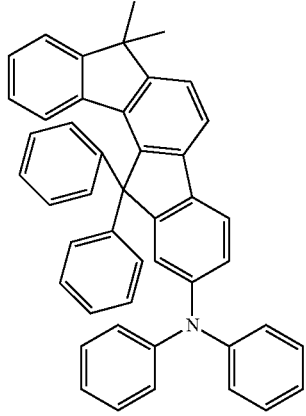
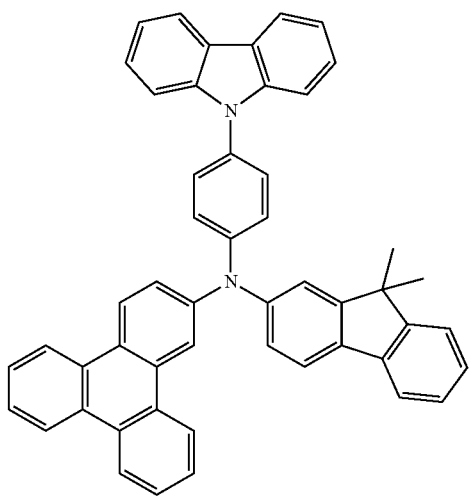

143
-continued
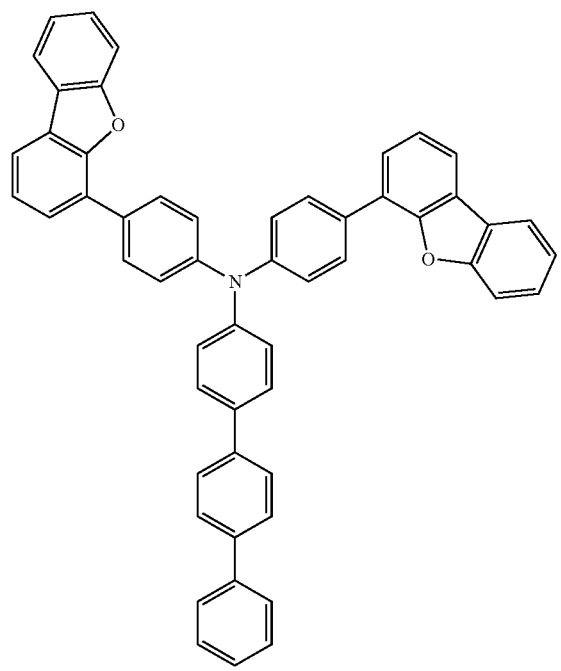
144
-continued
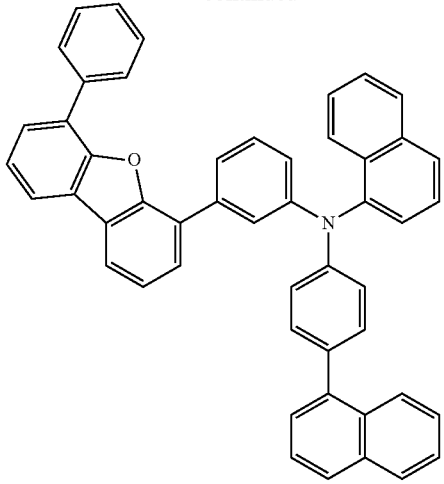
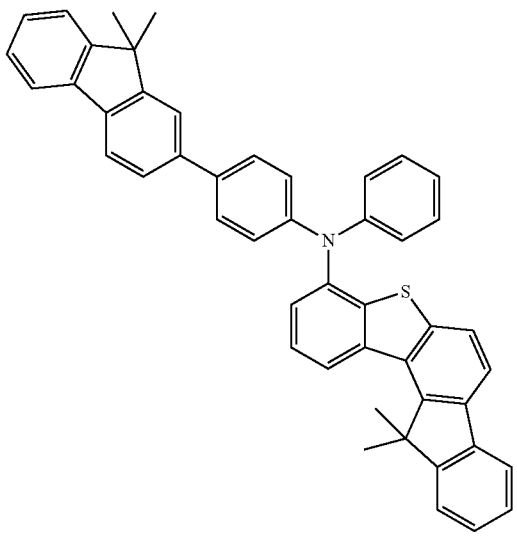
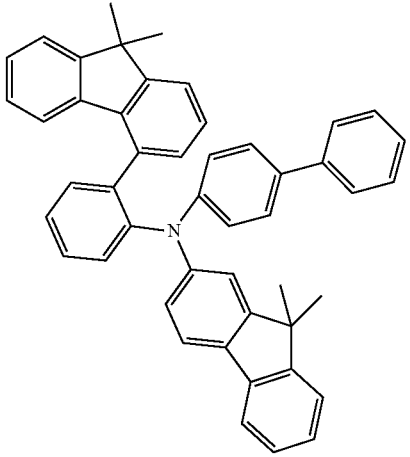

145
-continued
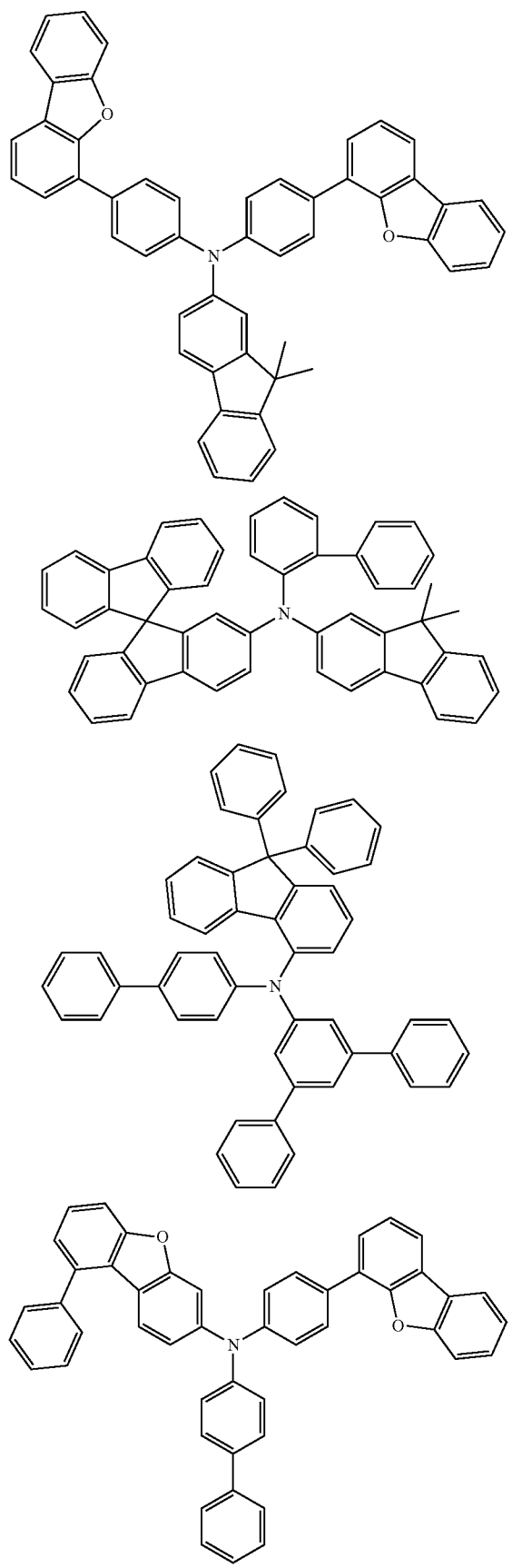
146
-continued
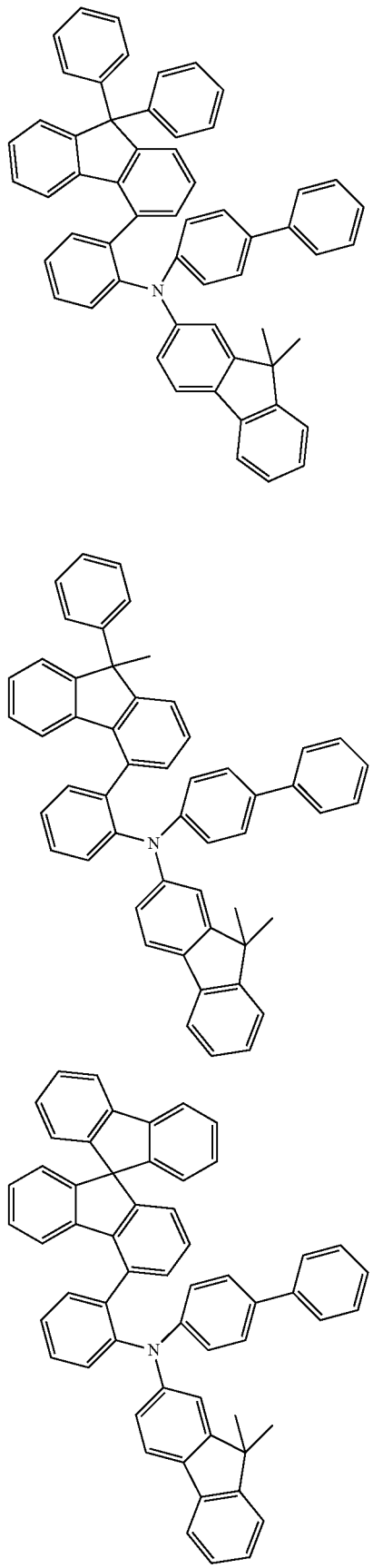

147
-continued
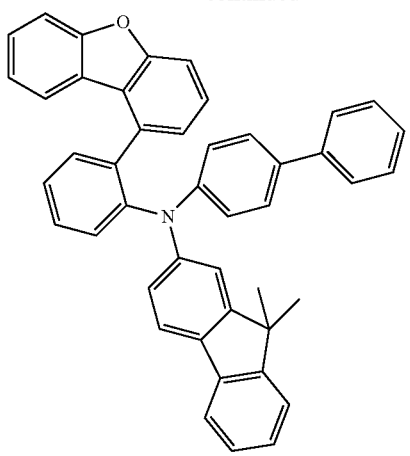
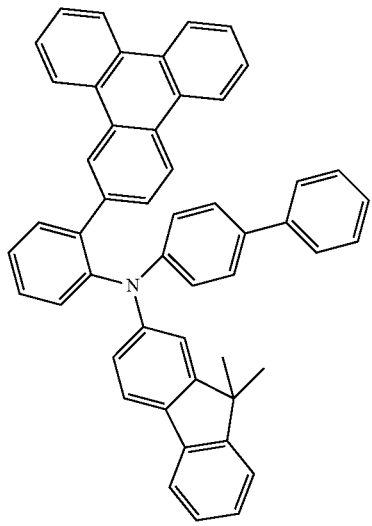
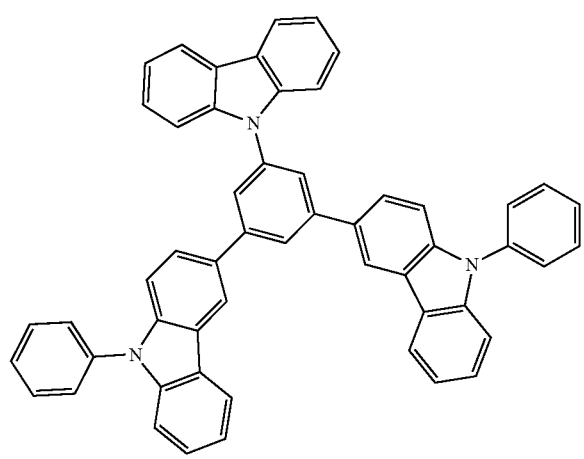
148
-continued
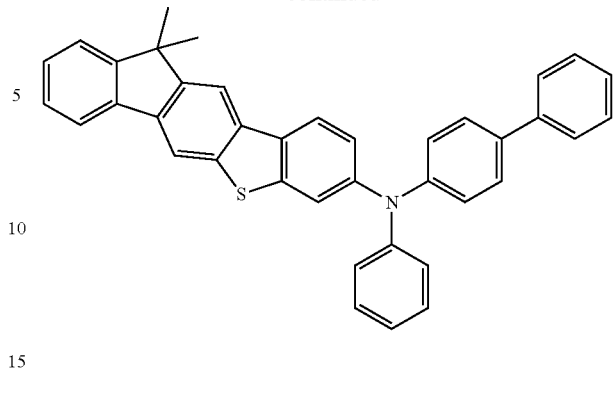
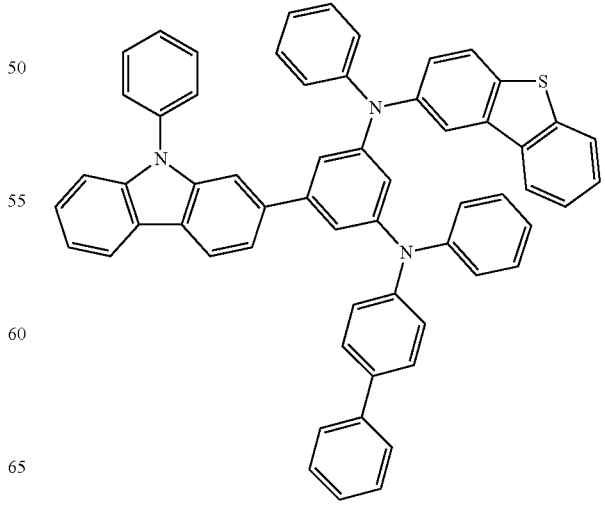

149
-continued
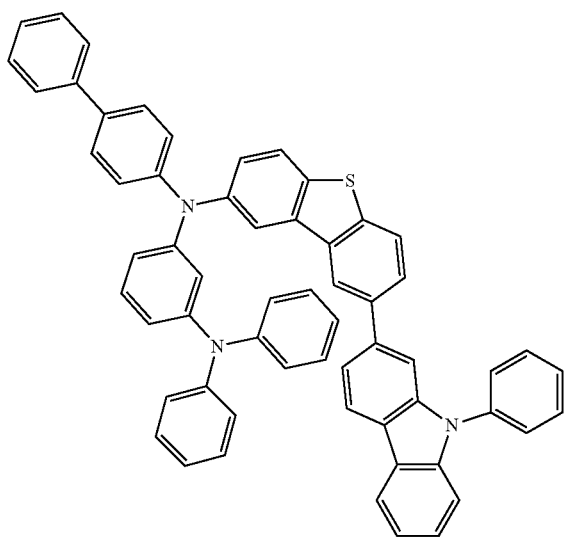
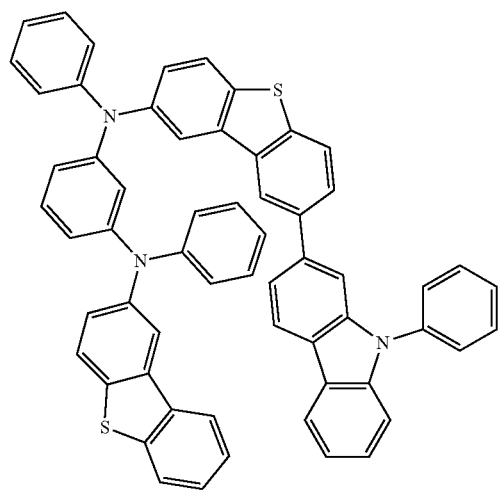
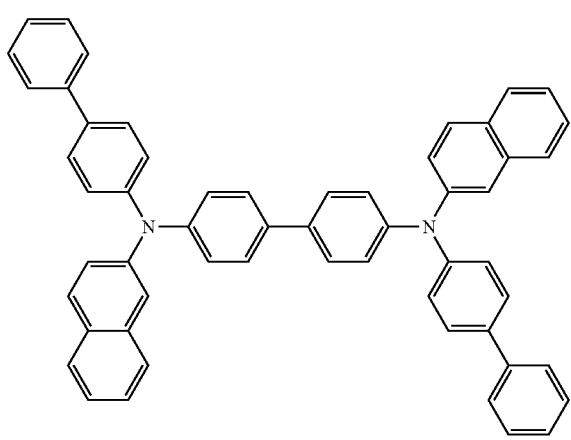
150
-continued
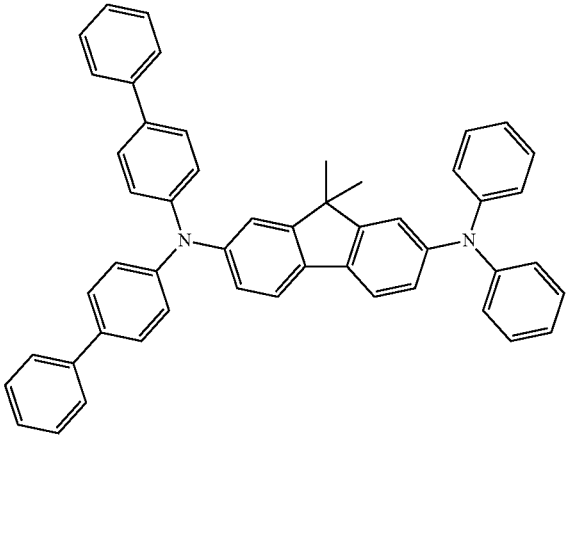
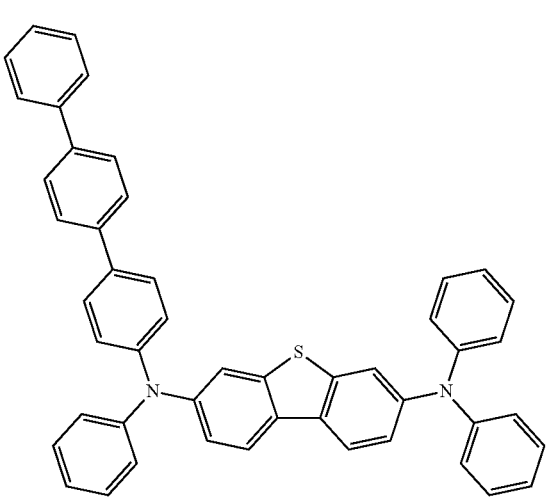
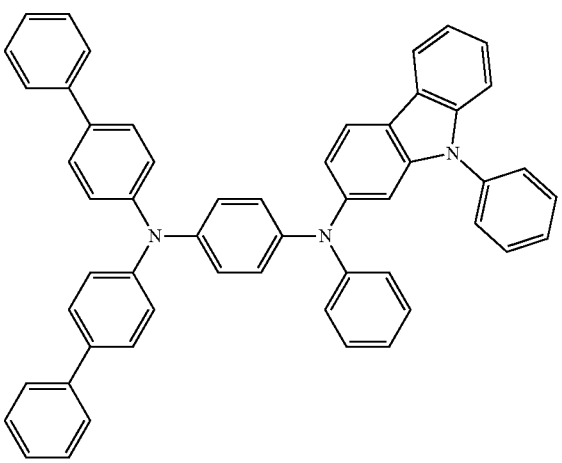

151
-continued
152
-continued
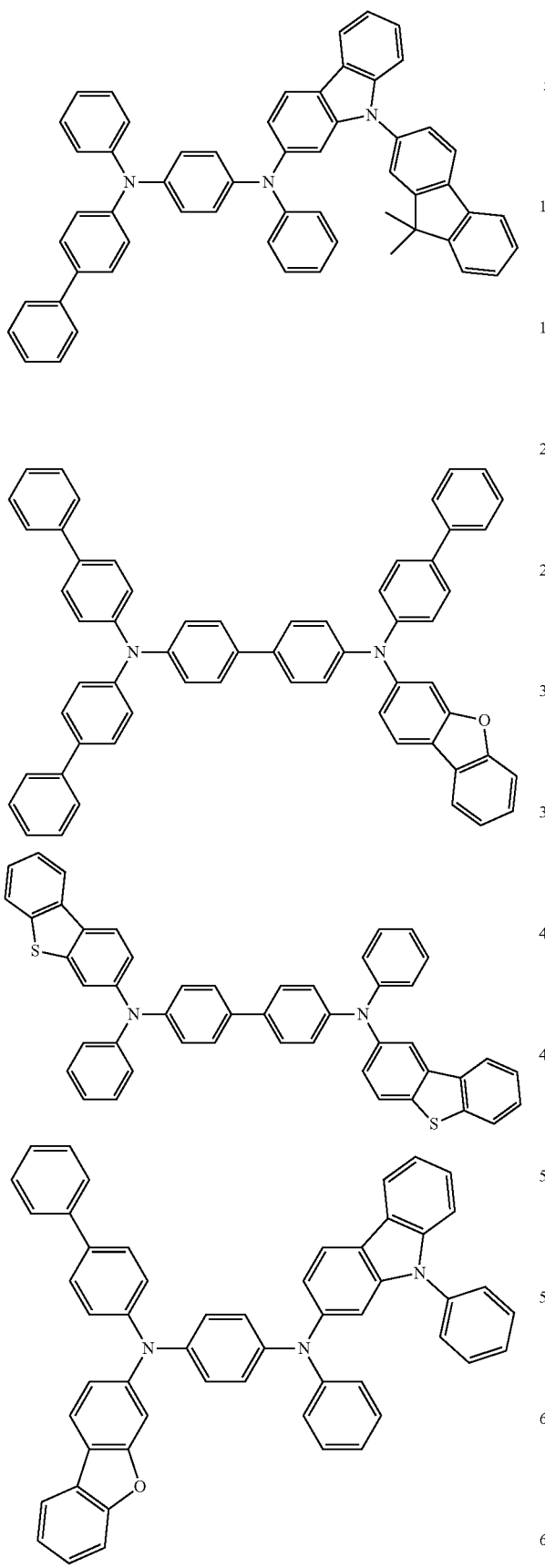
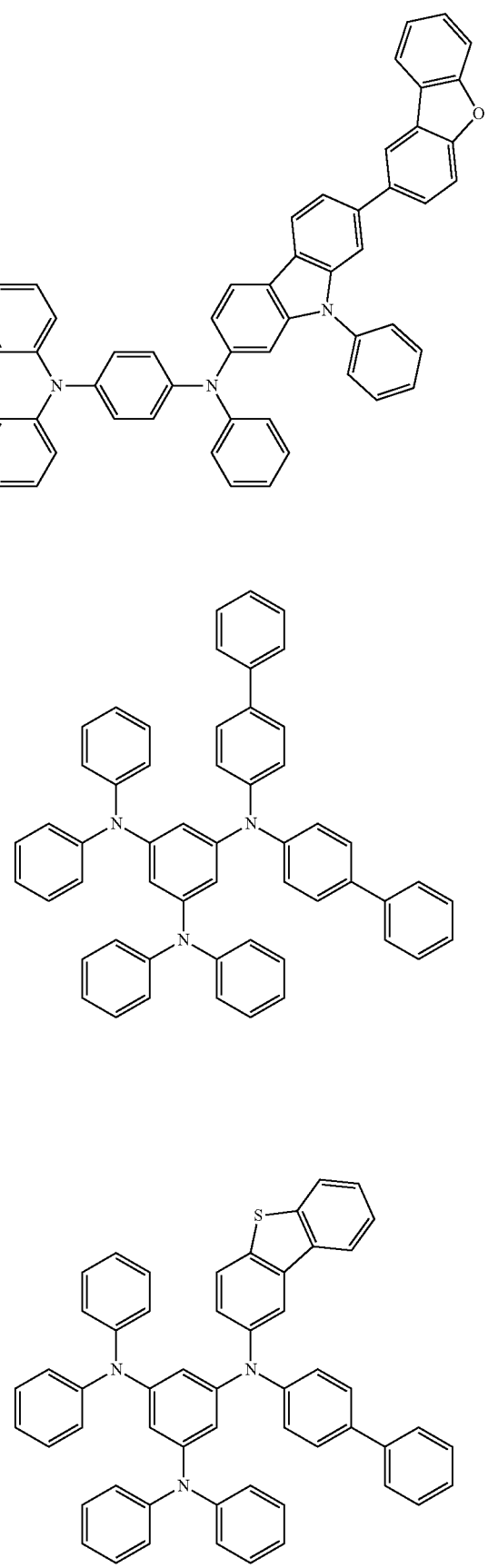

153
-continued
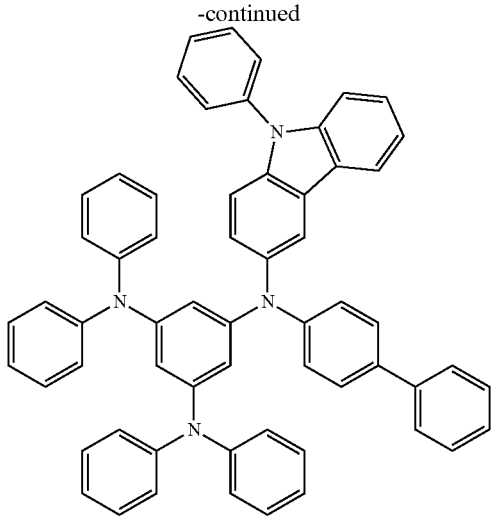
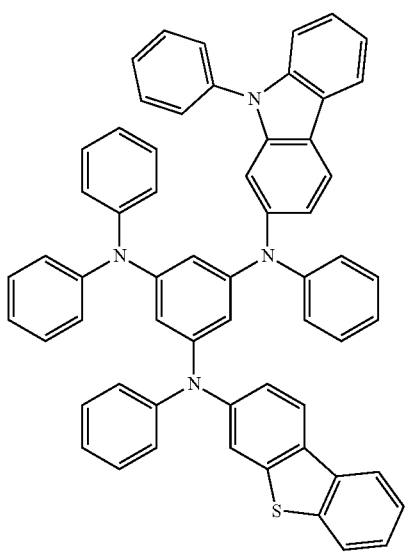
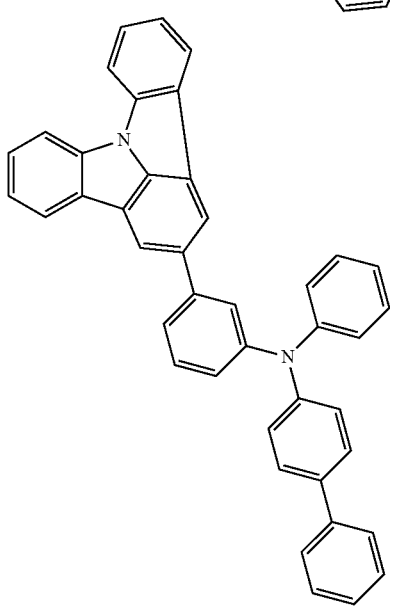
154
-continued
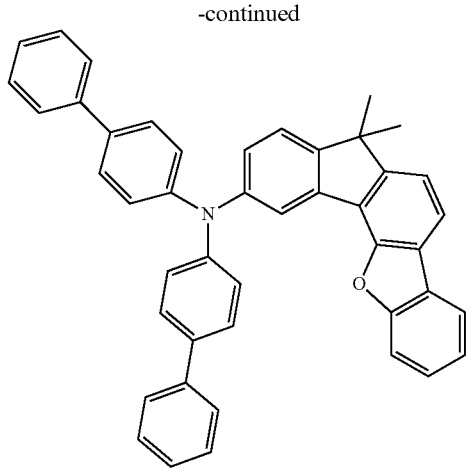
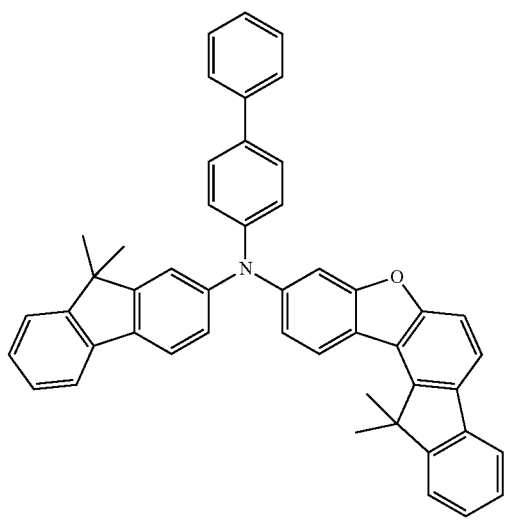
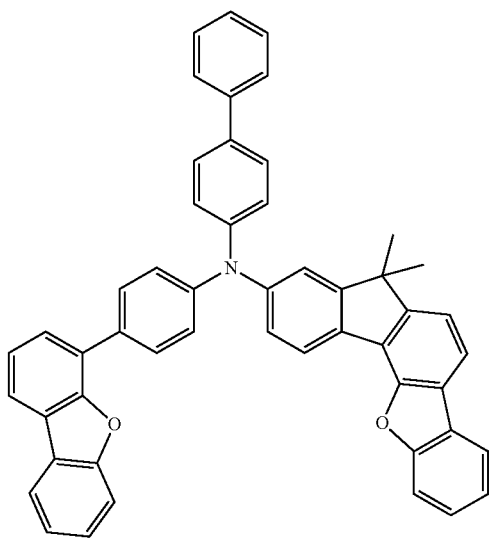

155
-continued
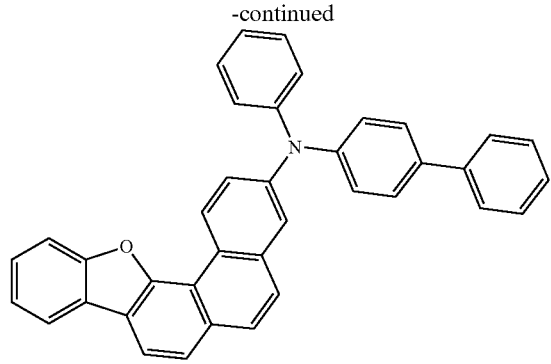
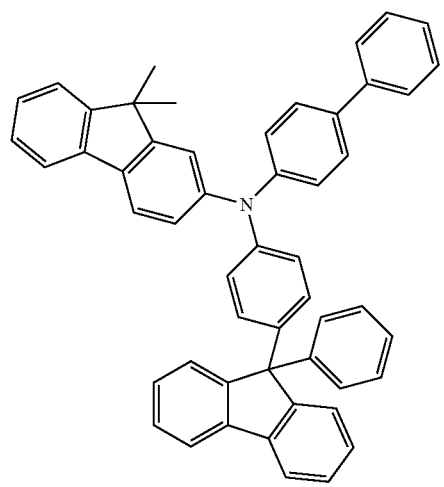
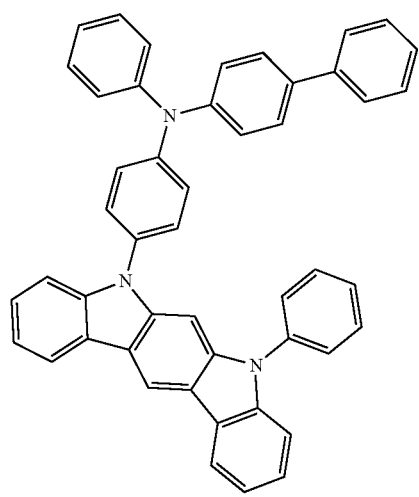
156
-continued
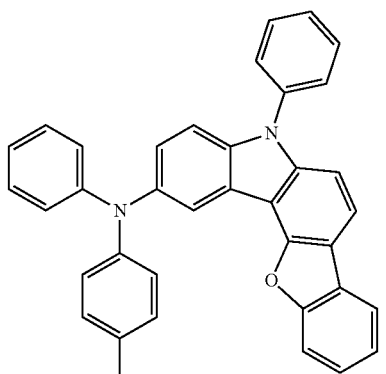
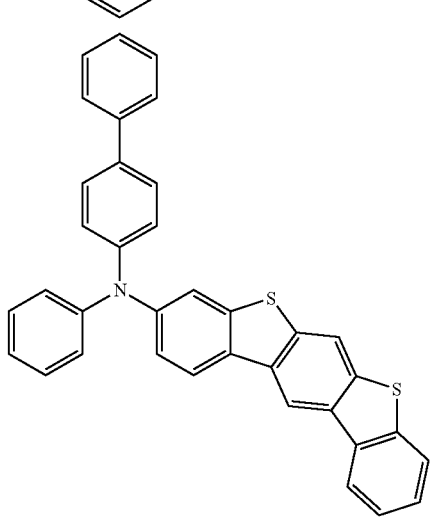
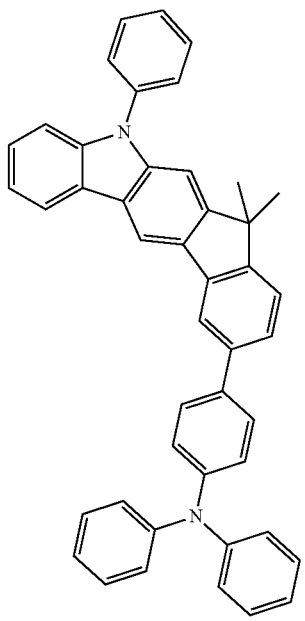

-continued

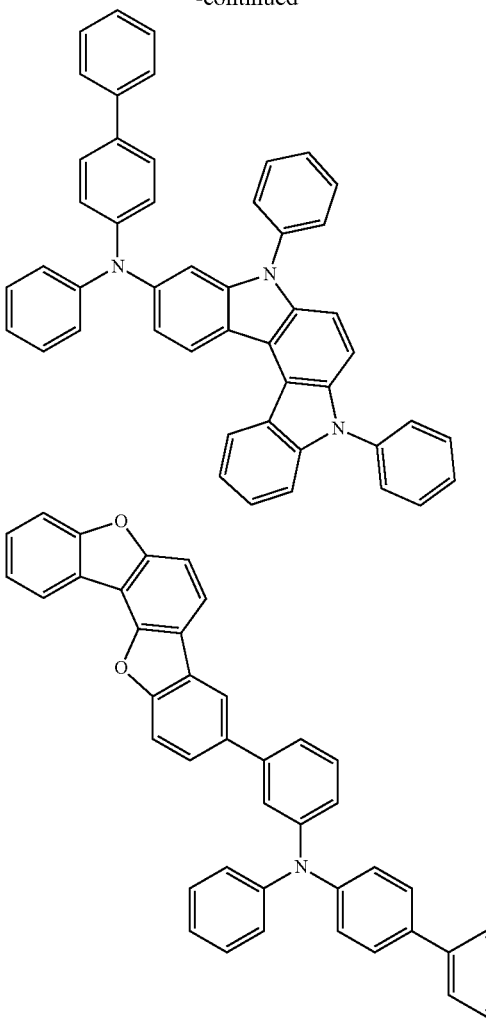

In the hole transport auxiliary layer, known compounds disclosed in U.S. Pat. No. 5,061,569 B2, which is incorporated by reference herein in its entirety for all purposes, JP1993-009471A, WO1995-009147A1, JP1995-126615A, JP1998-095972A, and the like and compounds similar thereto may be used in addition to the compound.

In an example embodiment, in FIG. 1 or 2, an organic light emitting diode may further include an electron transport layer, an electron injection layer, or a hole injection layer as the organic layer 105.

The organic light emitting diodes 100 and 200 may be manufactured by, for example, forming an anode or a cathode on a substrate, forming an organic layer using a dry film formation method such as a vacuum deposition method (evaporation), sputtering, plasma plating, and ion plating, and forming a cathode or an anode thereon.

The organic light emitting diode may be applied to an organic light emitting display device.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Hereinafter, starting materials and reactants used in the Examples and Synthesis Examples were purchased from Sigma-Aldrich Co. Ltd., TCI Inc. (Tokyo Chemical Industry), or P&H Tech as far as there in no particular comment, or were synthesized by known methods.

Preparation of Compound for Organic Optoelectronic Device

The compound as one specific examples was synthesized through the following procedure.

Preparation of First Compound

Core Synthesis 1

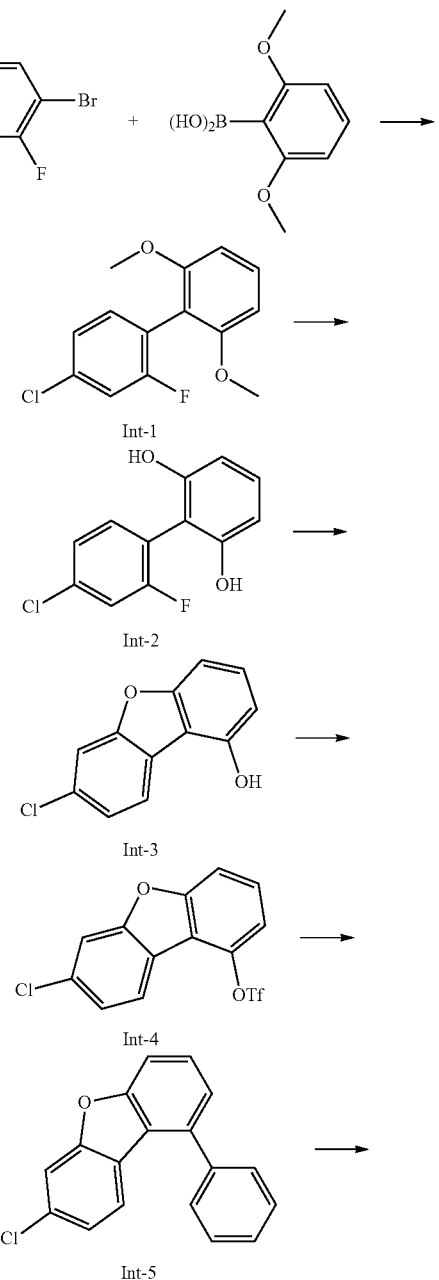

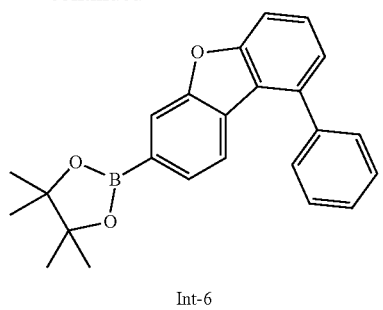

Int-6

Synthesis Example 1: Synthesis of Intermediate 1

[Reaction Scheme 1]

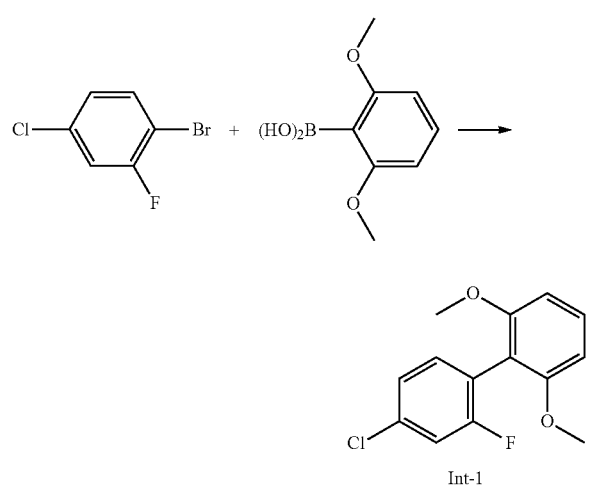

Int-1

1-bromo-4-chloro-2-fluorobenzene (61 g, 291 mmol), 2,6-dimethoxyphenylboronic acid (50.4 g, 277 mmol), $K_2CO_3$ (60.4 g, 437 mmol), and $Pd(PPh_3)_4$ (10.1 g, 8.7 mmol) were added into a round-bottomed flask and dissolved in THF (500 ml) and distilled water (200 ml) and then stirred under reflux at 60° C. for 12 hours. When the reaction was completed, an aqueous layer was removed to obtain 38 g (51%) of an intermediate 1 (Int-1) using a column chromatography (Hexane:DCM (20%)).

Synthesis Example 2: Synthesis of Intermediate 2

[Reaction Scheme 2]

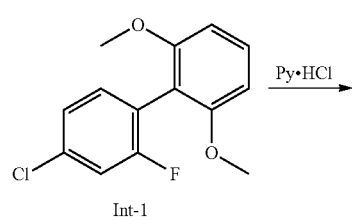

Int-1

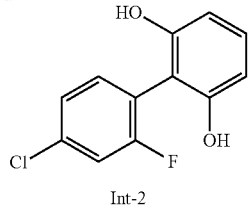

Int-2

The intermediate 1 (Int-1) (38 g, 142 mmol) and pyridine hydrochloride (165 g, 1425 mmol) were added into a round-bottomed flask and stirred under reflux at 200° C. for 24 hours. When the reaction was completed, it was cooled down at room temperature and then slowly poured into distilled water and stirred for 1 hour. The solid was filtered to provide 23 g (68%) of an intermediate 2 (Int-2).

Synthesis Example 3: Synthesis of Intermediate 3

[Reaction Scheme 3]

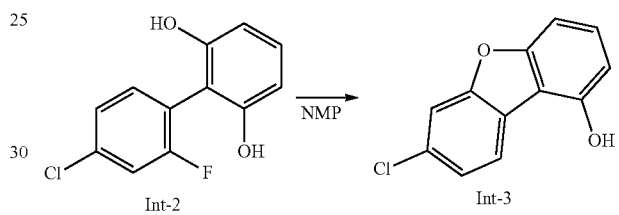

The intermediate 2 (Int-2) (23 g, 96 mmol) and $K_2CO_3$ (20 g, 144 mmol) were added into a round-bottomed flask and dissolved in NMP (100 ml) and stirred under reflux at 180° C. for 12 hours. When the reaction was completed, the mixture was poured into an excess amount of distilled water. The solid was filtered and dissolved in ethylacetate and then dried by $MgSO_4$, and an organic layer was removed under reduced pressure. Using a column chromatography (hexane: ethyl acetate (30%)), 16 g (76%) of an intermediate 3 (Int-3) was obtained.

Synthesis Example 4: Synthesis of Intermediate 4

[Reaction Scheme 4]

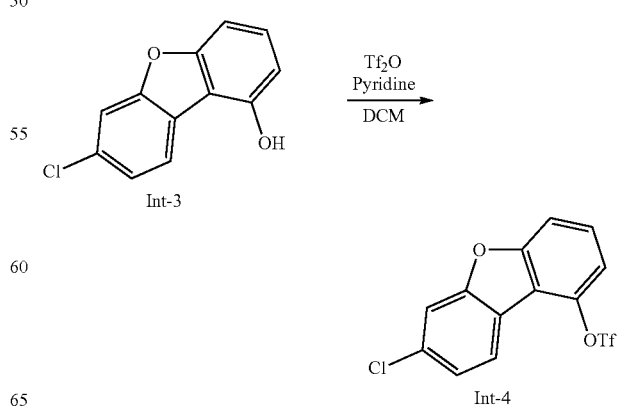

The intermediate 3 (Int-3) (16 g, 73 mmol) and pyridine (12 ml, 146 mmol) were added into a round-bottomed flask and dissolved in DCM (200 ml). The temperature was cooled down at 0° C. and then trifluoromethane sulfonic anhydride (14.7 ml, 88 mmol) was slowly added in a dropwise fashion. After stirring for 6 hours, when the reaction is completed, an excess amount of distilled water was added and stirred for 30 minutes, and then it was extracted by DCM. The organic solvent was removed under reduced pressure, and it was vacuum-dried to provide 22.5 g (88%) of an intermediate 4 (Int-4).

Synthesis Example 5: Synthesis of Intermediate 5

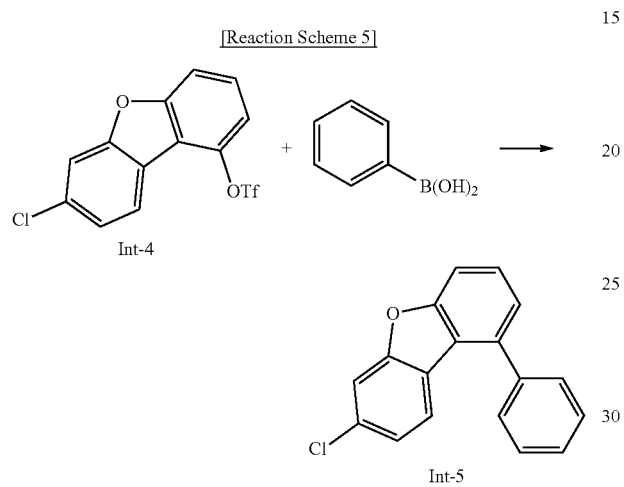

14.4 g (81%) of an intermediate 5 (Int-5) was obtained in accordance with the same procedure as in Synthesis Example 1, using the intermediate 4 (Int-4) (22.5 g, 64 mmol) and phenylboronic acid (7.8 g, 64 mmol), $K_2CO_3$ (13.3 g, 96 mmol), and $Pd(PPh_3)_4$ (3.7 g, 3.2 mmol).

Synthesis Example 6: Synthesis of Intermediate 6

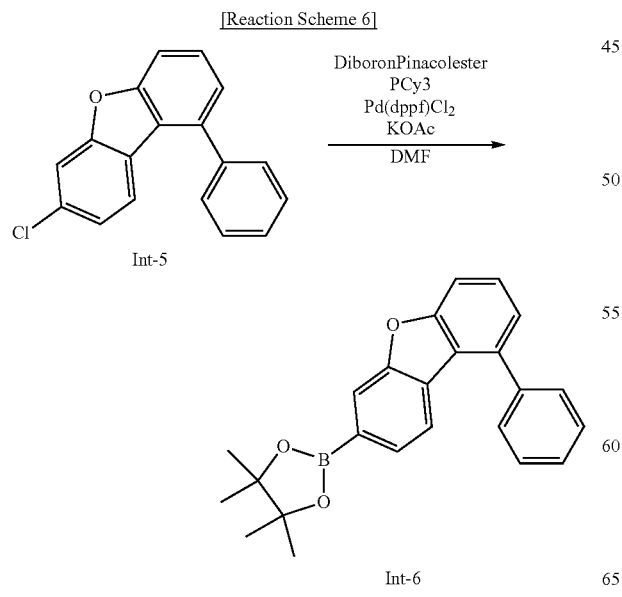

Intermediate 5 (Int-5) (22.5 g, 80 mmol), bis(pinacolato) diboron (24.6 g, 97 mmol), $Pd(dppf)Cl_2$ (2 g, 2.4 mmol), tricyclohexylphosphine (3.9 g, 16 mmol), and potassium acetate (16 g, 161 mmol) were added in a round-bottomed flask and dissolved by DMF (320 ml). The mixture was stirred under reflux at 120° C. for 10 hours. When the reaction is completed, the mixture was poured into excess amount of distilled water and stirred for 1 hour. The solid was filtered and dissolved in DCM. Moisture was removed by $MgSO_4$, and then an organic solvent was filtered using a silica gel pad and then removed under reduced pressure. The solid was recrystallized by ethyl acetate and hexane to provide a 26.9 g (90%) of intermediate 6 (Int-6).

Core Synthesis 2

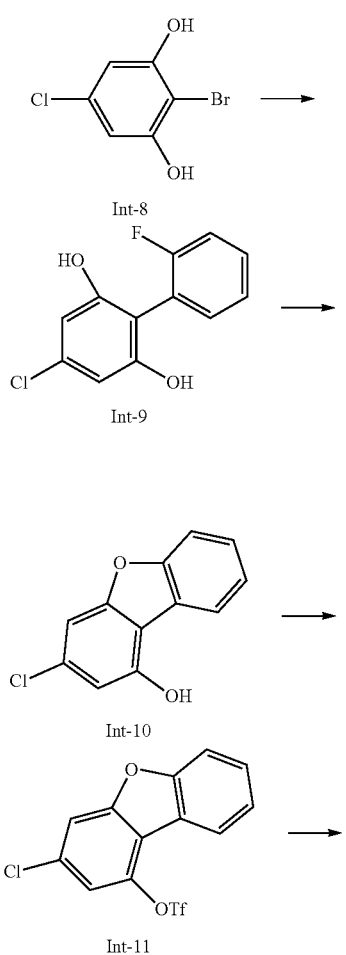

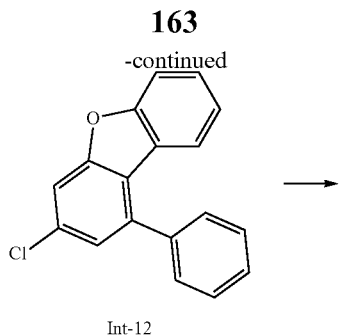

Int-12

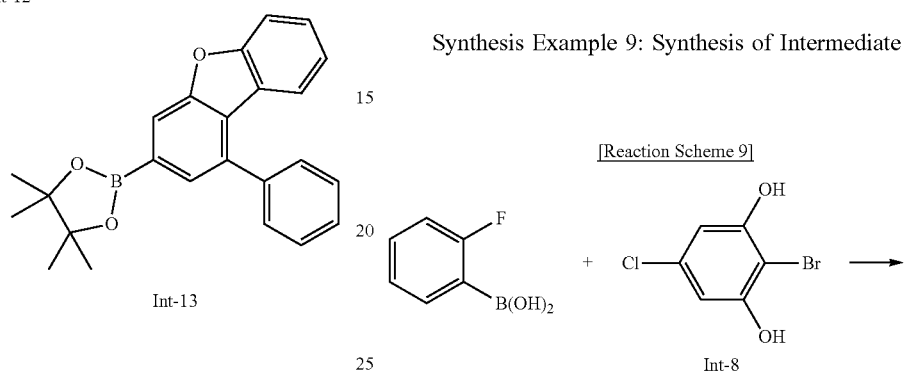

Int-13

Synthesis Example 7: Synthesis of Intermediate 7

[Reaction Scheme 7]

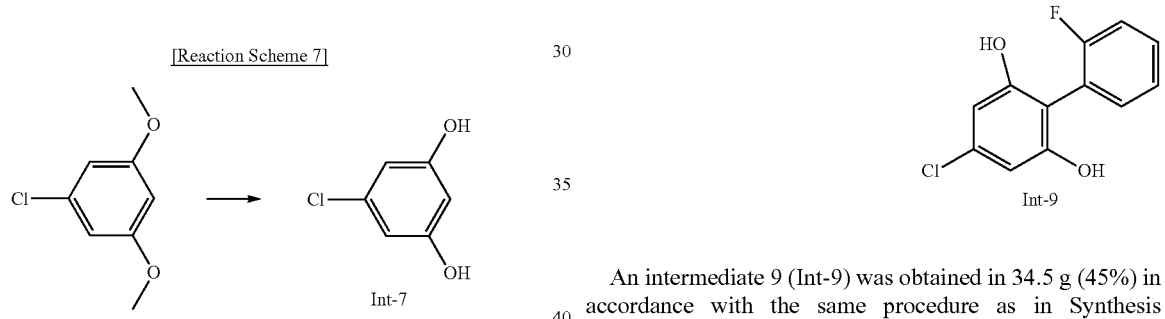

Int-7

1-chloro-3,5-dimethoxybenzene (70 g, 406 mmol) and pyridine hydrochloride (468 g, 4055 mmol) were added into a round-bottomed flask and stirred under reflux at 200° C. for 24 hours. When the reaction is completed, it was slowly poured into distilled water after cooling down at room temperature and stirred for 1 hour. The solid was filtered to provide 51.6 g (88%) of an intermediate 7 (Int-7).

Synthesis Example 8: Synthesis of Intermediate 8

[Reaction Scheme 8]

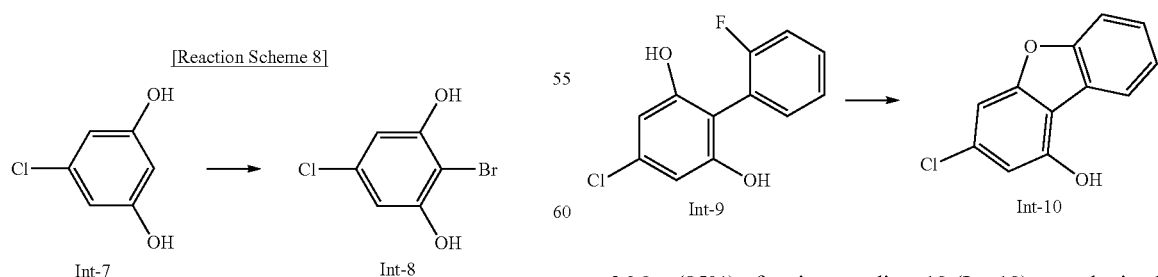

Int-7    Int-8

The intermediate 7 (Int-7) (51.6 g, 357 mmol) and p-toluenesulfonic acid monohydrate (6.8 g, 36 mmol) were added into a round-bottomed flask and dissolved by methanol (500 ml). A solution that N-bromosuccinide (NBS) (63.5 g, 357 mmol) was dissolved in methanol (1 L) was slowly added in a dropwise fashion under a condition of 0° C. for 30 minutes. After stirring at room temperature for 1 hour, when the reaction is completed, a saturation solution of sodium thiosulfate was poured into the mixed solution and stirred. DCM was added and extracted, and then the solvent was removed under reduced pressure. It was separated using a flash column chromatography to provide 72 g (90%) of an intermediate 8 (Int-8).

Synthesis Example 9: Synthesis of Intermediate 9

[Reaction Scheme 9]

Int-8

Int-9

An intermediate 9 (Int-9) was obtained in 34.5 g (45%) in accordance with the same procedure as in Synthesis Example 1, using 2-fluorophenylboronic acid (45 g, 322 mmol), the intermediate 8 (Int-8) (72 g, 322 mmol), $K_2CO_3$ (97.8 g, 708 mmol), and $Pd(PPh_3)_4$ (11.2 g, 9.7 mmol) in a round-bottomed flask under nitrogen atmosphere.

Synthesis Example 10: Synthesis of Intermediate 10

[Reaction Scheme 10]

Int-9    Int-10

26.9 g (85%) of an intermediate 10 (Int-10) was obtained in accordance with the same procedure as in Synthesis Example 3, after adding the intermediate 9 (Int-9) (34.5 g, 145 mmol) and $K_2CO_3$ (26 g, 188 mmol) into a round-bottomed flask and dissolving the same in NMP (450 ml).

Synthesis Example 11: Synthesis of Intermediate 11

[Reaction Scheme 11]

Int-10 → Int-11

The intermediate 10 (Int-10) (26.9 g, 123 mmol) and pyridine (20 ml, 246 mmol) were added into a round-bottomed flask and dissolved in DCM (300 ml). After cooling down at a temperature of 0° C., trifluoromethanesulfonic anhydride (24.7 ml, 148 mmol) was slowly added in a dropwise fashion. After stirring for 6 hours, when the reaction was completed, an excess amount of distilled water was added thereto and stirred for 30 minutes, then it was extracted by DCM. An organic solvent was removed under reduced pressure and vacuum-dried to obtain 36.2 g (84%) of an intermediate 11 (Int-11).

Synthesis Example 12: Synthesis of Intermediate 12

[Reaction Scheme 12]

Int-11 + (HO)₂B-Ph → Int-12

An intermediate 12 (Int-12) was obtained in 25.9 g (90%) in accordance with the same procedure as in Synthesis Example 1, using the intermediate 11 (Int-11) (36.2 g, 103 mmol) and phenylboronic acid (12.6 g, 103 mmol), K₂CO₃ (21.4 g, 155 mmol), and Pd(PPh₃)₄ (5.9 g, 5 mmol).

Synthesis Example 13: Synthesis of Intermediate 13

[Reaction Scheme 13]

Int-12 →

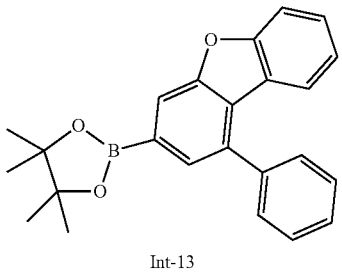

Int-13

An intermediate 13 (Int-13) was obtained in 25.8 g (75%) in accordance with the same procedure as in Synthesis Example 6, except that the intermediate 12 (Int-12) (25.9 g, 93 mmol), bis(pinacolato)diboron (28.3 g, 112 mmol), Pd(dppf)Cl₂ (2.3 g, 2.8 mmol), tricyclohexylphosphine (4.5 g, 18.6 mmol), and potassium acetate (18.2 g, 186 mmol) were added in a round-bottomed flask and dissolved by DMF (350 ml).

Synthesis Example 14: Synthesis of Intermediate 14

[Reaction Scheme 14]

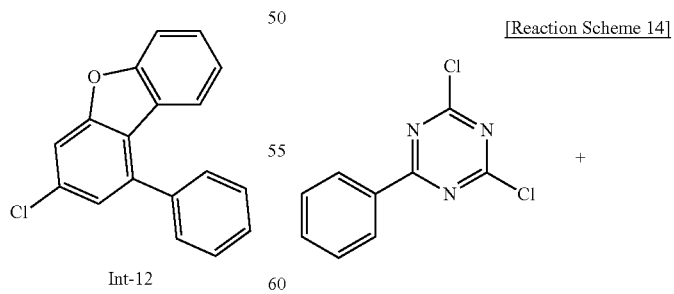

167
-continued

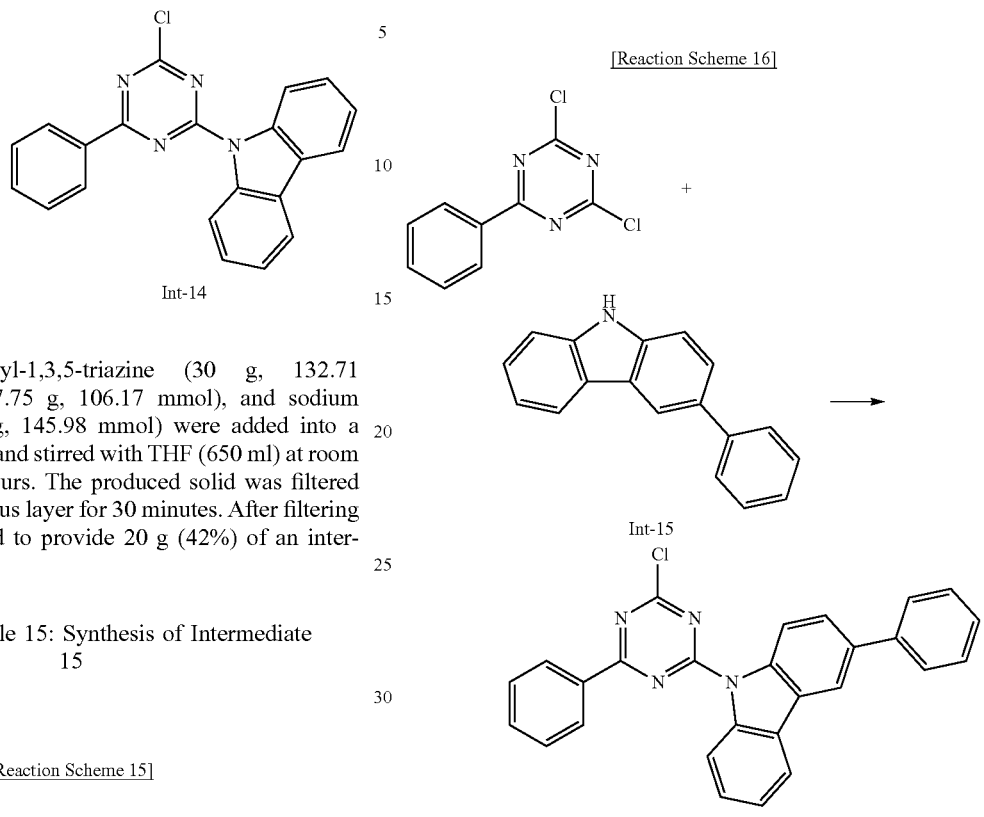

Int-14

2,4-dichloro-6-phenyl-1,3,5-triazine (30 g, 132.71 mmol), carbazole (17.75 g, 106.17 mmol), and sodium tert-butoxide (14.03 g, 145.98 mmol) were added into a round-bottomed flask and stirred with THF (650 ml) at room temperature for 12 hours. The produced solid was filtered and stirred in an aqueous layer for 30 minutes. After filtering the same, it was dried to provide 20 g (42%) of an intermediate 14 (Int-14).

Synthesis Example 15: Synthesis of Intermediate 15

[Reaction Scheme 15]

Int-15

3-Bromocarbazole (15 g, 60.95 mmol), phenylboronic acid (11.44 g, 73.14 mmol), K$_2$CO$_3$ (21.06 g, 152.38 mmol), and Pd(PPh$_3$)$_4$ (3.52 g, 3.05 mmol) were added into a round-bottomed flask, and dissolved together with THF (200 ml) in distilled water (75 ml) and stirred under reflux at 60° C. for 12 hours. When the reaction is completed, after removing an aqueous layer, an intermediate 15 (Int-15) was obtained in 12.3 g (83%) using a column chromatography (Hexane:DCM (20%)).

168

Synthesis Example 16: Synthesis of Intermediate 16

[Reaction Scheme 16]

Int-15

Int-16

An Intermediate 16 (Int-16) was obtained in 28 g (49%) in accordance with the same procedure as in Synthesis Example 14, using 2,4-dichloro-6-phenyl-1,3,5-triazine (30 g, 132.71 mmol), the intermediate 15 (Int-15) (25.83 g, 106.17 mmol), and sodium tert-butoxide (14.03 g, 145.98 mmol).

Synthesis Example 17: Synthesis of Intermediate 17

[Reaction Scheme 17]

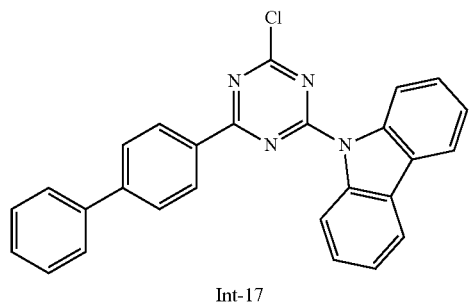

Int-17

An intermediate 17 (Int-17) was obtained in 31 g (54%) in accordance with the same procedure as in Synthesis Example 14, using 2,4-dichloro-6-(biphenyl-4-yl)-1,3,5-triazine (40 g, 132.38 mmol), carbazole (15.49 g, 92.67 mmol), and sodium tert-butoxide (15.00 g, 145.62 mmol).

Synthesis Example 18: Synthesis of Intermediate 18

[Reaction Scheme 18]

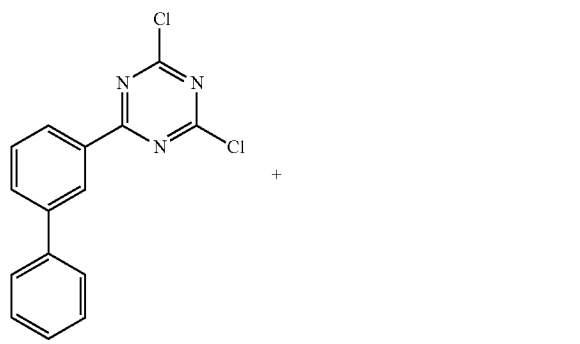

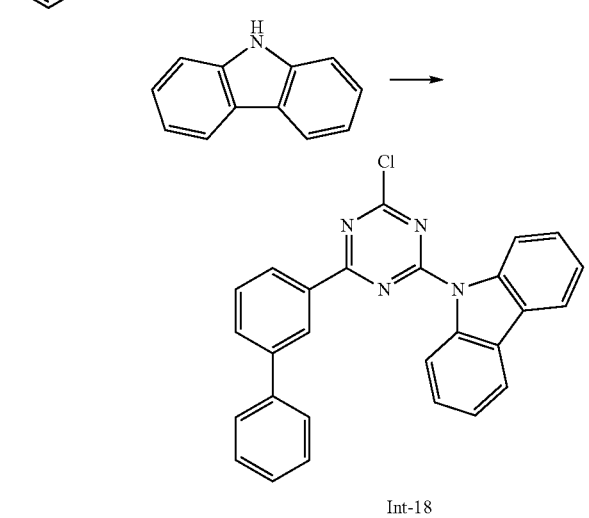

Int-18

An intermediate 18 (Int-18) was obtained in 29 g (51%) in accordance with the same procedure as in Synthesis Example 14, using 2,4-dichloro-6-(biphenyl-3-yl)-1,3,5-triazine (40 g, 132.38 mmol), carbazole (15.49 g, 92.67 mmol), and sodium tert-butoxide (15.00 g, 145.62 mmol).

Synthesis Example 19: Synthesis of Intermediate 19

[Reaction Scheme 19]

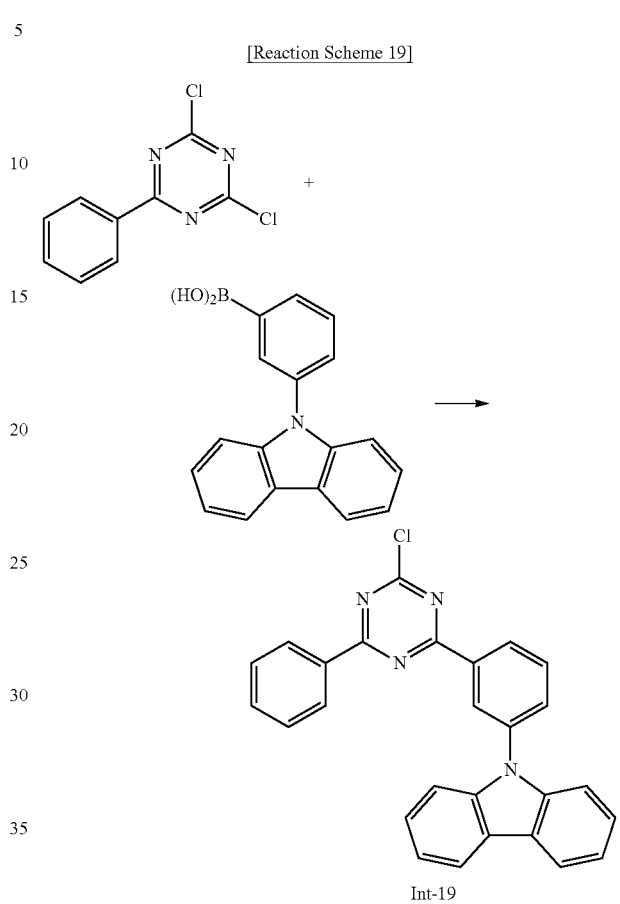

Int-19

2,4-dichloro-6-phenyl-1,3,5-triazine (19.5 g, 86.26 mmol), (3-(carbazole-9H)phenyl)pinacol ester (35.04 g, 94.89 mmol), $K_2CO_3$ (23.84 g, 172.52 mmol) and $Pd(PPh_3)_4$ (2.99 g, 2.59 mmol) were added into a round-bottomed flask and dissolved in distilled water (85 ml) together with THF (250 ml) and stirred under reflux at 60° C. for 12 hours. When the reaction is completed, after removing an aqueous layer, and an intermediate 19 (Int-19) was obtained in 24.68 g (66%) using a column chromatography (Hexane:DCM (30%)).

Synthesis Example 20: Synthesis of Compound A-1

[Reaction Scheme 20]

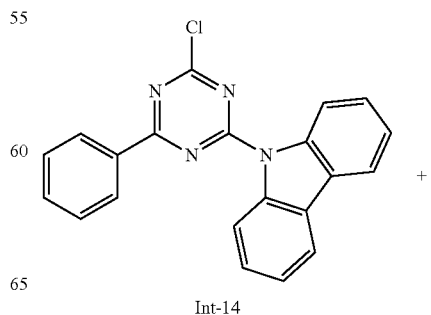

Int-14

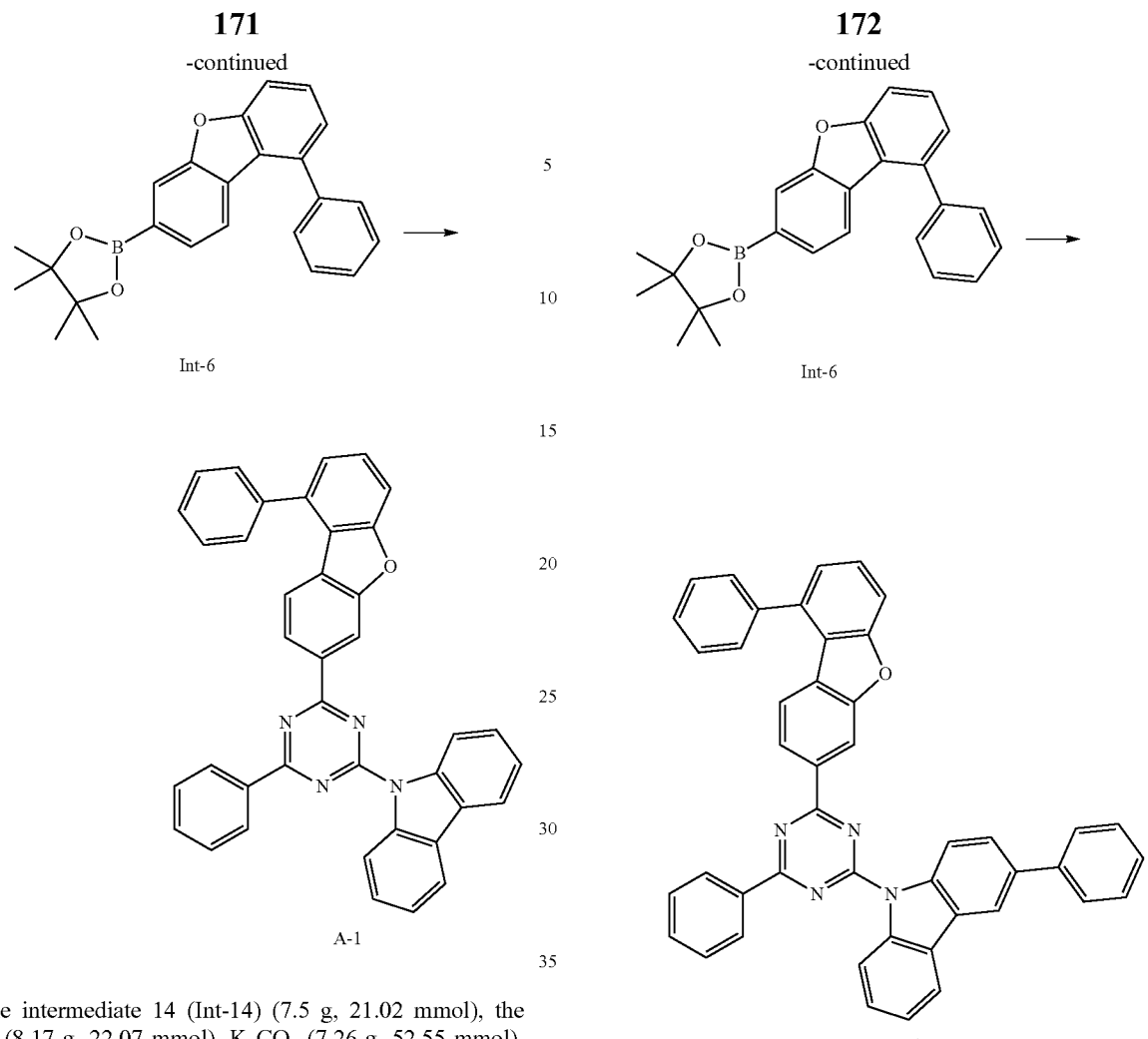

Int-6

A-1

The intermediate 14 (Int-14) (7.5 g, 21.02 mmol), the Int-6 (8.17 g, 22.07 mmol), K$_2$CO$_3$ (7.26 g, 52.55 mmol), and Pd(PPh$_3$)$_4$ (1.21 g, 1.05 mmol) were added into a round-bottomed flask and dissolved in distilled water (40 ml) and stirred under reflux at 70° C. for 12 hours. When the reaction was completed, after filtering a solid crystallized by adding the mixture into 500 mL of methanol, it was dissolved in monochlorobenzene and filtered by a silica gel/celite, and an appropriate amount of an organic solvent was removed, and then it was recrystallized by methanol to provide 8.0 g (67%) of Compound A-1.

Synthesis Example 21: Synthesis of Compound A-4

[Reaction Scheme 21]

Int-16

Int-6

A-4

Compound A-4 (15.3 g, yield of 76%) was obtained in accordance with the same procedure as in Synthesis Example 20, except that the intermediate agent was changed.

Synthesis Example 22: Synthesis of Compound A-6

[Reaction Scheme 22]

Int-18

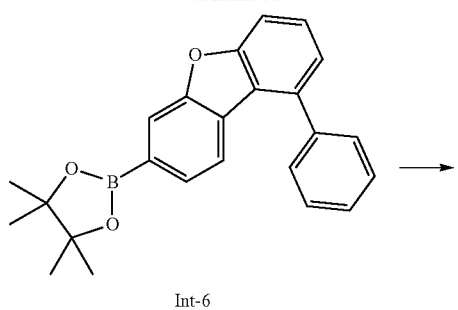

Int-6

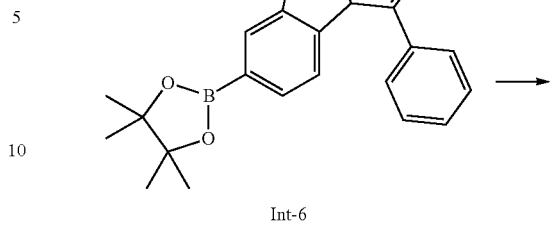

Int-6

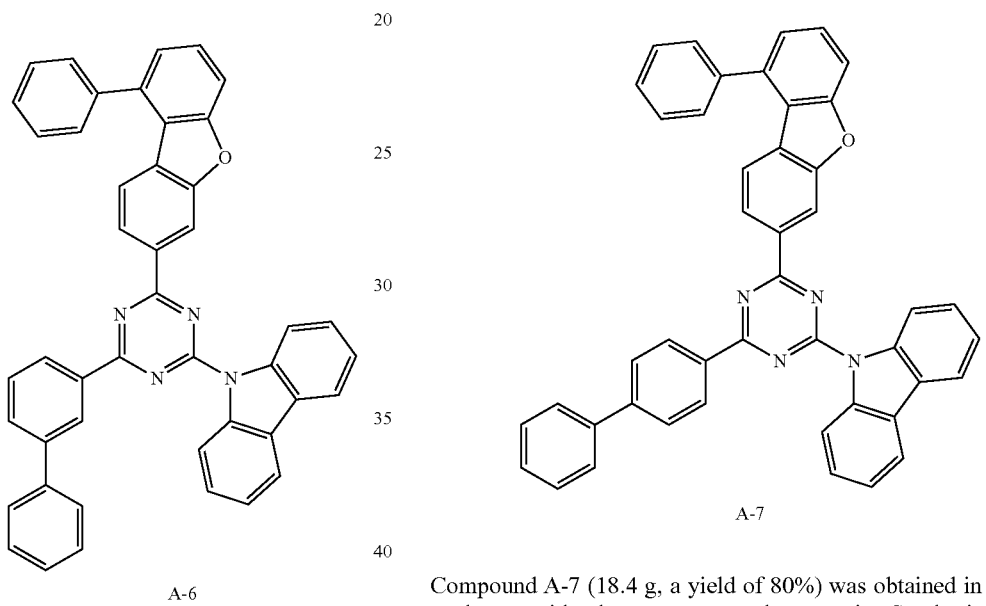

A-6

A-7

Compound A-6 (12.6 g, yield of 79%) was obtained in accordance with the same procedure as in Synthesis Example 20, except the intermediate agent was changed.

Compound A-7 (18.4 g, a yield of 80%) was obtained in accordance with the same procedure as in Synthesis Example 20, except the intermediate agent was changed.

Synthesis Example 23: Synthesis of Compound A-7

Synthesis Example 24: Synthesis of Compound A-11

[Reaction Scheme 23]

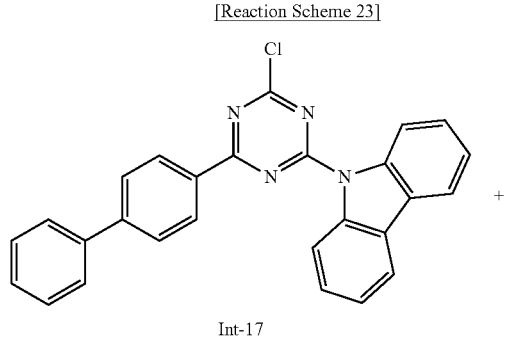

Int-17

[Reaction Scheme 24]

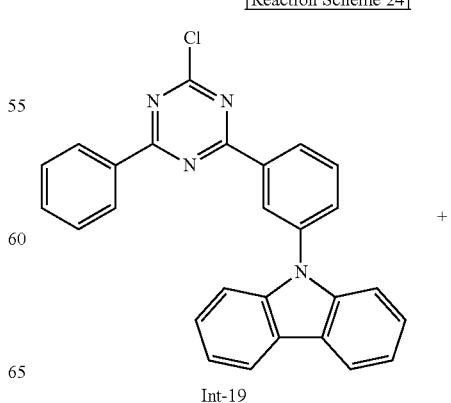

Int-19

-continued

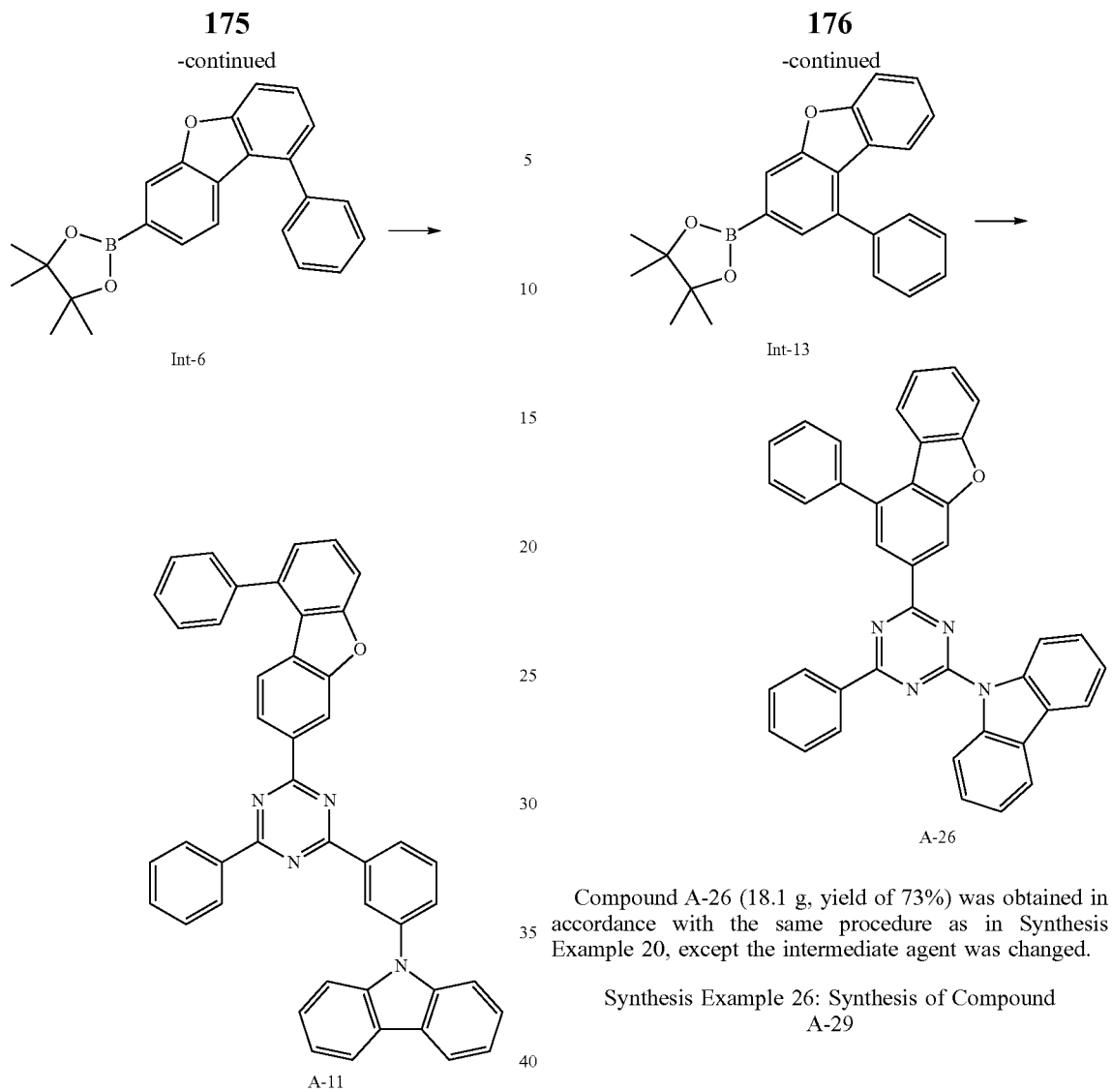

Compound A-11 (11.6 g, yield of 71%) was obtained in accordance with the same procedure as in Synthesis Example 20, except the intermediate agent was changed.

Synthesis Example 25: Synthesis of Compound A-26

[Reaction Scheme 25]

Compound A-26 (18.1 g, yield of 73%) was obtained in accordance with the same procedure as in Synthesis Example 20, except the intermediate agent was changed.

Synthesis Example 26: Synthesis of Compound A-29

[Reaction Scheme 26]

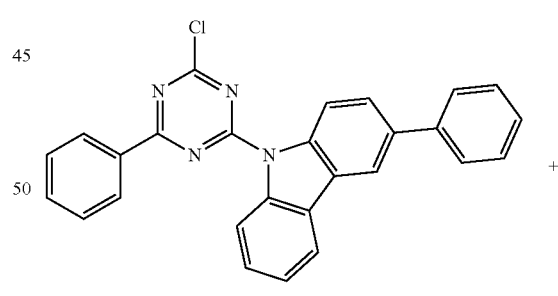

-continued

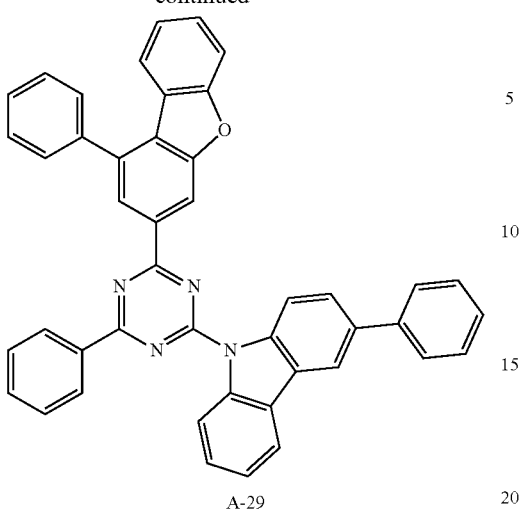

A-29

Compound A-29 (11.1 g, yield of 69%) was obtained in accordance with the same procedure as in Synthesis Example 20, except the intermediate agent was changed.

Synthesis Example 27: Synthesis of Compound A-31

[Reaction Scheme 27]

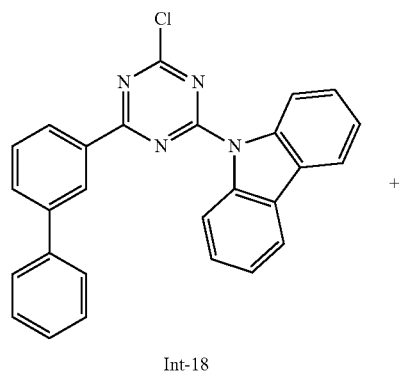

Int-18

+

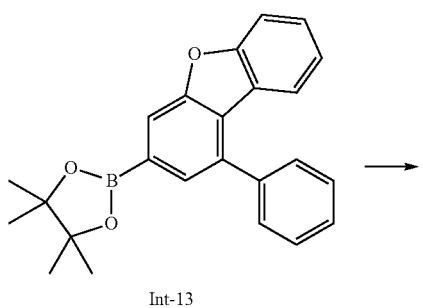

Int-13 →

-continued

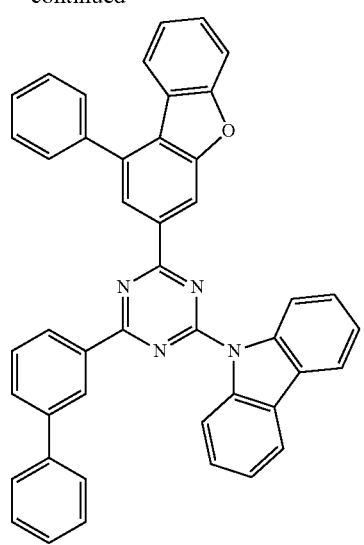

A-31

Compound A-31 (14.9 g, yield of 76%) was obtained in accordance with the same procedure as in Synthesis Example 20, except the intermediate agent was changed.

Synthesis Example 28: Synthesis of Compound A-32

[Reaction Scheme 28]

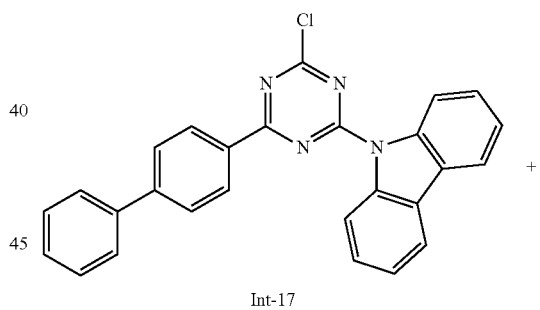

Int-17

+

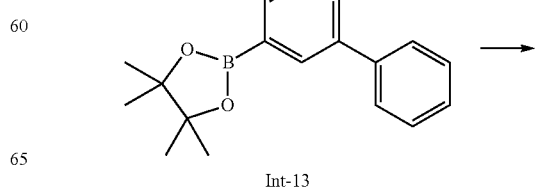

Int-13 →

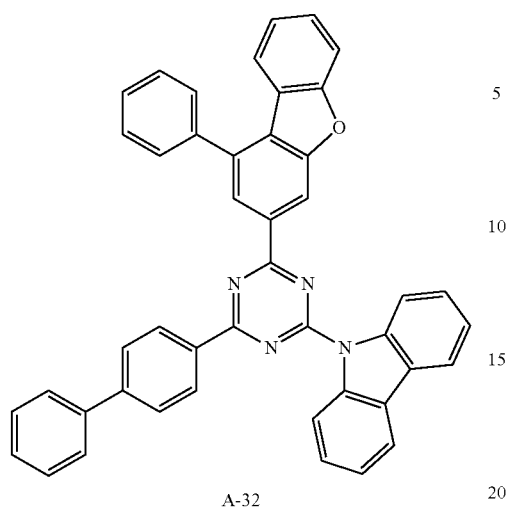

A-32

Compound A-32 (14.5 g, yield of 77%) was obtained in accordance with the same procedure as in Synthesis Example 20, except the intermediate agent was changed.

Synthesis Example 29: Synthesis of Compound A-36

[Reaction Scheme 29]

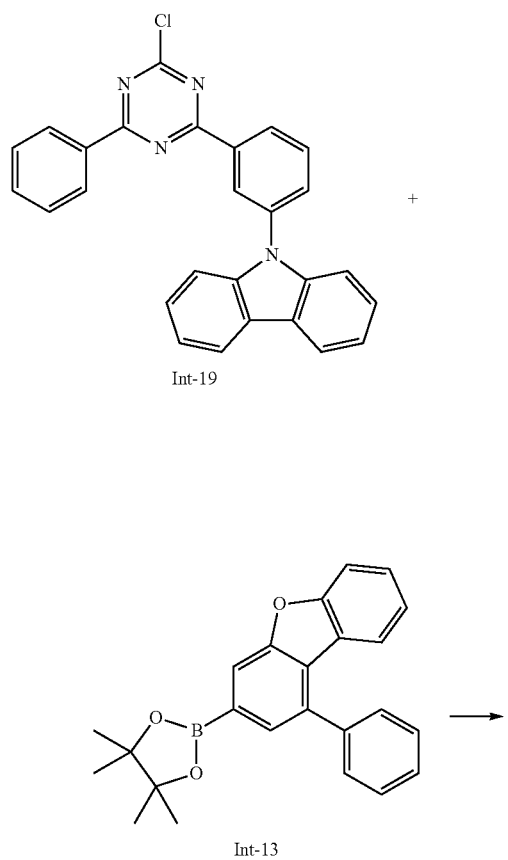

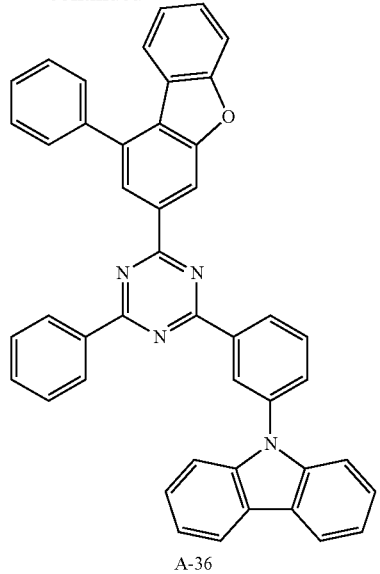

A-36

Compound A-36 (13.6 g, yield of 79%) was obtained in accordance with the same procedure as in Synthesis Example 20, except the intermediate agent was changed.

Preparation of Second Compound

Compound B-99 was synthesized in accordance with the same procedure as disclosed in U.S. 2017/0317293 A1, which is incorporated by reference herein in its entirety for all purposes.

Comparative Synthesis Example 1: Synthesis of Compound H-1

[Reaction Scheme 30]

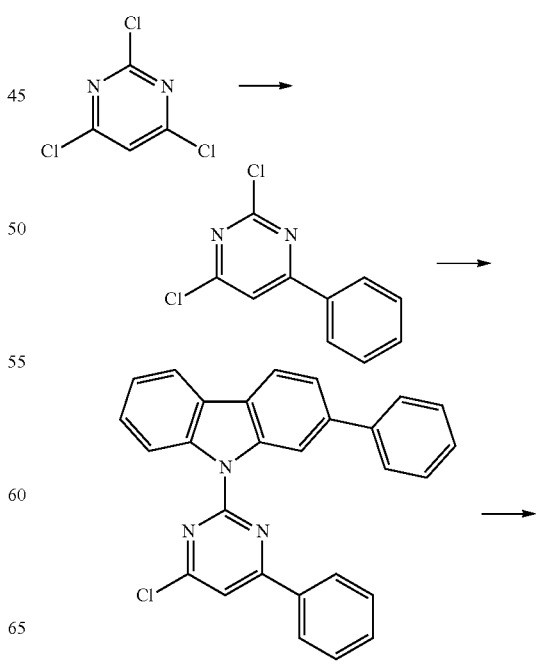

-continued

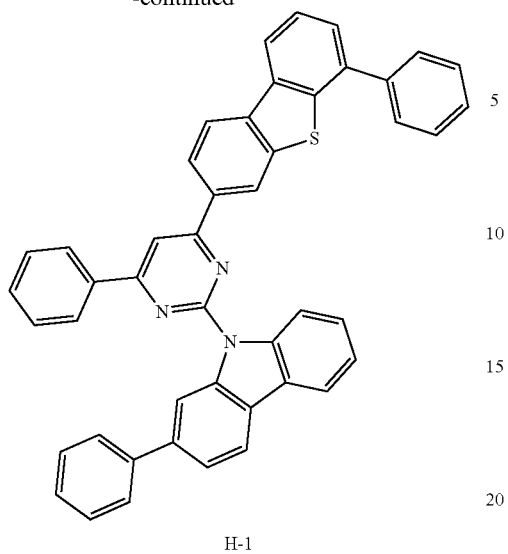

H-1

Compound H-1 was synthesized in accordance with the same procedure as disclosed in KR2014-0144550, except that the intermediate agent was changed.

Comparative Synthesis Example 2: Synthesis of Compound H-2

Compound H-2 was synthesized in accordance with the same procedure as disclosed in WO2013-077362, except that the intermediate agent was changed.

Comparative Synthesis Example 3: Synthesis of Compound H-3

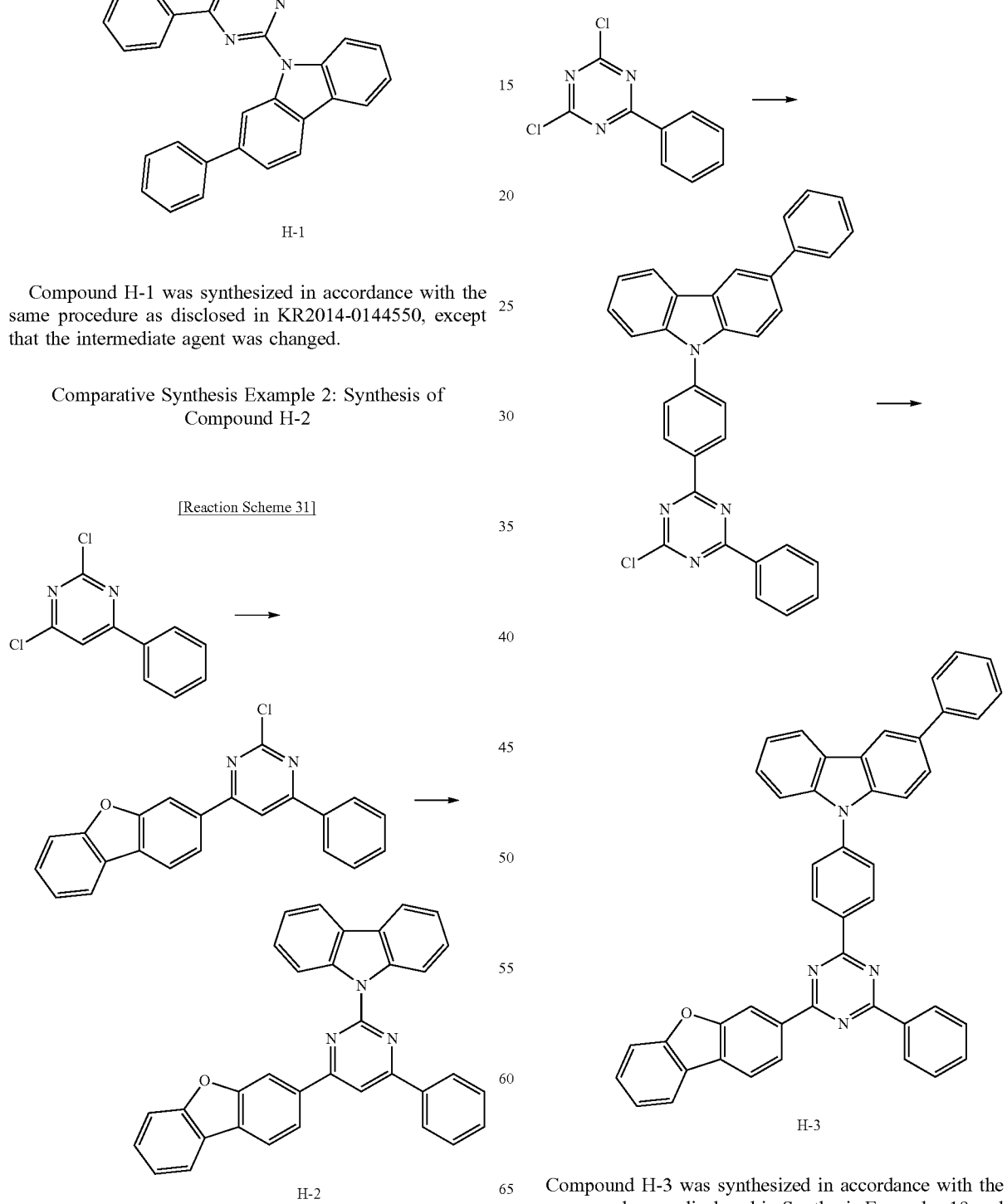

Compound H-3 was synthesized in accordance with the same procedure as disclosed in Synthesis Examples 19 and 20, except that the intermediate agent was changed.

Manufacture of Organic Light Emitting Diode

Example 1

A glass substrate coated with ITO (indium tin oxide) as a 1500 Å-thick thin film was washed with distilled water. After washing with the distilled water, the glass substrate was ultrasonic wave-washed with a solvent such as isopropyl alcohol, acetone, methanol, and the like and dried and then, moved to a plasma cleaner, cleaned by using oxygen plasma for 10 minutes, and moved to a vacuum depositor. This obtained ITO transparent electrode was used as an anode, Compound A was vacuum-deposited on the ITO substrate to form a 700 Å-thick hole injection layer, Compound B was deposited to be 50 Å thick on the injection layer, and Compound C was deposited to be 1020 Å thick to form a hole transport layer. On the hole transport layer, a 400 Å-thick light emitting layer was formed by vacuum-depositing Compound A-1 of Synthesis Example 20 as a host and 7 wt % of PhGD as a dopant. Subsequently, on the light emitting layer, a 300 Å-thick electron transport layer was formed by simultaneously vacuum-depositing the compound D and Liq in a ratio of 1:1, and on the electron transport layer, Liq and Al were sequentially vacuum-deposited to be 15 Å thick and 1200 Å thick, manufacturing an organic light emitting diode.

The organic light emitting diode had a five-layered organic thin layer, and specifically the following structure.

ITO/Compound A (700 Å)/Compound B (50 Å)/Compound C (1020 Å)/EML[Compound A-1:PhGD (7 wt %)](400 Å)/Compound D:Liq (300 Å)/Liq (15 Å)/Al (1200 Å).

Compound A: N4,N4'-diphenyl-N4,N4'-bis(9-phenyl-9H-carbazol-3-ye)biphenyl-4,4'-diamine Compound B: 1,4,5,8,9,11-hexaazatriphenylene-hexacarbonitrile (HAT-CN)

Compound C:N-(biphenyl-4-yl)-9,9-dimethyl-N-(4-(9-phenyl-9H-carbazol-3-yl)phenyl)-9H-fluoren-2-amine Compound D: 8-(4-(4,6-di(naphthalen-2-yl)-1,3,5-triazin-2-yl)phenyl)quinoline

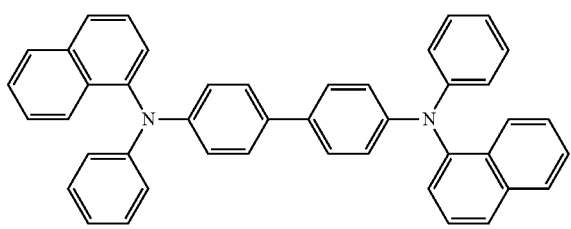

[NPB]

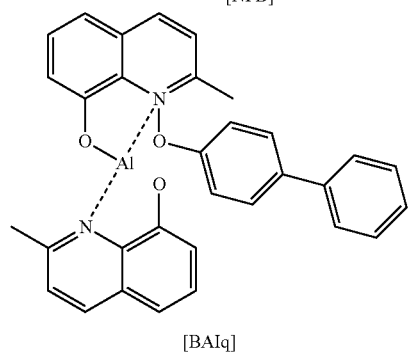

[BAlq]

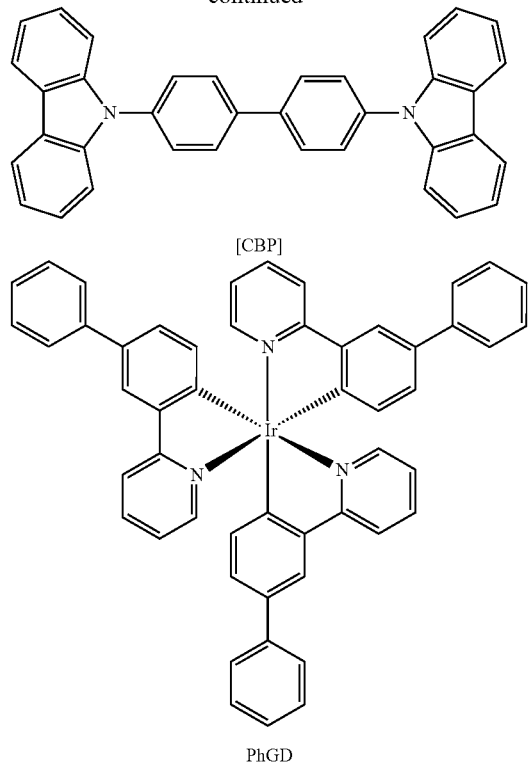

[CBP]

PhGD

Examples 2 to 15 and Comparative Examples 1 to 4

Each organic light emitting diode was manufactured according to the same method as Example 1 except for changing compositions as shown in Table 1 and Table 2.

Evaluation

Driving voltages, luminous efficiency, and life-span characteristics of the organic light emitting diodes according to Examples 1 to 15 and Comparative Examples 1 to 4 were evaluated.

Specific measurement methods are as follows, and the results are shown in Table 1 and Table 2.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltages of the organic light emitting diodes were increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

(4) Measurement of Life-span

The results were obtained by measuring a time when current efficiency (cd/A) was decreased down to 95%, while luminance (cd/m$^2$) was maintained to be 24000 cd/m$^2$.

(5) Measurement of Driving Voltage

A driving voltage of each diode was measured using a current-voltage meter (Keithley 2400) at 15 mA/cm$^2$.

(6) Calculation of T95 Life-Span Ratio (%)

A relative ratio of T95(h) of a single host (ratio of Examples to Comparative Example of reference data) or mixed host applied with the same second host (ratio of Examples (including a first compound as a first host) to Comparative Example of reference data (including a comparative compound as a first host)) was shown.

T95 life-span ratio (%)={[T95(h) of Examples or Comparative Examples (single host or a mixed host applied with a first compound)]/[T95(h) of reference data (single or mixed host of comparative compound)]}×100

(7) Calculation of Driving Voltage Ratio (%)

A relative ratio of driving voltage of a single host (ratio of Examples to Comparative Example of reference data) or mixed host applied with the same second host (ratio of Examples (including a first compound as a first host) to Comparative Example of reference data (including a comparative compound as a first host)) was shown.

Driving Voltage Ratio (%)={[driving voltage (V) of Examples or Comparative Examples (single or mixed host applied with a first compound)]/[driving voltage (V) of reference data (single or mixed host of comparative compound)]}×100

(8) Calculation of Power Efficiency Ratio (%)

A relative ratio of a single host (ratio of Examples to Comparative Example of reference data) or mixed host applied with the same second host (ratio of Examples (including a first compound as a first host) to Comparative Example of reference data (including a comparative compound as a first host)) was shown.

Ratio of Power Efficiency (%)={[Power efficiency (Cd/A) of Examples or Comparative Examples (single or mixed host applied with a first compound)]/[Power efficiency (Cd/A) of reference data (single or mixed host of a comparative compound)]}×100

TABLE 1

| Nos. | Host | Color | Ratio of driving voltages (%) | Ratio of power Efficiency (%) | T95 Life-span Ratio (%) |
|---|---|---|---|---|---|
| Example 1 | A-1 | green | 97% | 150% | 190% |
| Example 2 | A-4 | green | 98% | 148% | 191% |
| Example 3 | A-6 | green | 101% | 145% | 173% |
| Example 4 | A-7 | green | 95% | 143% | 162% |
| Example 5 | A-11 | green | 100% | 142% | 145% |
| Example 6 | A-26 | green | 95% | 147% | 165% |
| Example 7 | A-29 | green | 96% | 145% | 168% |
| Example 8 | A-31 | green | 100% | 146% | 147% |
| Example 9 | A-32 | green | 94% | 145% | 145% |
| Example 10 | A-36 | green | 98% | 140% | 130% |
| Comparative Example 1 | H-1 | green | 150% | 115% | 32% |
| Comparative Example 2 | H-2 | green | 115% | 120% | 45% |
| Comparative Example 3 (reference data) | H-3 | green | 100% | 100% | 100% |

TABLE 2

| Nos. | Host First compound | Second compound | Weight ratio (First compound: Second compound) | Ratio of power Efficiency (%) | T95 Life-span Ratio (%) |
|---|---|---|---|---|---|
| Example 11 | A-1 | B-99 | 7:3 | 105% | 218% |
| Example 12 | A-4 | B-99 | 7:3 | 103% | 227% |
| Example 14 | A-7 | B-99 | 7:3 | 101% | 205% |
| Example 15 | A-11 | B-99 | 7:3 | 102% | 191% |
| Comparative Example 4 (reference data) | H-3 | B-99 | 7:3 | 100 | 100 |

Without being bound by theory, referring to Tables 1 and 2, structures of Comparative Examples 2, 3, and 4 were similar to the structure in terms of substitution with dibenzofuran, but a material where dibenzofuran substituted with aryl at No. 1 position may have significantly changed molecular properties and stability and remarkably increased life-span. In addition, referring to results of Comparative Examples 1 and 2, a structure having triazine showed significantly improved driving voltages and life-span characteristics due to significantly improved charge stability and electron transport characteristics compared with a structure having pyrimidine.

By way of summation and review, an organic light emitting diode (OLED) has recently drawn attention due to an increase in demand for flat panel displays. The organic light emitting diode converts electrical energy into light by applying current to an organic light emitting material. Performance of an organic light emitting diode may be affected by organic materials disposed between electrodes.

As described above, embodiments may provide a compound for an organic optoelectronic device capable of realizing an organic optoelectronic device having high efficiency and a long life-span.

DESCRIPTION OF SYMBOLS 100, 200: organic light emitting diode

105: organic layer

110: cathode

120: anode

130: light emitting layer

140: hole auxiliary layer

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope as set forth in the following claims.

What is claimed is:

1. A compound represented by a combination of Chemical Formula 1 and Chemical Formula 2 bonded together:

[Chemical Formula 1]

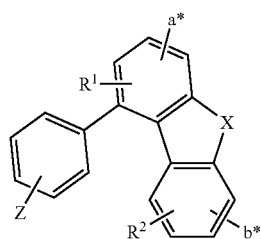

[Chemical Formula 2]

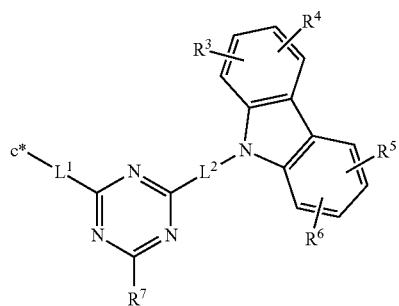

wherein, in Chemical Formula 1 and Chemical Formula 2,

X is O or S,

Z is hydrogen, deuterium, a substituted or unsubstituted C1 to C10 alkyl group, or a substituted or unsubstituted phenyl group, $L^1$ and $L^2$ are each independently a single bond, or a substituted or unsubstituted C6 to C20 arylene group, one of a* and b* of Chemical Formula 1 is a bond with c* of Chemical Formula 2, and the other of a* and b* is hydrogen, deuterium, a substituted or unsubstituted C1 to C10 alkyl group, or a substituted or unsubstituted C6 to C20 aryl group, and $R^1$ to $R^7$ are each independently hydrogen, deuterium, a substituted or unsubstituted C1 to C10 alkyl group, or a substituted or unsubstituted C6 to C20 aryl group.

2. The compound as claimed in claim 1, which is represented by Chemical Formula 1A or Chemical Formula 1B:

[Chemical Formula 1A]

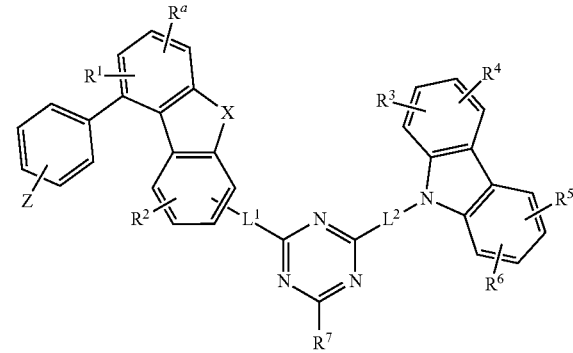

[Chemical Formula 1B]

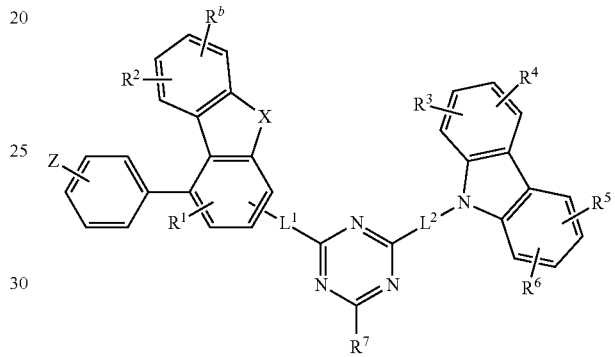

wherein, in Chemical Formula 1A and Chemical Formula 1B,

X is O or S,

Z is hydrogen, deuterium, a substituted or unsubstituted C1 to C10 alkyl group, or a substituted or unsubstituted phenyl group, $L^1$ and $L^2$ are each independently a single bond, or a substituted or unsubstituted C6 to C20 arylene group, and $R^a$, $R^b$, and $R^1$ to $R^7$ are each independently hydrogen, deuterium, a substituted or unsubstituted C1 to C10 alkyl group, or a substituted or unsubstituted C6 to C20 aryl group.

3. The compound as claimed in claim 2, which is represented by one of Chemical Formula 1A-1 to Chemical Formula 1A-4 and Chemical Formula 1B-1 to 1B-3:

[Chemical Formula 1A-1]

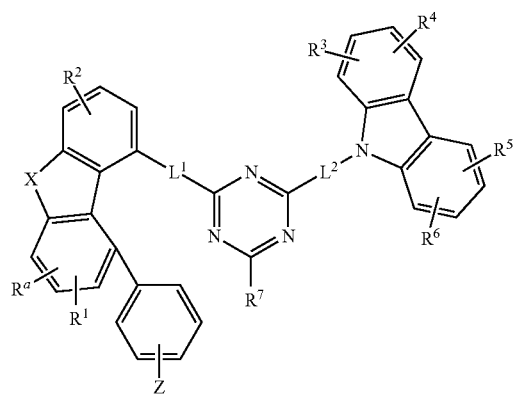

[Chemical Formula 1A-2]

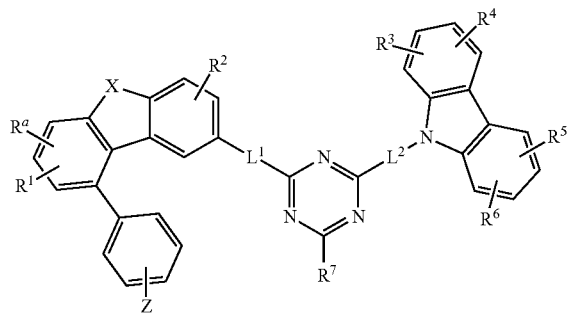

[Chemical Formula 1B-2]

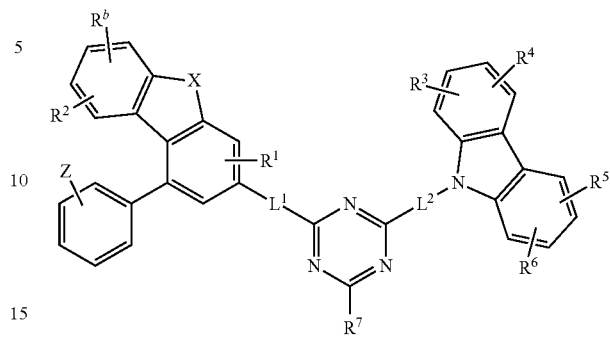

[Chemical Formula 1A-3]

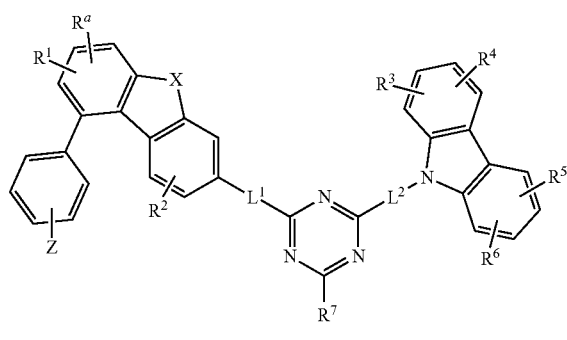

[Chemical Formula 1B-3]

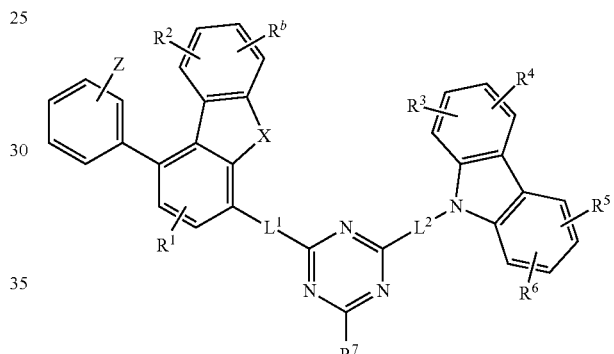

[Chemical Formula 1A-4]

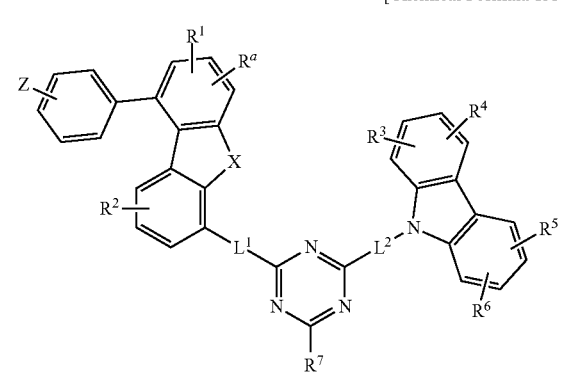

[Chemical Formula 1B-1]

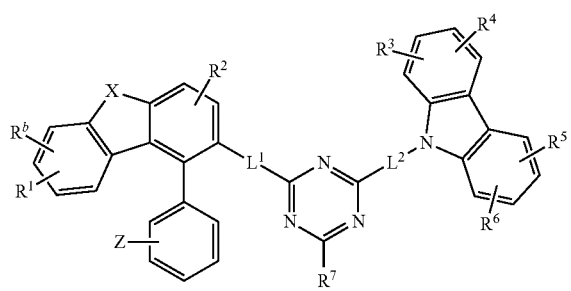

wherein, in Chemical Formula 1A-1 to Chemical Formula 1A-4, and Chemical Formula 1B-1 to Chemical Formula 1B-3, X is O or S, Z is hydrogen, deuterium, a substituted or unsubstituted C1 to C10 alkyl group, or a substituted or unsubstituted phenyl group, $L^1$ and $L^2$ are each independently a single bond, or a substituted or unsubstituted C6 to C20 arylene group, and $R^a$, $R^b$ and $R^1$ to $R^7$ are each independently hydrogen, deuterium, a substituted or unsubstituted C1 to C10 alkyl group, or a substituted or unsubstituted C6 to C20 aryl group.

4. The compound as claimed in claim 3, the compound being represented by Chemical Formula 1A-3 or Chemical Formula 1B-2.

5. The compound as claimed in claim 1, wherein $R^7$ is a substituted or unsubstituted phenyl group, a substituted or unsubstituted biphenyl group, a substituted or unsubstituted naphthyl group, a substituted or unsubstituted terphenyl group, a substituted or unsubstituted anthracenyl group, a substituted or unsubstituted phenanthrenyl group, or a substituted or unsubstituted triphenylenyl group.

6. The compound as claimed in claim 1, the compound being selected from compounds of Group 1:
[Group 1]
[A-1]
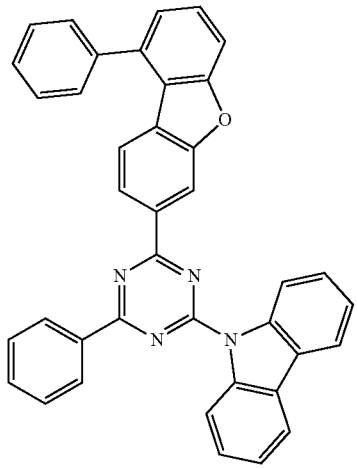
[A-2]
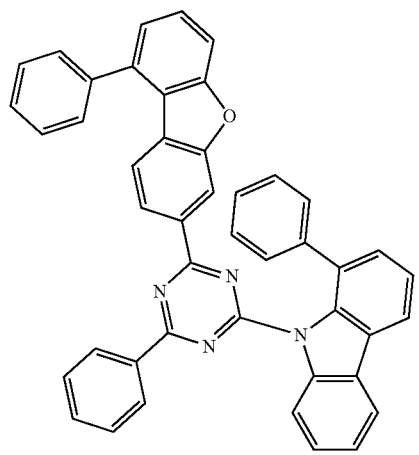
[A-3]
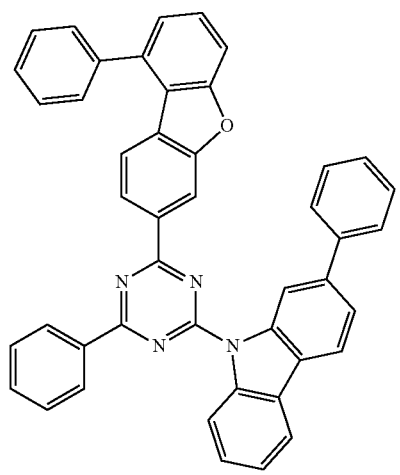
[A-4]
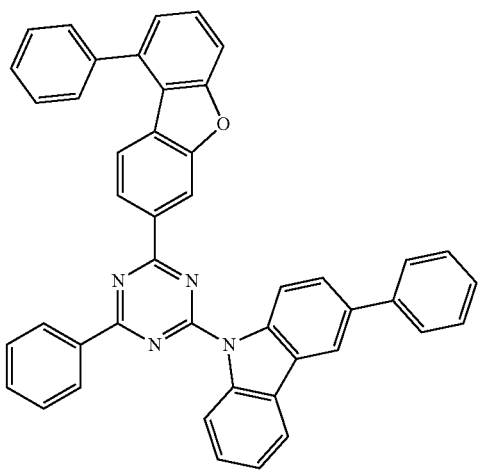
[A-5]
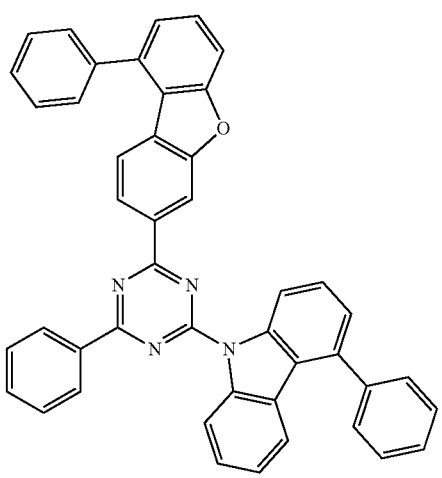
[A-6]
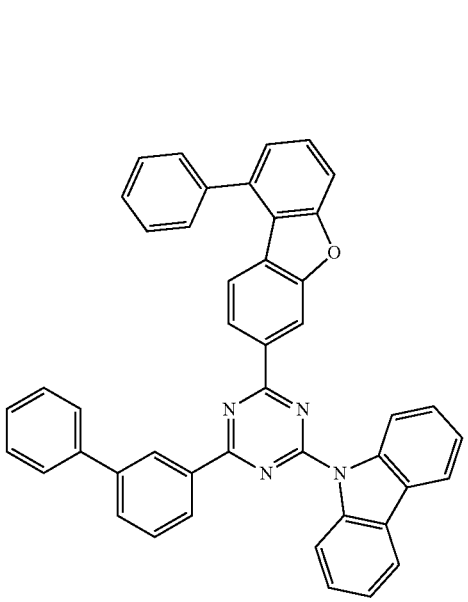

[A-7] 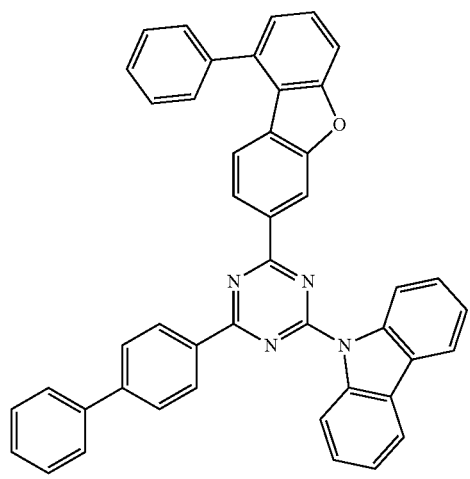
[A-10] 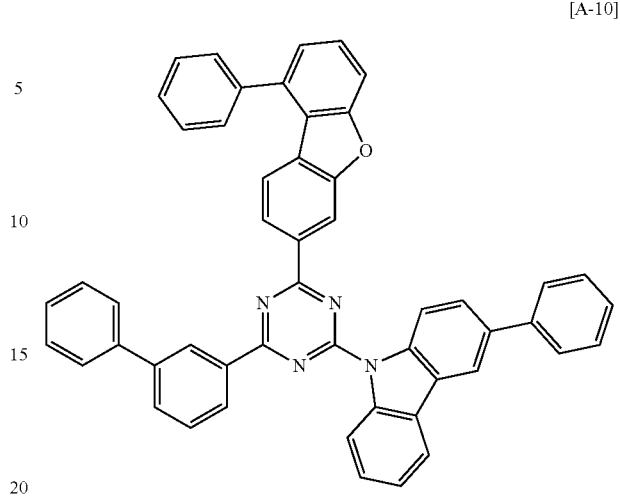
[A-8]
[A-11] 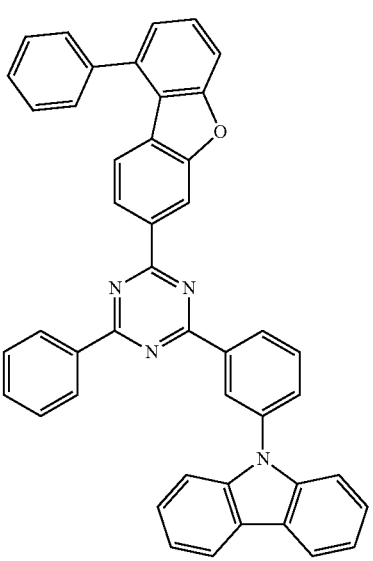
[A-9]
[A-12] 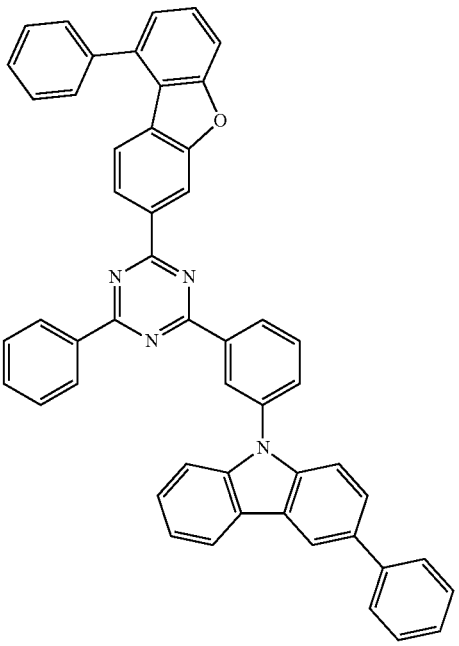

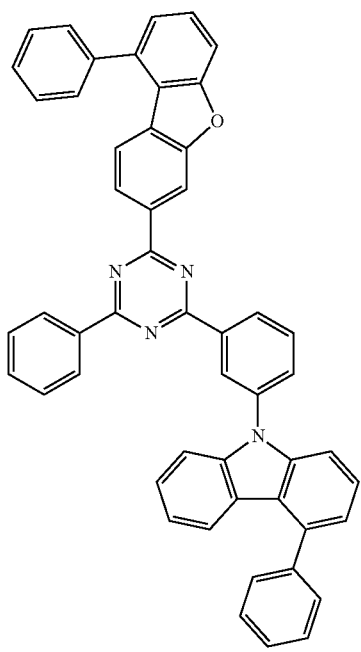
[A-13]
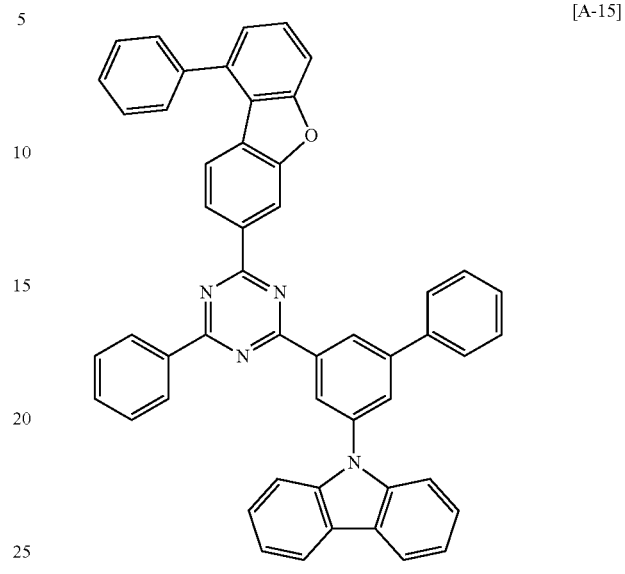
[A-15]
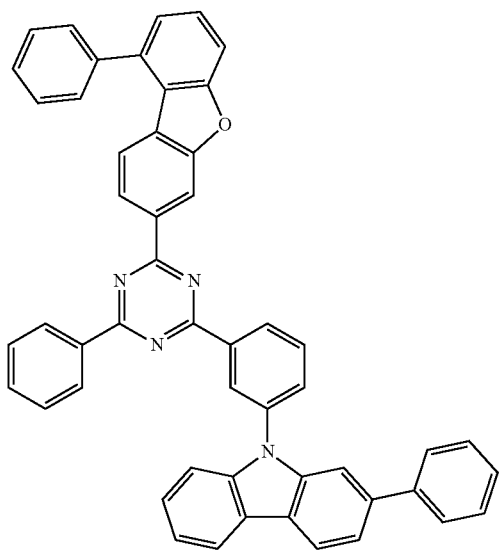
[A-14]
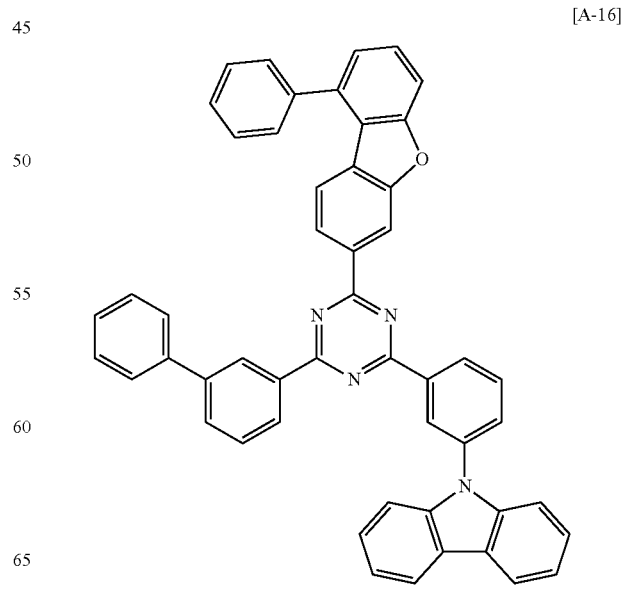
[A-16]

[A-17]
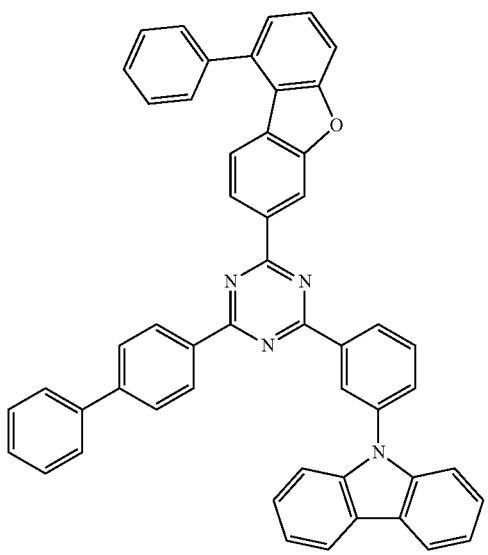
[A-18]
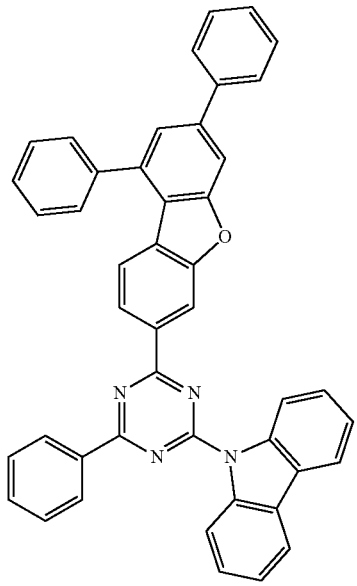
[A-19]
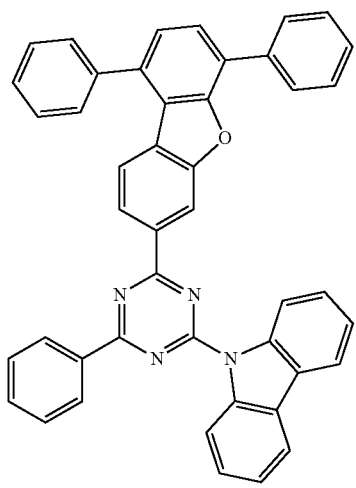
[A-20]
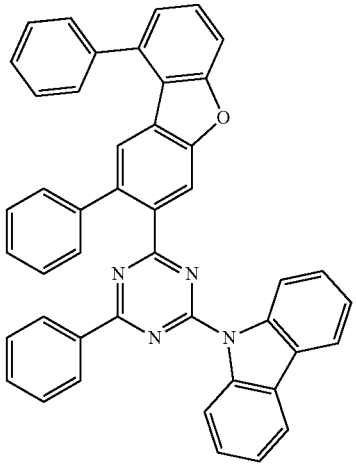
[A-21]
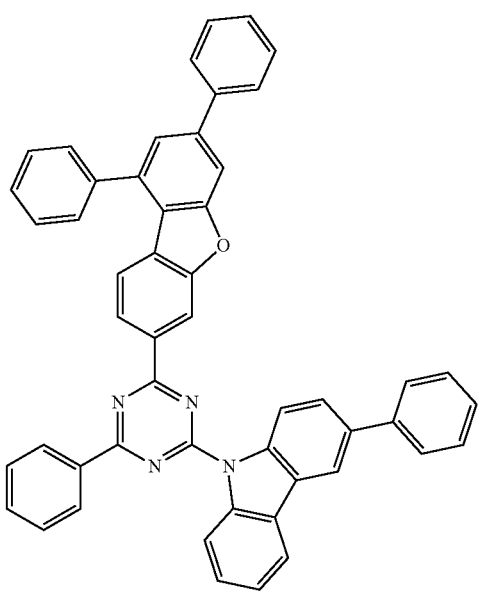

[A-22]
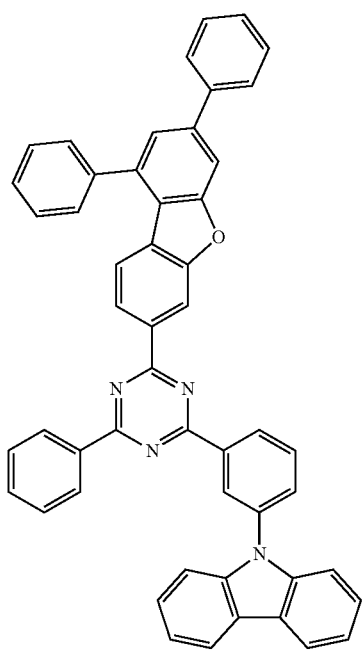
[A-23]
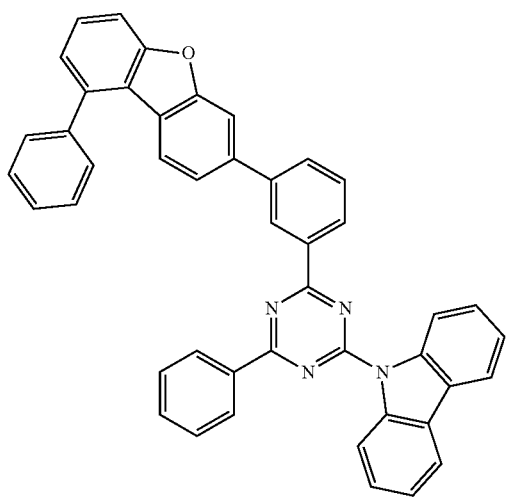
[A-24]
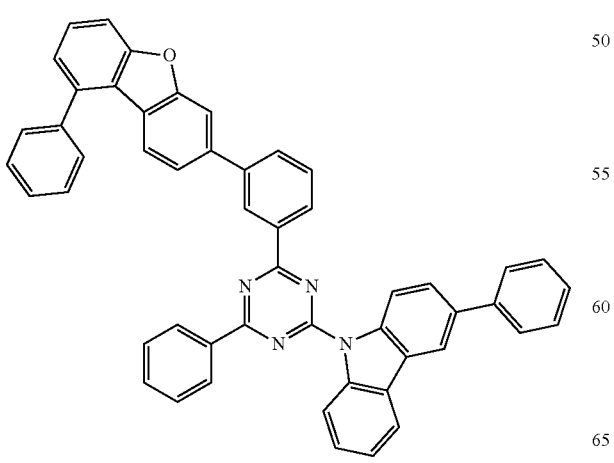
[A-25]
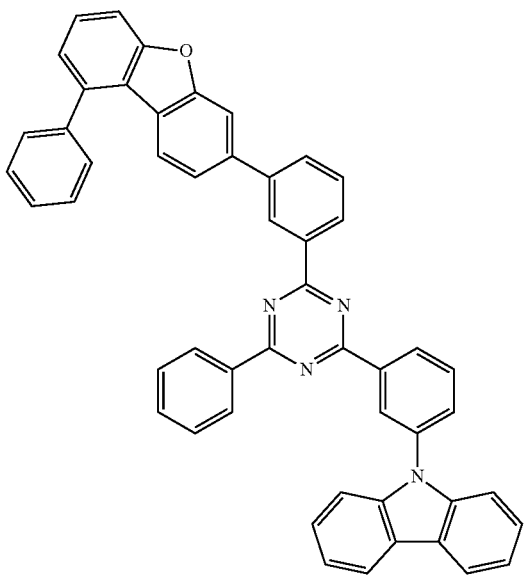
[A-26]
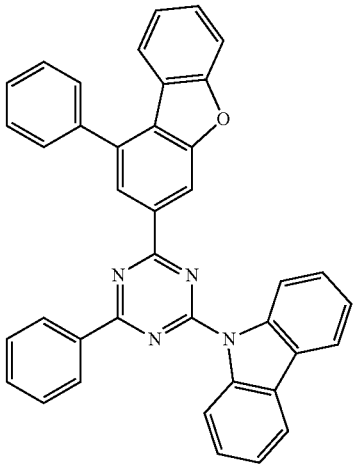
[A-27]
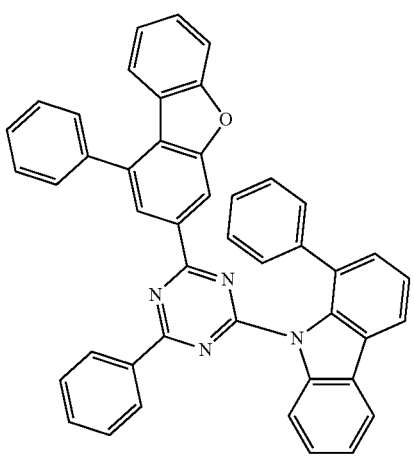

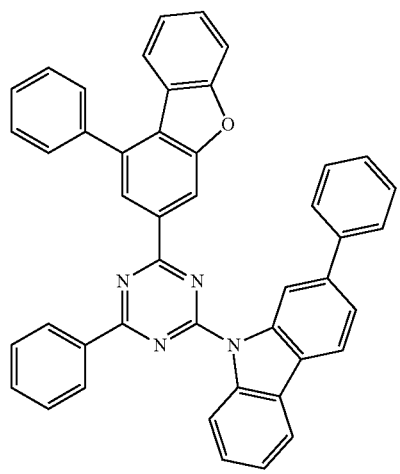
[A-28]
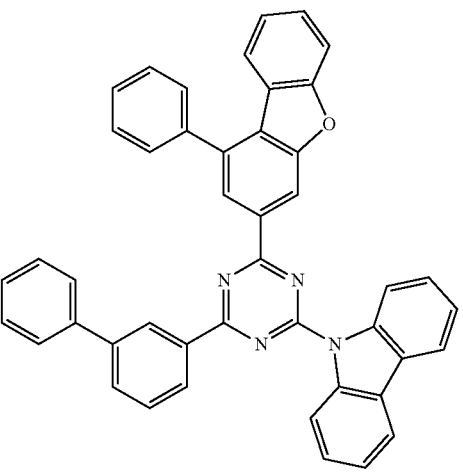
[A-31]
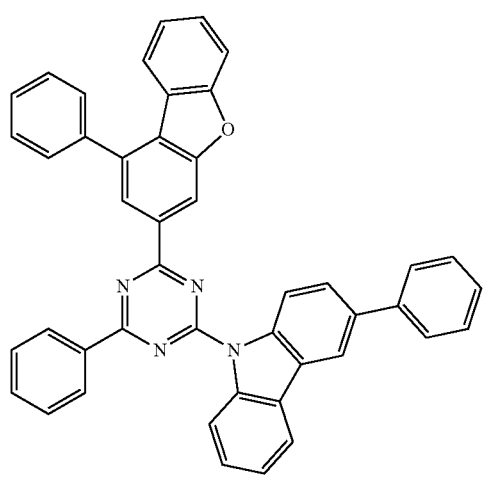
[A-29]
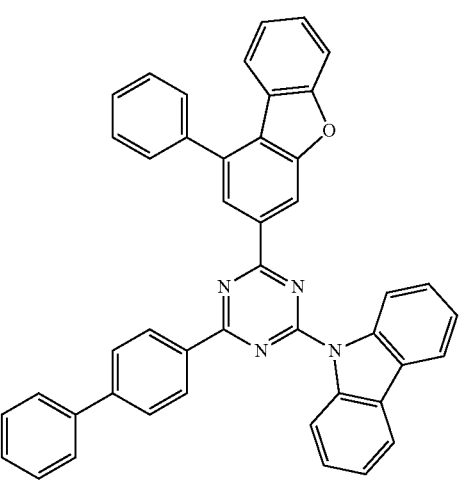
[A-32]
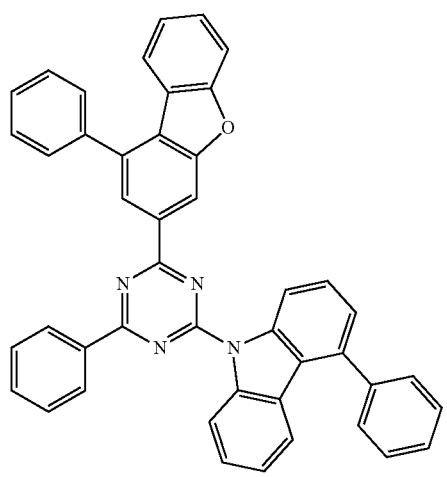
[A-30]
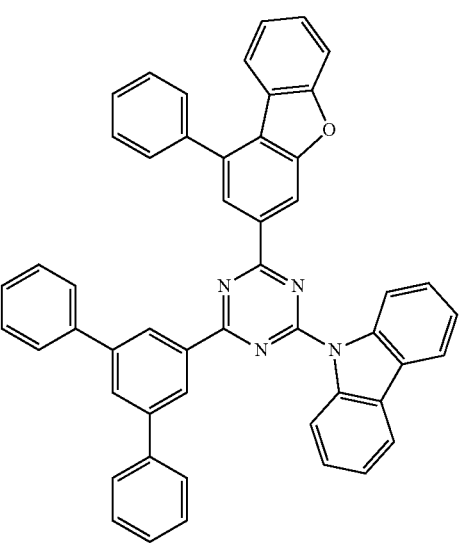
[A-33]

[A-34]
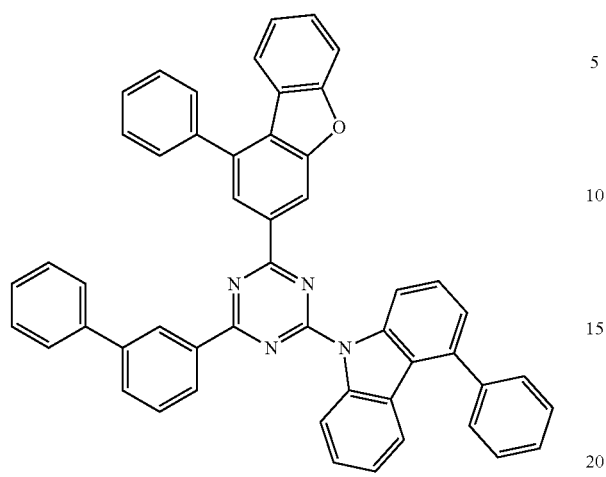
[A-35]
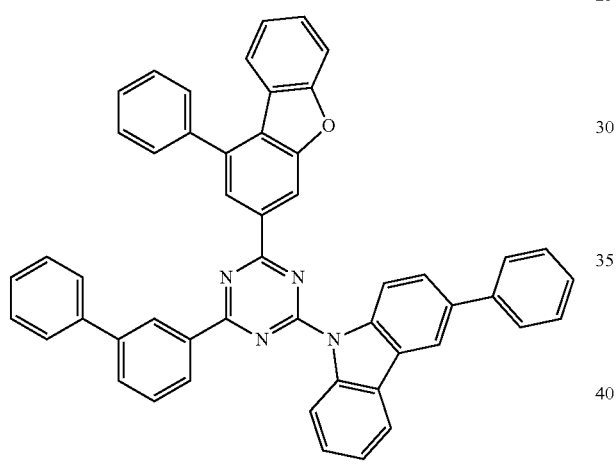
[A-36]
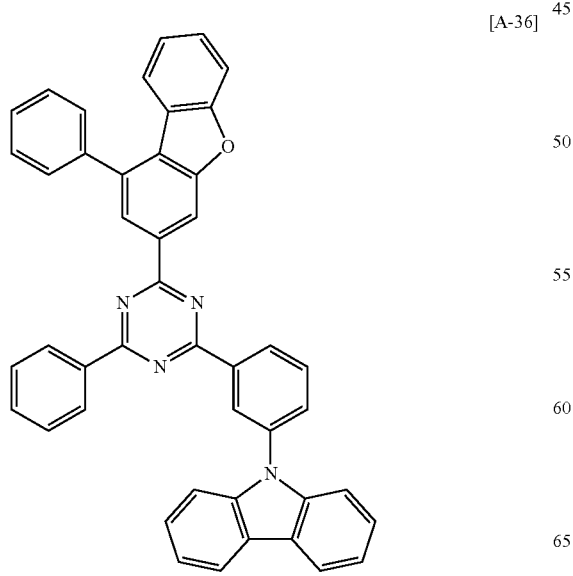
[A-37]
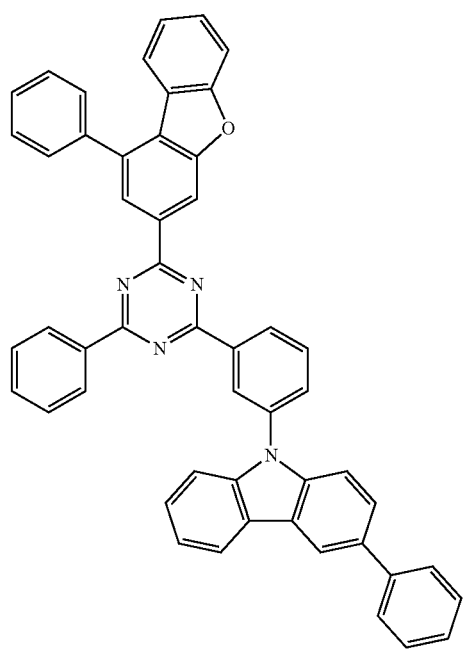
[A-38]
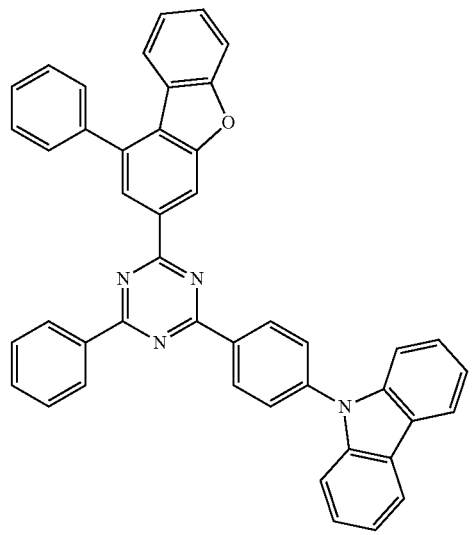

[A-39]
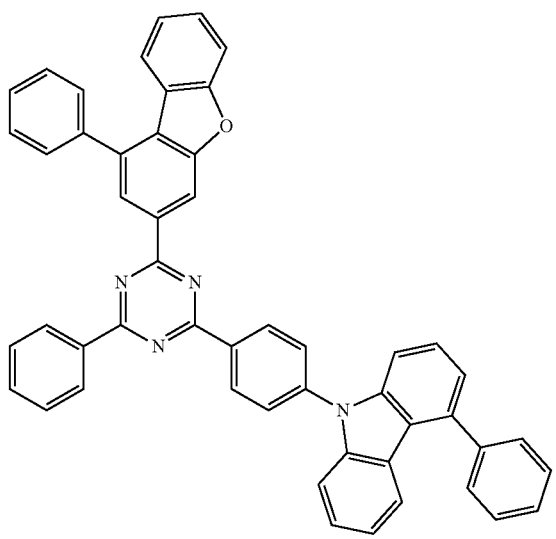
[A-40]
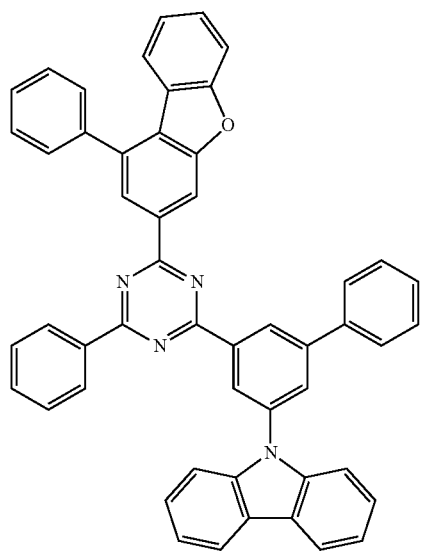
[A-41]
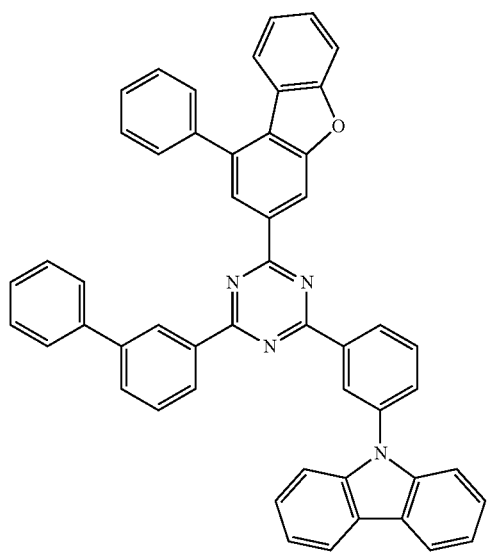
[A-42]
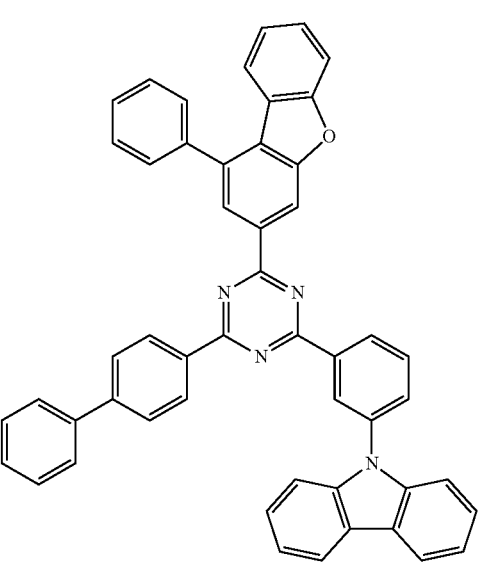
[A-43]
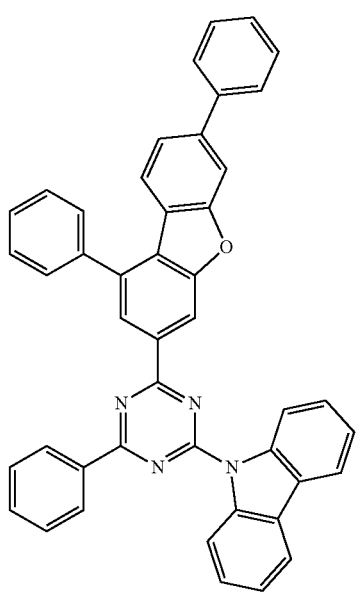
[A-44]
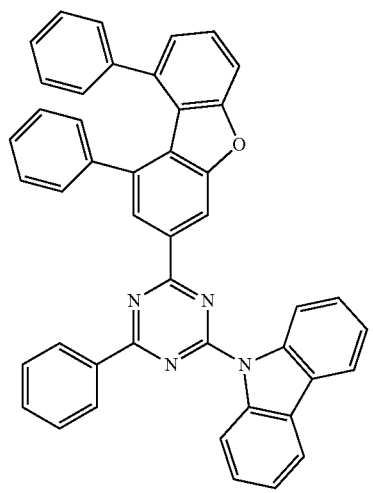

[A-45]
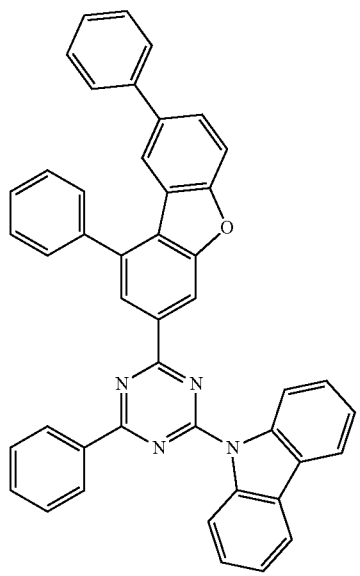
[A-46]
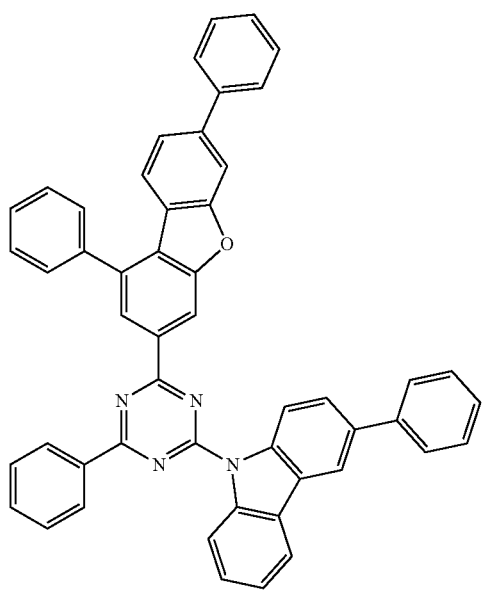
[A-47]
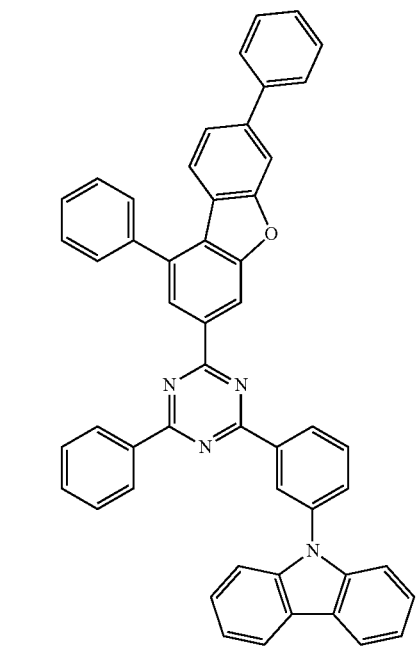
[A-48]
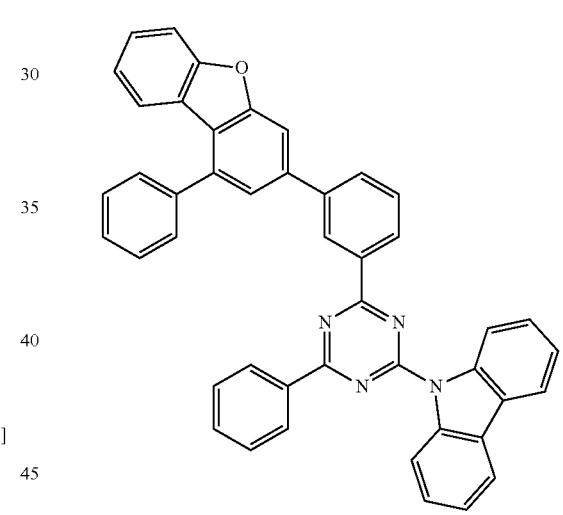
[A-49]
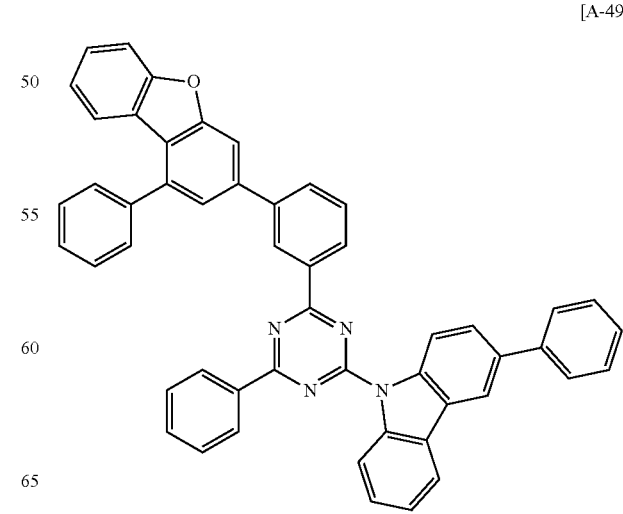

-continued

[A-50]

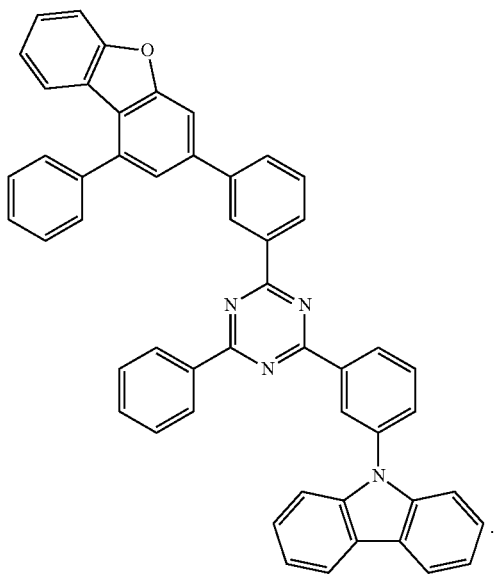

7. A composition, comprising:
the first compound represented by the combination of Chemical Formula 1 and Chemical Formula 2 bonded together as claimed in claim 1, and
a second compound represented by Chemical Formula 3:

[Chemical Formula 3]

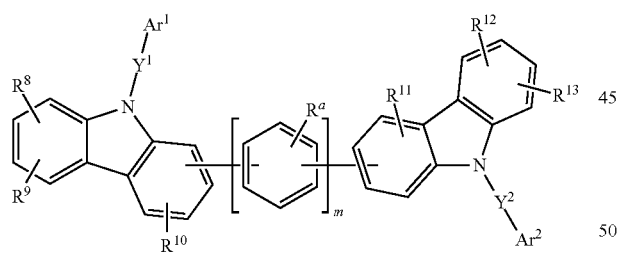

wherein, in Chemical Formula 3, $Y^1$ and $Y^2$ are each independently a single bond or a substituted or unsubstituted C6 to C20 arylene group, $Ar^1$ and $Ar^2$ are each independently a substituted or unsubstituted C6 to C20 aryl group or a substituted or unsubstituted C2 to C30 heterocyclic group, $R^c$ and $R^8$ to $R^{13}$ are each independently hydrogen, deuterium, a substituted or unsubstituted C1 to C10 alkyl group, a substituted or unsubstituted C6 to C20 aryl group, a substituted or unsubstituted C2 to C30 heterocyclic group, a cyano group, or a combination thereof, and m is 0, 1, or 2.

8. The composition as claimed in claim 7, wherein Chemical Formula 3 is represented by Chemical Formula 3A:

[Chemical Formula 3A]

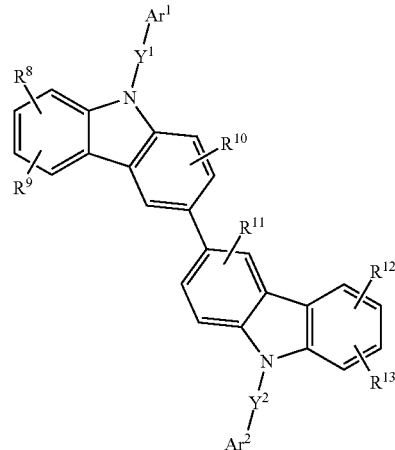

wherein, in Chemical Formula 3A, $Y^1$ and $Y^2$ are each independently a single bond or a substituted or unsubstituted C6 to C20 arylene group, $Ar^1$ and $Ar^2$ are each independently a substituted or unsubstituted C6 to C20 aryl group or a substituted or unsubstituted C2 to C30 heterocyclic group, and $R^8$ to $R^{13}$ are each independently hydrogen, deuterium, a substituted or unsubstituted C1 to C10 alkyl group, a substituted or unsubstituted C6 to C20 aryl group, a substituted or unsubstituted C2 to C30 heterocyclic group, a cyano group, or a combination thereof.

9. The composition as claimed in claim 7, wherein:

Chemical Formula 3 is one of structures of Group II, and —$Y^1$—$Ar^1$ and *—$Y^2$—$Ar^2$ are one of Group III:

[Group II]

C-1

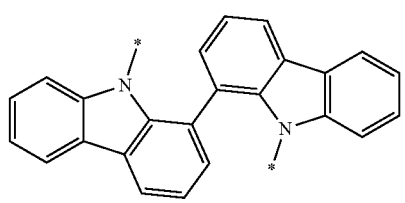

C-2

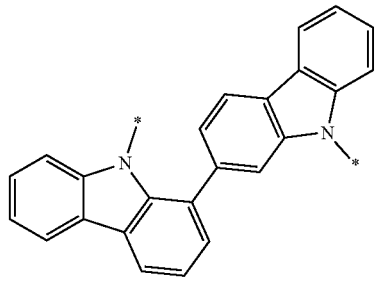

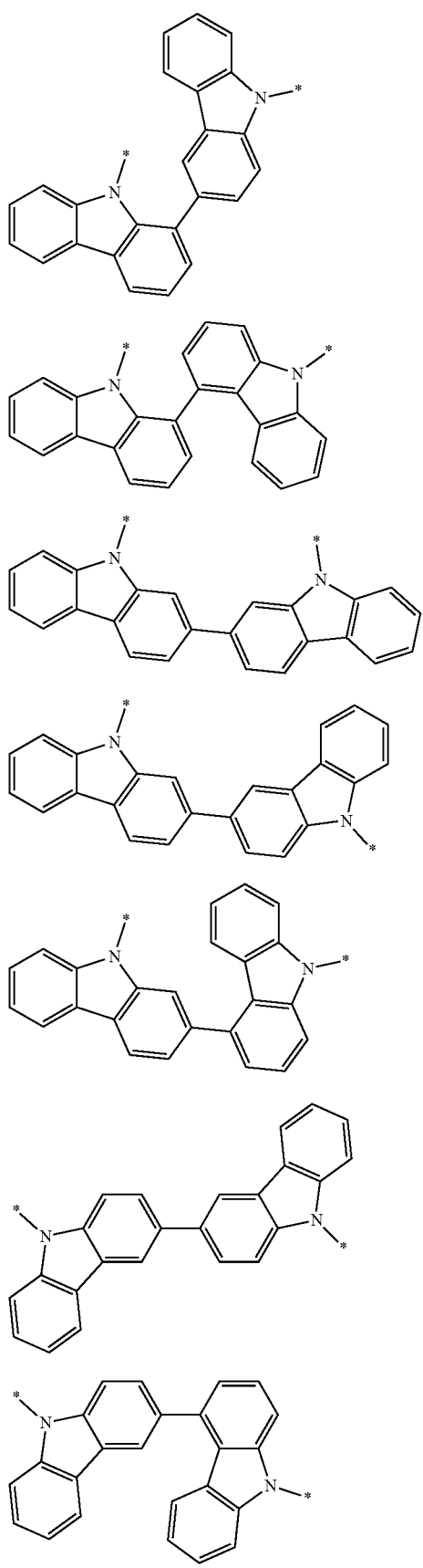
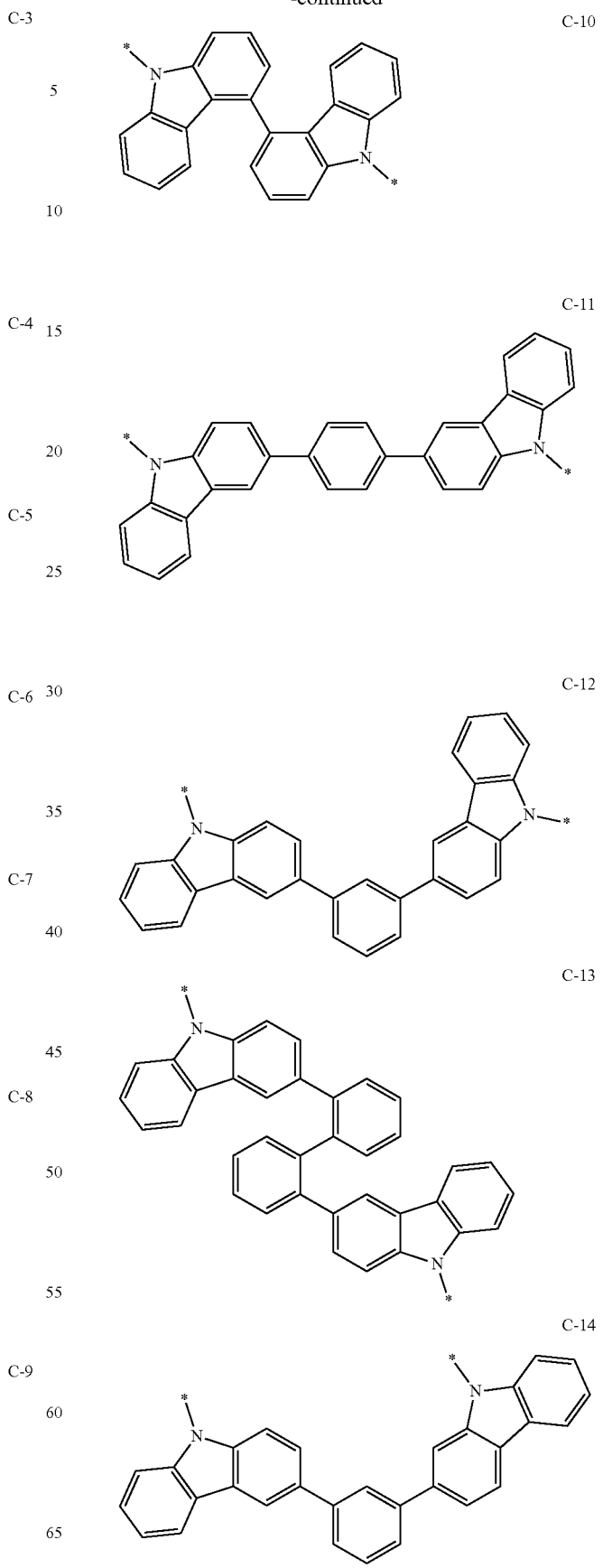

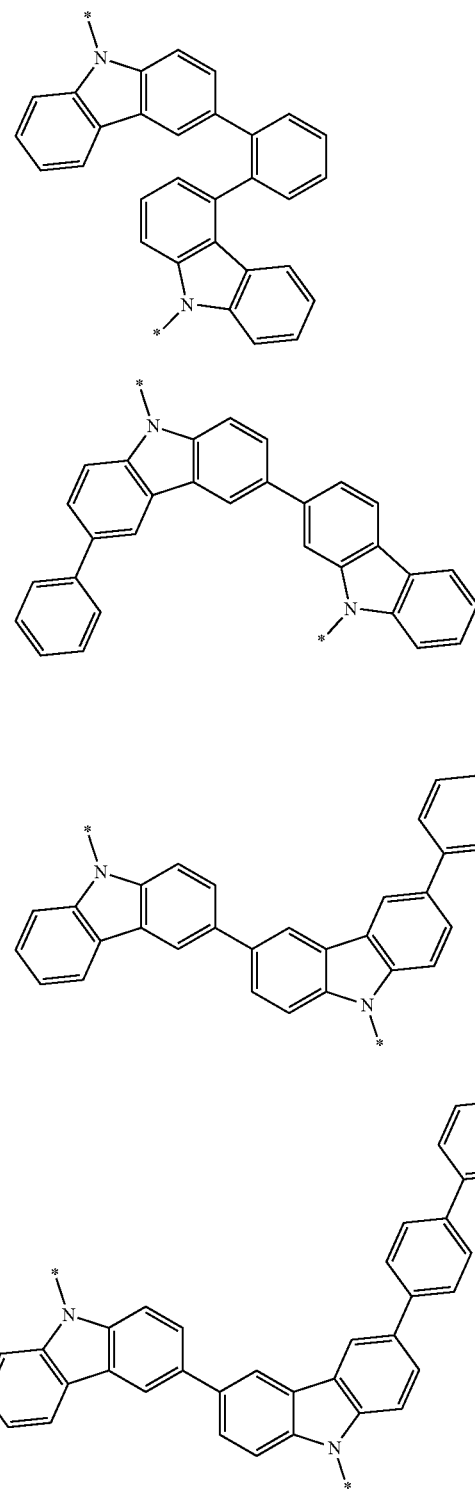
[Group III]
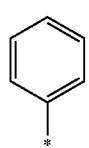
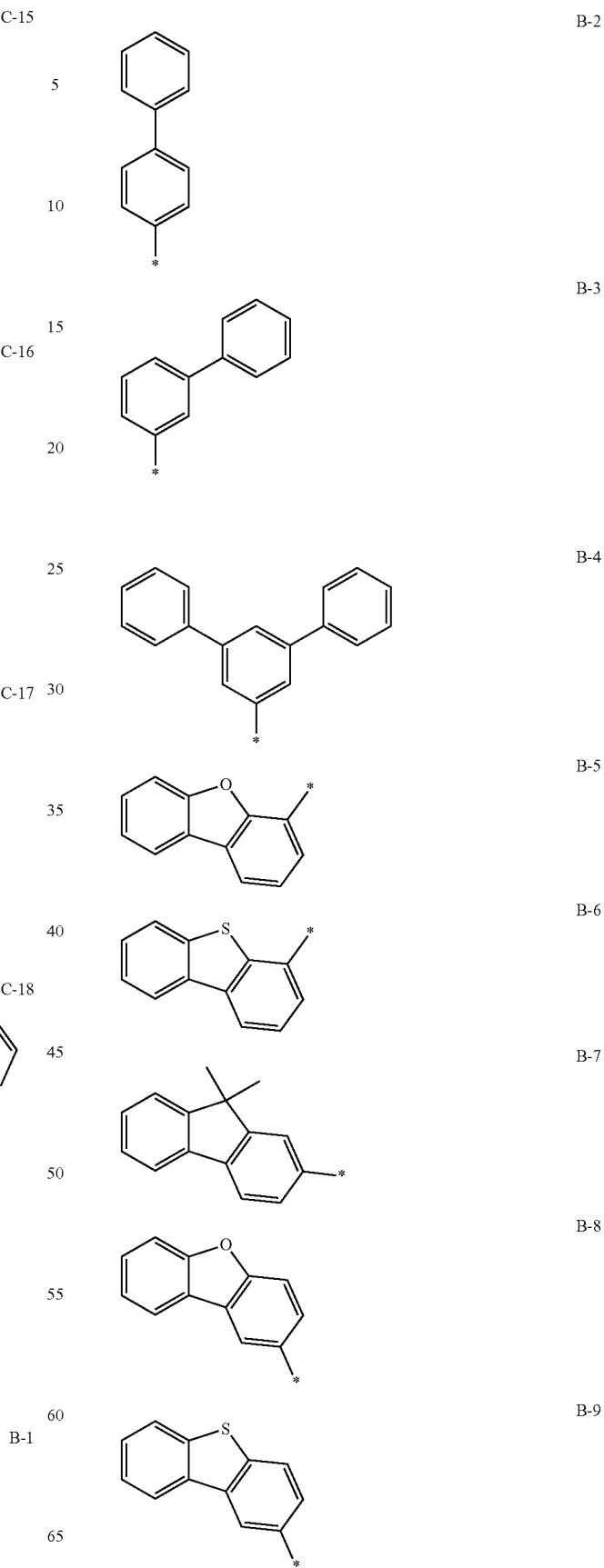

-continued
B-10 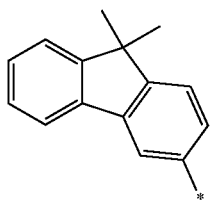
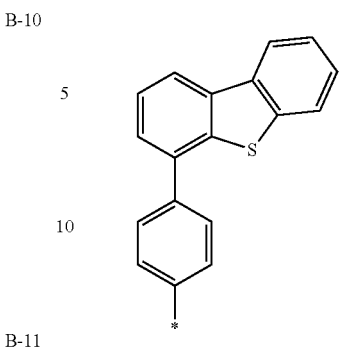
B-11 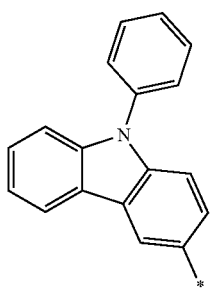
B-17
B-12 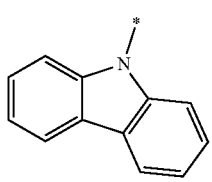
B-18 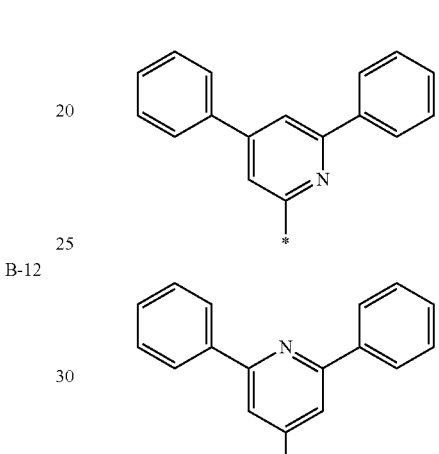
B-13 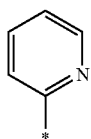
B-19
B-14 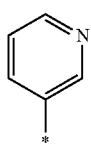
B-20 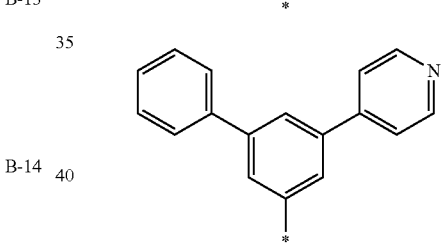
B-15 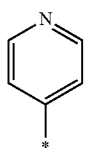
B-21 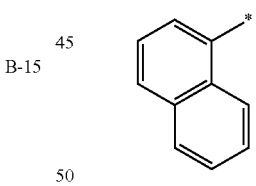
B-22 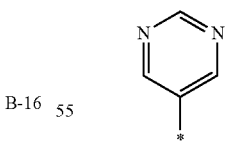
B-16 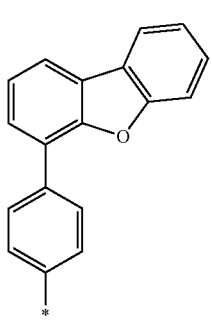
B-23 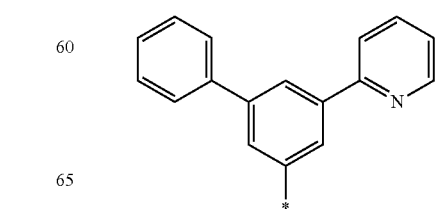

-continued

B-24 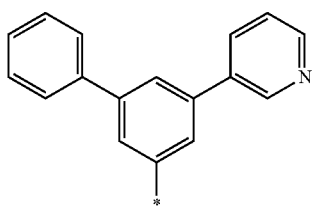

B-25 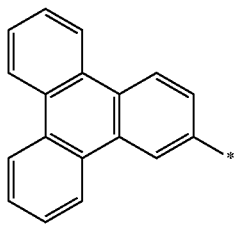

B-26 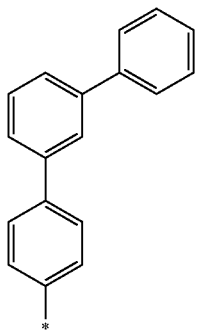

B-27 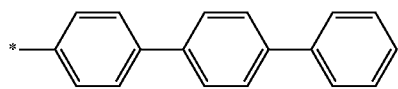

-continued

B-28 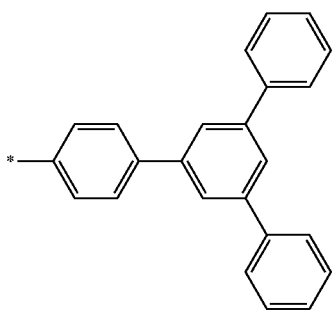

wherein, in Group II and Group III, * is a linking point.

10. The composition as claimed in claim 9, wherein:
Chemical Formula 3 is represented by Chemical Formula C-8 or Chemical Formula C-17 of Group II, and —$Y^1$—$Ar^1$ and *—$Y^2$—$Ar^2$ are one of Group III.

11. An organic optoelectronic device, comprising:
an anode and a cathode facing each other,
at least one organic layer disposed between the anode and the cathode, wherein the organic layer includes the composition as claimed in claim 7.

12. The organic optoelectronic device as claimed in claim 11, wherein:
the organic layer includes a light emitting layer, and
the light emitting layer includes the composition.

13. A display device comprising the organic optoelectronic device as claimed in claim 11.

14. An organic optoelectronic device, comprising:
an anode and a cathode facing each other,
at least one organic layer disposed between the anode and the cathode, wherein the organic layer includes the compound as claimed in claim 1.

15. The organic optoelectronic device as claimed in claim 14, wherein:
the organic layer includes a light emitting layer, and
the light emitting layer includes the compound.

16. A display device comprising the organic optoelectronic device as claimed in claim 14.

* * * * *